United States Patent
Wu et al.

(10) Patent No.: US 6,995,299 B2
(45) Date of Patent: Feb. 7, 2006

(54) PROPAGATION OF HUMAN HEPATOCYTES IN NON-HUMAN ANIMALS

(75) Inventors: George Y. Wu, Avon, CT (US); Catherine H. Wu, Avon, CT (US)

(73) Assignee: University of Connecticut, Farmington, CT (US)

( * ) Notice: Subject to any disclaimer, the term of this patent is extended or adjusted under 35 U.S.C. 154(b) by 586 days.

(21) Appl. No.: 09/930,781

(22) Filed: Aug. 15, 2001

(65) Prior Publication Data

US 2002/0157121 A1 Oct. 24, 2002

Related U.S. Application Data

(63) Continuation-in-part of application No. PCT/US00/05713, filed on Mar. 3, 2000, which is a continuation-in-part of application No. 09/431,901, filed on Nov. 2, 1999, now Pat. No. 6,525,242.

(51) Int. Cl.
*A01K 67/00* (2006.01)
*A01K 67/033* (2006.01)
*A01N 63/00* (2006.01)
*A01N 65/00* (2006.01)
*C12N 5/08* (2006.01)

(52) U.S. Cl. .................... 800/9; 424/93.1; 424/93.7; 435/325; 435/370; 800/8

(58) Field of Classification Search .............. 800/8, 800/9; 435/325, 370; 424/93.1, 93.7
See application file for complete search history.

(56) References Cited

U.S. PATENT DOCUMENTS

| 5,759,830 A | 6/1998 | Vacanti et al. | 435/180 |
|---|---|---|---|
| 5,858,328 A | 1/1999 | Reisner | 424/9.2 |
| 6,034,297 A | 3/2000 | Vierling | 800/9 |
| 2001/0007153 A1 * | 7/2001 | Brown et al. | 800/8 |

FOREIGN PATENT DOCUMENTS

| WO | WO 93/18144 | 9/1993 |
|---|---|---|
| WO | WO 94/02601 | 2/1994 |
| WO | WO 94/27556 | 12/1994 |
| WO | WO 95/09235 | 4/1995 |
| WO | WO 96/39810 | 12/1996 |
| WO | WO 99/16307 | 4/1999 |
| WO | WO 00/17338 | 3/2000 |
| WO | WO 00/18193 | 3/2001 |
| WO | WO 01/32009 | 5/2001 |

OTHER PUBLICATIONS

Ilan et al. (1996) Induction of central tolerance by intrathymic inoculation of adenoviral antigens into the host thymus permits long–term gene therapy in Gunn rats. J. Clin. Invest. 98: 2640–2647.*

Ilan et al. (1997) Oral tolerization to adenoviral antigens permits long–term expression using recombinant adenoviral vectors. J. Clin. Invest. 99: 1098–1106.*

Kline et al. (1994) Development of tolerance to experimental cardiac allografts in utero. Ann. Thoracic Surgery 57: 72–75.*

Kuby, J. (1997) Immunology ($3^{rd}$ edition) W.H. Freeman and Company, New York, pp. 565–566 and 608.*

Nussenblatt et al. (1990) Inhibition of S–antigen induced experimental autoimmune uveoretinitis by oral induction of tolerance with S–antigen. J. Immunol. 144: 1689–1695.*

Walter et al. Successful expression of human factor IX following repeat administration of an adenoviral vector in mice. Proc. Natl. Acad. Sci. USA 93: 3056–3061.*

Rhim et al. (1995) Complete reconstitution of mouse liver with xenogeneic hepatocytes. Proc. Natl. Acad. Sci. USA 92: 4942–4946.*

Attavar et al., 1997, "Mechanisms of intrathymic tolerance induction to isolated rat hepatocyte allografts", Hepatology 26:1287–1295.

Aviv and Leder, 1972, "Purification of biologically active globin messenger RNA by chromatography on oligothymidic acid–cellulose", Proc. Natl. Acad. Sci. U.S.A., 69:1408–1412.

Berchtold, 1989, "A simple method for direct cloning and sequencing cDNA by the use of a single specific oligonucleotide and oligo(dT) in a polymerase chain reaction (PCR)", Nuc. Acids Res. 17:453.

Bertolini et al., 1993, "The human bone–marrow–derived B–cell line CE, susceptible to hepatitis C virus infection", Res. Virol. 144:281–285.

Billingham et al., 1953, Actively acquired tolerance of foreign cells, Nature 172:603–606.

Bradley, 1980, "Mixed Lymphocytes Responses", in Selected Methods in Cellular Immunology, Mishell and Shiigi eds., W.H. Freeman and Co., p. 162–172.

Blum et al., 1991, "Naturally occurring missense mutation in the polymerase gene terminating hepatitis B virus replication", J. Virol. 65:1836–1842.

Brown et al., 2000, "A long–term hepatitis B viremia model generated by transplanting nontumorigenic immortalized human hepatocytes in Rag–2–deficient mice", Hepatology 31:173–181.**

(Continued)

*Primary Examiner*—Anne-Marie Falk
(74) *Attorney, Agent, or Firm*—Baker Botts LLP

(57) ABSTRACT

The present invention relates to the preparation of non-human animals having chimeric livers, whereby some or substantially all of the hepatocytes present are human hepatocytes. It is based, at least in part, on the discovery that rats, tolerized in utero against human hepatocytes, were found to serve as long-term hosts for human hepatocytes introduced post-natally, and the introduced hepatocytes maintained their differentiated phenotype, as evidenced by continued production of human albumin. The present invention further relates to the use of such animals as models of various liver diseases, including viral invention. Such embodiments are based on the discovery that transplanted human hepatocytes in chimeric livers were found to be susceptible to Hepatitis B virus and Hepatitis C virus infection.

6 Claims, 35 Drawing Sheets

OTHER PUBLICATIONS

Figure 1:
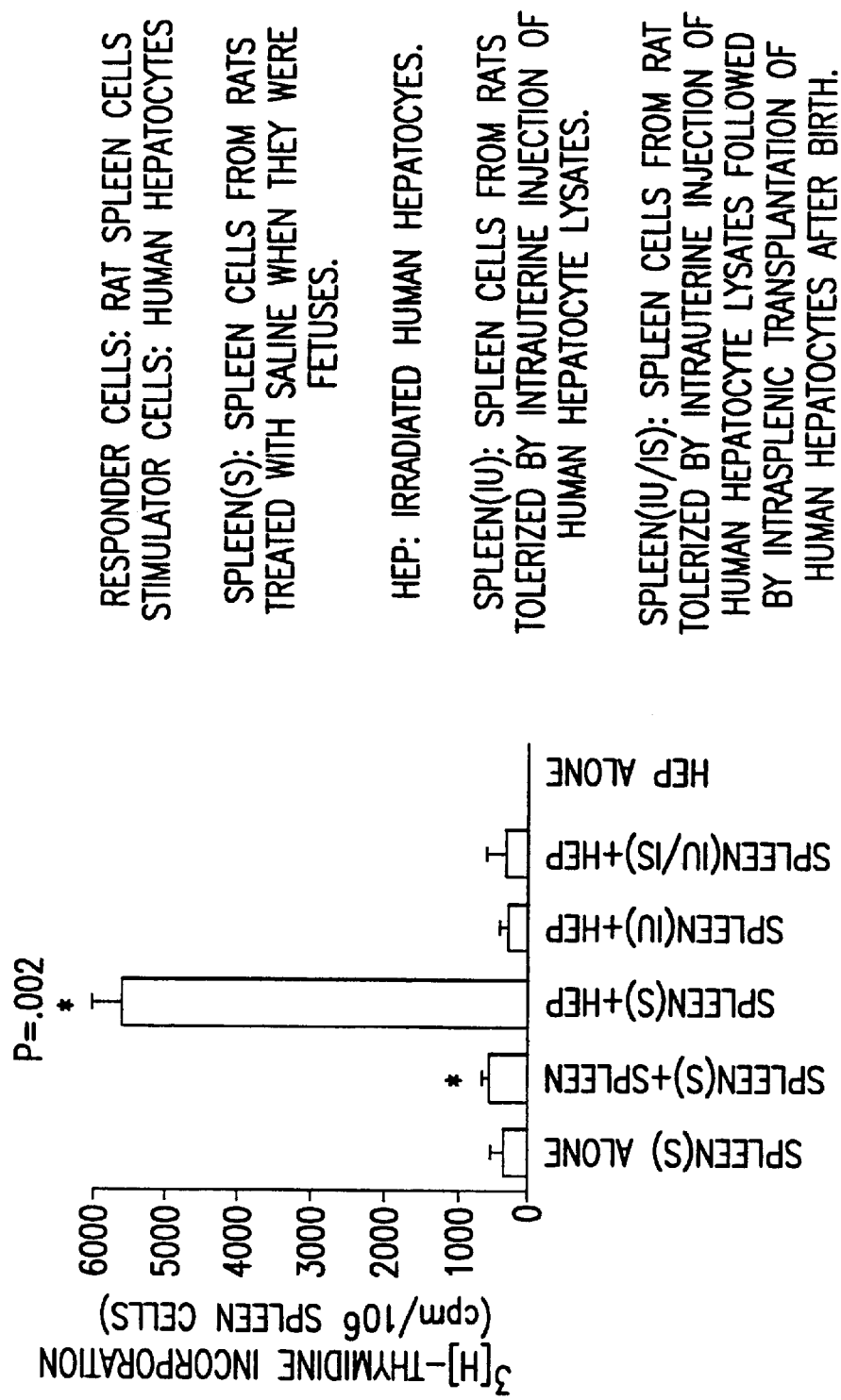

Bumgardner et al., 1998, "A functional model of hepatocyte transplantation for in vivo immunologic studies", Transplantation 65:53–61.**

Carlson et al., 1989, "Accumulation of PiZ α1–antitrypsin causes liver damage in transgenic mice", J. Clin. Invest. 83:1183–1190.

Chang et al., 1989, "Biosynthesis of the reverse transcriptase of hepatitis B viruses involves de novo translational initiation not ribosomal frameshifting", Nature 337:364–368.

Chomczynski and Sacchi, 1987, "Single–step method of RNA isolation by acid guanidinium thiocyanate–phenol–chloroform extraction", Anal. Biochem. 162:156–159.

Choo et al., 1991, "Genetic organization and diversity of the hepatitis C virus", Proc. Natl. Acad. Sci. U.S.A., 88:2451–2455.

Choo et al., 1989, "Isolation of a cDNA clone derived from a blood–borne non–A, non–B viral hepatitis genome", Science 244:359–362.

Clarke, 1997, "Molecular virology of hepatitis C virus", J. Gen. Virol., 78:2397–2410.

Clonetics 1998–1999: Normal Human Cell Systems Catalog, 1998.

Cohen, 1999, "The scientific challenge of hepatitis C", Science 285:26–30.

Cobourn et al., 1987, "Allogenic intrasplenic hepatocyte transplantation in the Gunn rat using cyclosporine A immunosuppression", Transpl. Proc. 19:1002–1003.**

Cribier et al., 1995, "In vitro infection of peripherial blood mononuclear cells by hepatitis C virus", J. Gen Virol. 76:2485–2491.

Culver et al., 1992, "In vivo gene transfer with retroviral vector–producer cells for treatment of experimental brain tumors", Science 256:1550–1552.

Cusick et al., 1997, "The effect of donor and recipient age on engraftment of tissue engineered liver", J. Ped. Surg. 32:357–360.**

Darby et al., 1986, "Observations on rat spleen reticulum during the development of syngeneic hepatocellular implants", Br. J. Exp. Pathol. 67:329–339.**

Davis et al., 1998, "Interferon alpha–2b alone or in combination with ribavirin for the treatment of relapse of chronic hepatitis C", N. Engl. J. Med. 339:1493–1499.

De Clercq, 1984, "Biochemical aspects of the selective antiherpes activity of nucleoside analogues", Biochem. Biopharmacol. 33:2159–2169.

Demetriou et al., 1988, "Transplantation of microcarrier–attached hepatocytes into 90% partially hepatectomized rats", Hepatology 8:1006–1009.**

Dienstag et al, 1999, "Lamivudine al initial treatment for chronic hepatitis B in the United States", New Eng. J. Med. 341:1256–1263.

Dorling et al., 1997, "Clinical xenotransplantation of solid organs", Lancet. 349:867–871.

Fabrega et al., 1995, "Amelioration of analbuminemia by transplantation of allogenic hepatocytes in tolerized rats", Transplantation 59:1362–1364.**

Farber and Sarma, 1987, "Chemical carcinogenesis: the liver as a model", in Concepts and Theories in Carcinogenesis, Maskens et al. (eds.) Elsevier, Amsterdam, pp. 185–220.

Feinstone et al., 1981, "Non–A, non–B hepatitis in chimpanzees and marmosets", J. Infect. Dis. 144:588–598.

Friend et al., 1999, "Engineering hepatocyte spheroids for potential application in a bioartificial liver", http://www.cems.umn.edu/~wshu_grp/bal/balold.html.

Fyfe et al., 1978, "Thymidine kinase from herpes simplex virus phosphorylates the new antiviral compound, 9–(2–hydroxyethoxymethyl)guanine", J. Biol. Chem. 253:8721–8727.

Ganem, 1996, "Hepadnaviridae and their replication", In Fields et al eds., Fields Virology, Lippincott–Raven, Philadelphia, PA, pp. 2703–2737.

Galun et al., 1995, "Hepatitis C virus viremia in SCID BNX mouse chimera", J. Infect. Dis. 172:25–30.

Gerber et al., 1983, "Phenotypic characterization of hepatic proliferation: antigenic expression by proliferating epithelial cells in fetal liver, massive hepatic necrosis and nodular transformation of the liver", AJP 110:70–74.

Gordon et al., 1998, "Prolonged survival of rat islet and skin xenografts in mice treated with donor splenocytes and anti–CD154 monoclonal antibody", Diabetes 47:1199–1206.**

Grossman et al., 1994, "Successful ex vivo gene therapy directed to liver in a patient with familial hypercholesterolaemia", Nat. Genet. 6:335–341.**

Groth et al., 1977, "Correction of hyperbilirubinemia in the glucuronyltransferase–deficient rat by intraportal hepatocyte transplantation", Transpl. Proc. 9:313–316.**

Guguen–Guillouzo et al., 1982, "High yield preparation of isolated human adult hepatocytes by enzymatic perfusion of the liver", Cell. Biol. Int. Rep. 6:625–628.

Gupta et al., 1996, "Hepatocyte transplantation: progress toward liver repopulation", Prog. Liv. Dis. 14:199–222.

Hadju et al., 1996, "In vitro allogenic hematopoietic stem cell transplantation to induce tolerance", Fetal Diagnosis and Therapy 11:241–248.

Heard, 1994, "Current therapeutic relevance of liver gene transfer", Hepatology 20:253–256.**

Heckel et al., 1990, "Neonatal bleeding in transgenic mice expressing urokinase–type plasminogen activator" Cell 62:447–456.**

Henry and Watson, 1980, "Immunization in microsuspension cultures", in Selected Methods in Cellular Immunology, Mishell and Shiigi (eds.) W.H. Freeman and Co., pp. 65–68.

Hollinger, 1996, "Hepatitis B Virus" in Fields Virology, Third Edition, Lippincott–Raven, New York, pp. 2739–2742, 2748–2751.

Holzman et al., 1993, "Selective intraportal hepatocyte transplantation in analbuminemic and Gunn rats", Transplantation 55:1213–1219.**

Iacovacci et al., 1993, "Replication and multiplication of hepatitis C virus genome in human foetal liver cells", Res. Virol. 144:275–279.

Ilan et al., 1999, "The hepatitis B virus–trimera mouse: a model for human HBV infection and evaluation of anti–HBV therapeutic agents", Hepatology 29:553–562.**

Ito et al., 1996, "Cultivation of hepatitis C virus in primary hepatocyte culture from patients with chronic hepatitis C results in release of high titre infectious virus", J. Gen. Virol. 77:1043–1054.

Jauregui et al., 1996, "Use of mammalian liver cells for artificial liver support", Cell Transplantation 5:353–367.**

Jung et al., 1999, "Initiation of mammalian liver development from endoderm by fibroblast growth factors", Science 284:1998–2002.

Kappler et al., 1987, "T cell tolerance by clonal elimination in the thymus", Cell 49:273–280.

Kato et al., 1995, "Susceptibility of human T–lymphocytropic virus type I infected cell line MT–2 to hepatitis C virus infection", Biochem. Biophys. Res. Commun. 206:863–869.

Kato et al., 1990, "Molecular cloning of the human hepatitis C virus genome from Japanese patients with a non–A, non–B hepatitis", Proc. Natl. Acad. Sci. U.S.A., 87:9524–9528.

Kline et al., 1994, "Development of tolerance to experimental cardiac allografts in utero", Ann. Thorac. Surg. 57:72–75.

Knodell et al., 1981, "The Woeful cation: mechanisms for its hepatic uptake", Hepatology 1:524.

Kolberg et al., 1994, "The bystander effect in gene therapy: great, but how does it work?", J. NIH Res. 6:62–64.

Kolykhalov et al., 1997, "Transmission of hepatitis C by intrahepatic inoculation with transcribed RNA", Science 277:570–574.

Krumlauf et al., 1985, "Regulated expression of α–fetoprotein genes in transgenic mice", Cold Spring Harbor Symp. Quant. Biol. 5–0:371–378.

Lanford et al., 1994, "Demonstration of in vitro infection of chimpanzee hepatocytes with hepatitis C virus using strand specific RT/PCR", Virol. 202:606–614.

Lanford et al., 1995, "Lack of detection of negative–strand hepatitis C virus RNA in peripheral blood mononuclear cells and other extrahepatic tissues by the highly strand–specific rTth reverse transcriptase PCR", J. Virol. 69:8079–8083.

Liang, 1998, "Combination therapy for hepatitis C infection", N. Engl. J. Med. 339:1549–1550.

Lieber et al., 1996, "Elimination of hepatitis C virus RNA in infected human hepatocytes by adenovirus–mediated expression of ribozymes", J. Virol. 70:8782–8791.

Lieber et al., 1995, "Adenovirus–mediated urokinase gene transfer induces liver regeneration and allows for efficient retrovirus transduction of hepatocytes in vivo", Proc. Natl. Acad. Sci. U.S.A., 92:6210–6214.

Lohmann et al., 1999, "Replication of subgenomic hepatitis C virus RNAs in a hepatoma cell line", Science 285:110–113.**

Major and Feinstone, 1997, "The molecular virology of hepatitis C", Hepatology 25:1527–1538.

Maganto et al, 1988, "Effect of Ciclosporin on allogenic hepatocyte transplantation: a morphological study", Eur. Surg. Res. 20:248–253.**

Main et al., 1999 "Hepatitis" in *Antibiotic Chemotherapy, 7th Edition*, Chapter 51, pp. 721–731.**

Makowka et al., 1986, "Allogenic hepatocyte transplantation in the rat spleen under cyclosporine immunosuppression", Transplantation 42:537–541.**

Markus et al., 1997, "Selective intraportal transplantation of DiI–marked isolated rat hepatocytes", Cell Transplantation 6:455–462.

Marucci et al., 1997, "Effect of xanthine analog on human hepatocellular carcinoma cells (Alexander) in culture and in xenografts in SCID mice", Hepatology 26:1195–1202.

Matas et al., 1976, "Hepatocellular transplantation for metabolic deficiencies: decrease of plasma bilirubin in Gunn rats", Science 192:892–894.**

McDuffie et al., 1988, Involvement of major histocompatibility complex products in tolerance induction in the thymus, J. Immunol. 141:1840–1847.

McHutchison et al., 1998, "Interferon alpha–2b alone or in combination with ribavirin as initial treatment for chronic hepatitis C", N. Eng. J. Med. 339:1485–1492.

Mito et al., 1993, "Hepatocyte transplantation for hepatic failure", Transplant Rev. 7:35–43.**

Mitzutani et al., 1995, "Inhibition of hepatitis C virus replication by antisense oligonucleotide in culture cells", Biochem. Biophys. Res. Commun. 212:906–911.

Mooney and Mikos, 1999, "Growing new organs", Scientific American. http://www.sciam.com:80/1999/0499issue/0499mooney.html.

Moscioni et al., 1989, "Human liver cell transplantation: prolonged function in athymic–Gunn and athymic–analbuminemic hybrid rats", Gastroenterol. 96:1546–1551.**

Mullins et al., 1996, "Perspective Series: Molecular Medicine in Genetically Engineered Animals", Journal of Clinical Investigation 98(11):537–539.

Nakajima et al., 1996, "Characterization of long–term cultures of hepatitis C virus", J. Virol. 70:3325–3329.

Ohashi et al., 2000, "Sustained survival of human hepatocytes in mice: a model for in vivo infection with human hepatitis delta viruses", Nat. Med. 6:327–331.**

Okamoto et al., 1991, "Nucleotide sequence of the genomic RNA of hepatitis C virus isolated from a human carrier: comparison with reported isolates for conserved and divergent regions" J. Gen. Viol. 72:2697–2704.

Onodera et al., 1995, "Long–term effect of intrasplenic hepatocyte transplantation in cogenitally ascorbic acid biosynthetic enzyme–deficient rats", Cell Transpl. 4:S41–S43.**

Osborn and Webber, 1982, "Immunofluorescence and immunocytochemical procedures with affinity purified antibodies: tubulin–containing structures", Meth. Cell. Biol. 24:97–132.

Ouyang et al., 1999, "A approach for obtaining functional human hepatocytes in livers of immunocompetent rats", Hepatology 30:252A.**

Pages et al., 1995, "Efficient retroviral–mediated gene transfer into primary culture of murine and human hepatocytes: expression of the LDL receptor", Hum Gene Ther. 6:21–30.**

Palmiter et al., 1982, "Differential regulation of metallothionein–thymidine kinase fusion genes in transgenic mice and their offspring", Cell 29:701–710.

Peterson et al., 1998, "Liver repopulation with xenogenic hepatocytes in B and T cell–deficient mice leads to chronic hepadnavirus infection and clonal growth of hepatocellular carcinoma", Proc. Natl. Acad. Sci. U.S.A., 95:310–315.**

Ponder et al., 1991, "Mouse hepatocytes migrate to liver parenchyma and function indefinitely after intrasplenic transplantation", Proc. Natl. Acad. Sci. U.S.A. 88:1217–1221.

Powell and Streilein, 1990, "Neonatal tolerance induction by class II alloantigens activates IL–4–secreting, tolerogen–responsive T cells", J. Immunol. 144:854–859.

Poynard et al., 1998, "Randomised trial of interferon α2b plus ribavarin for 48 weeks or 24 weeks versus interferon α2b plus placebo for 48 weeks for treatment of chronic infection with hepatitis C virus", Lancet 352:I426–I432.

Pullen et al., 1988, "The T–cell repertoire is heavily influenced by tolerance to polymorphic self–antigens", Nature 335:796–801.

Ramsdell et al., 1989, "A nondeletional mechanism of thymic self tolerance", Science 246:1038–1041.

Rhim et al., 1995, "Complete reconstitution of mouse liver with xenogenic hepatocytes", Proc. Natl. Acad. Sci. U.S.A. 92:4942–4946.**

Rhim et al., 1994, "Replacement of diseased mouse liver by hepatic cell transplantation", Science 263:1149–1152.**

Wu CH, Ouyang EC, Walton CM, Wu GY. Human hepatocytes transplanted into genetically immunocompetent rats are susceptible to infection by hepatitis B virus in situ. J Viral Hepat. Mar. 2001;8(2):111–119.

Yuh DD, Gandy KL, Reitz BA, Hoyt G, Robbins RC. Perinatal induction of immunotolerance to cardiac and pulmonary allografts. J Thorac Cardiovasc Surg. Jul. 1997;114(1):64–75.

Rivas et al., 1994, "Transplantation of hepatocytes: an in–vitro and in–vivo study in canines", Cell Tranplantation 3:193–201.

Rozga et al., 1995, "Repeated intraportal hepatocyte transplantation in analbuminemic rats", Cell Transpl. 4:237–243.

Sacci et al., 1992, "Mouse model for exoerythrocytic stages of Plasmodium falciparum malaria parasite", Proc Natl Acad Sci. 89:3701–3705.**

Salomon et al., 1995, "A truncated herpes simplex virus thymidine kinase phosphorylates thymidine and nucleoside analogs and does not cause sterility in transgenic mice", Mol. Cell. Biol. 15:5322–5328.

Sandgren et al., 1991, "Complete hepatic regeneration after somatic deletion of an albumin–plasminogen activator transgene", Cell 66:245–256.

Sanhadji et al., 1992, "Transplantation in various murine models", Bone Marrow Transplantation 9:77–82.

Santoro and Joyce, 1997, "A general purpose RNA–cleaving DNA enzyme", Proc. Natl. Acad. Sci. U.S.A. 94:4262–4266.

Scheffe, 1959, The analysis of variance, John Wiley and Sons, New York, NY, p. 247.

Seeger et al., 1986, "Biochemical and genetic evidence for the hepatitis B virus replication strategy", Science 232:477–484.

Seglen et al., 1976, "Preparation of rat liver cells", Methods Cell Biol. 13:29.

Sells et al., 1988, "Replicative intermediates of hepatitis B virus in HepG2 cells that produce infectious virions", J. Virol. 62:2836–2844.

Shimizu and Yoshikura, 1994, "Multicycle infection of hepatitis C virus in cell culture and inhibition by alpha and beta interferons", 68:8406–8408.

Shimizu et al., 1992, "Evidence for in vitro replication of hepatitis C virus genome in a human T–cell line", Proc. Natl. Acad. Sci. U.S.A., 89:5477–5481.

Smythe et al., 1995, "Treatment of experimental human mesothelioma using adenovirus transfer of the herpes simplex thymidine kinase gene", Ann. Surg. 222:78–86.

Sommer et al., 1979, "Hepatocellular transplantation for treatment of D–galactosamine–induced acute liver failure in rats", Transplant Proc. 11:578–584.**

Soriano et al., 1992, "Retroviral transduction of human hepatocytes and orthotopic engraftment in SCID mice after hepatocellular transplantation", Transplant Proc. 24(6):3020–3021.**

Streilein, 1991, "Neonatal tolerance of H–2 alloantigens: procuring graft acceptance the 'old–fashioned' way", Transplantation 52:1–10.

Su et al., 1996, "Selective killing of AFP–positive hepatocellular carcinoma cells by adeno–associated virus transfer of the herpes simplex virus thymidine kinase gene", Human Gene Therapy, 7:463–470.**

Sugiyama et al., 1997, "Genetic analysis of the hepatitis C virus (HCV) genome from HCV–infected human T cells", J. Gen. Virol. 78:329–336.

Summers and Mason, 1982, Replication of the genome of a hepatitis B–like virus by reverse transcription of an RNA intermediate, Cell 29:403–415.

Sutherland et al., 1977, "Hepatic transplantation in acute liver failure", Surgery 82:124–132.**

Takamizawa et al., 1991, "Structure and organization of the hepatitis C virus genome isolated from human carriers", J. Virol. 65:1105–1113.

Takeshita et al., 1993, "Hepatocellular transplantation for metabolic support in experimental acute ischemic liver failure in rats", Cell Transplantation 2:319–324.**

Taylor et al., 1999, "Inhibition of interferon–inducible protein kinase PKR by HCV E2 protein", Science 285:107–110.

Thomas, 1999, "Hepatitis C virus dynamics in vivo and the antiviral efficacy of interferon alfa therapy", Hepatology 29:1333–1334.

Touraine, 1991, "In utero transplantation of fetal liver stem cells in humans", Blood Cells 17:379–387.

Vemura et al., 1992, "Immune tolerance to a defined heterologous antigen after intrasplenic hepatocyte transplantation: implications for gene therapy", FASEB 6:2836–2842.

Verma and Somia, 1997, "Gene therapy—promises, problems and prospects", Nature. 389:239–242.**

Wiederkehr et al., 1990, "Hepatocyte transplantation for the low–density lipoprotein receptor–deficient state" Transplant. 50:466–476.**

Will et al., 1987, "Replication strategy of human hepatitis B virus", J. Virol. 61:904–911.

Willems et al., 1994, "Hepatitis virus C–RNAs in plasma and in peripherial blood mononuclear cells of hemophiliacs with chronic hepatitis C", J. Med. Virol. 42:272–278.

Wilson et al., 1992, "Hepatocyte–directed gene transfer in vivo leads to transient improvement of hypercholesterolemia in low density lipoprotein receptor–deficient rabbits", J. Biol. Chem. 267:963–967.

Wilson et al., 1991, "Transplanation of allogenic hepatocytes into LDL receptor deficient rabbits leads to transient improvement in hypercholesterolemia", Clin. Biotechnol. 3:21–26.

Wu et al., 1991, "Receptor–mediated gene delivery in vivo: partial correction of genetic analbuminemia in nasage rats", J. Biol. Chem. 266:14338–14342.

Yoo et al., 1995, "Transfection of a differentiated human hepatoma cell line (Huh 7) with in vitro–transcribed hepatitis C virus (HCV) RNA and establishment of a long–term culture persistently infected with HCV", J. Gen. Virol. 69:32–38.

Yuh et al., 1997, "A rodent model of in utero chimeric tolerance induction", J. Heart Lung Transpl. 16:222–230.

Yuh et al., 1992, "Transcriptional regulation of precore and pregenomic RNAs of hepatitis B virus" J. Virol. 66:4073–4084.

Zignego et al., 1992, "Infection of peripheral mononuclear blood cells by hepatitis C virus", J. Hepatology 15:382–386.

Zucker, 1989, "On finding all suboptimal foldings of an RNA molecule", Science 244:48–52.

* cited by examiner 68,000 —

1: 10 ng standard human albumin
2: 10 ng standard rat albumin
3: 2 days
4: 2 weeks
5: 3 weeks
6: 5 weeks
7: 6 weeks Time course of human albumin and HBV expression Anti Human Albumin Anti Hepatitis B Surface Antigen 1 week 6 weeks 14 weeks Anti Human Albumin Anti Hepatitis B Surface Antigen Rat CA2

Hepatocytes
Plus HBV

Rat CA3

Hepatocytes
alone

10μm

Rat CA5

HBV alone

Rat CA2 minus primary Ab

RT-PCR Human Albumin RNA

RT-PCR HBV RNA

1: 1 kbp ladder
2: Rat liver RNA
3: Human liver RNA
4: HepG2.2.14 RNA
5: Rat CA2 – Human hepatocytes + HBV, 1 week post
6: Rat CA2 – 6 weeks post
7: Rat CA2 – 14 weeks post Hepatocytes plus HBV 1 week Hepatocytes plus HBV 6 weeks Hepatocytes plus HBV 14 weeks Day 1

X125

X250

X125

X250

Day 7

X125

X250

Human Albumin

Tolerized
with T3
no trans-
plantation

BrdU

Tolerized
with T3
no trans-
plantation

Human Albumin

Tolerized
with T3
and trans-
plantation

BrdU

Tolerized
with T3
and trans-
plantation

Human Albumin

25μm

Control
no T3
no trans-
plantation

BrdU

Control
no T3
no trans-
plantation

SEQUENCE LISTING

<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Oligonucleotide probe

<400> SEQUENCE: 1
tgtgcttatg tagccatcca gcgagtcccc                             30

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 2
tcgcgaccca acactactc                                         19

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 3
gggggcgaca ctccacca                                          18

```
<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 4
ccttggtgtt gattgccttt gctc                                              24

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 5
catcacatca acctctgtct gacc                                              24

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 6
atagtgtccc agaaagctgg taggg                                             25

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 7
cggtttaagg acttaggaga acagc                                             25

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 8
atcttctgcg acgcggcgat ggagatc                                           27

<210> SEQ ID NO 9
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 9
ctctgctggg gggaattgat gactctagc                                         29

<210> SEQ ID NO 10
<211> LENGTH: 25
<212> TYPE: DNA
<213> ORGANISM: Artificial Sequence
<220> FEATURE:
```

-continued

```
<223> OTHER INFORMATION: Oligonucleotide primer

<400> SEQUENCE: 10
gccggtctgg agcaaagctc atcgg                                        25

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 11
ggcggtgtct aggagatctc tgac                                         24

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 12
ctggtctcac caatcggg                                                18

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 13
ctggtctcac caatcggggg                                              20
```

PROPAGATION OF HUMAN HEPATOCYTES IN NON-HUMAN ANIMALS

This patent application is a continuation-in-part of International Patent Application No. PCT/US00/05713 filed Mar. 3, 2000 and published in English, which claims priority as a continuation-in-part of U.S. patent application Ser. No. 09/431,901 filed Nov. 2, 1999, now U.S. Pat. No. 6,525,242.

The subject matter herein was generated at least in part under National Institute of Diabetes and Digestive and Kidney Diseases ("NIDDK") Grant No. DK-42182, such that the United States Government has certain rights herein.

1. INTRODUCTION

The present invention relates to the propagation of human hepatocytes in the livers of non-human animals that have been tolerized to the human cells. Such animals provide an in vivo model system of the human liver that may be used in toxicology assays and in the study of human liver diseases, including the various forms of hepatitis (in particular hepatitis B and C) and alcohol-induced liver degeneration. They may also be used as a source of human hepatocytes for reconstitution of liver tissue, thereby providing an alternative to liver transplantation.

2. BACKGROUND OF THE INVENTION

2.1. The Need for a Culture System for Human Hepatocytes

To accurately study the physiology of human liver cells (hepatocytes), scientists need a model system in which the hepatocytes exist as they would in the intact liver. Such systems have proven to be difficult to achieve, because when hepatocytes are removed from their native environment, they tend to lose their specialized functions, or "dedifferentiate". The loss of liver-specific functions makes it difficult or impossible to study the normal functions of hepatocytes as well as their response to chemical or biological agents. For example, research directed toward infectious diseases of the liver, in particular viral hepatitis, has been hampered by the lack of an adequate model system. Hepatitis B and hepatitis C, and the problems that have been encountered by scientists studying these infectious and dangerous viruses, are discussed in the following subsections.

In addition, a system for propagating human hepatocytes could be used to provide cells that could be used as an alternative or adjunct to liver transplant. Currently, patients suffering from liver disease may have to wait for long periods of time before a suitable organ for transplant becomes available. After transplant, patients need to be treated with immunosuppressive agents for the duration of their lives in order to avoid rejection of the donor's liver. A method for propagating the patient's own cells could provide a source of functional liver tissue which would not require immunosuppression to remain viable.

2.2 Hepatitis B Virus

Hepatitis B virus ("HBV") is the prototype of the Hepadnaviridae, characterized by a unique genome structure comprising partially double-stranded DNA (*Fields Virology*, 1996, Third Edition, Fields, et al. eds., Lippincott-Raven, New York, pp. 2741–2742). In the United States, there are about a million carriers of HBV, and the number of carriers in the world exceeds 350 million (*Fields Virology*, p. 2741; Petersen et al., 1998, Proc. Natl. Acad. Sci. U.S.A. 95:310–315). In addition to causing an acute hepatitis, viral infection may lead to chronic infection and consequent liver failure and/or the development of hepatocellular carcinoma (*Fields Virology*, pp. 2748–2751).

One of the major problems in the study of human viral hepatitis is the lack of convenient laboratory models of the disease. The narrow host specificity of the viruses limits current infection models to high primates (Caselmann, 1994, Antiviral Res. 24:121–129). Although HBV—expressing immortalized human hepatocytes (in the form of isolated cells; Brown et al., 2000, Hepatology 31:173–181) and human liver fragments previously infected with hepatitis B virus (HBV) have been transplanted into immunodeficient rodent hosts (Ilan et al., 1999, Hepatology 29:553–562), and have been shown to continue to produce virus, it has not been shown whether normal human hepatocytes can remain sufficiently differentiated in a foreign host to be susceptible to infection by HBV. Among the murine models recently developed are a transgenic mouse model and a "Trimera", reported in Petersen et al., 1998, Proc. Natl. Acad. Sci. U.S.A. 95:310–315 and Ilan et al., 1999, Hepatology 29:553–562, respectively.

In the transgenic mouse model of Petersen et al., a transgene encoding a hepatotoxic urokinase-type plasminogen activator was introduced into RAG-2 knockout mice, which lack mature B and T lymphocytes, and then woodchuck hepatocytes were introduced via splenic injection. The woodchuck hepatocytes replaced up to 90 percent of the mouse liver, and supported woodchuck hepatitis virus (another hepadnavirus) replication indefinitely. The replication of the virus responded to pharmacologic agents.

In the Trimera model described by Ilan et al., normal mice were preconditioned by lethal total body radiation, radioprotected with SCID mouse bone marrow cells, and then engrafted with human liver fragments infected ex vivo with hepatitis B.

2.3. Hipatitis C Virus

Hepatitis C virus was first characterized in 1989 (Choo et al., 1989, Science 244: 359–362), but its existence had been posited for many years as an elusive entity that caused flu-like symptoms in certain patients who had received blood transfusions. Because these symptoms were sometimes followed, years later, by liver disease, the clinical syndrome was referred to as non A-non B hepatitis ("NANBH").

Hepatitis C virus ("HCV") is now known to be a member of the Flaviviridae family of viruses, which includes viruses that cause bovine diarrhea, hog cholera, yellow fever, and tick-borne encephalitis (Kato et al., 1990, Proc. Natl. Acad. Sci. U.S.A. 87: 9524–9528; Choo et al., 1991, Proc. Natl. Acad. Sci. U.S.A. 88: 2451–2455; Okamoto et al., 1991, J. Gen. Virol. 72: 2697–2704; Takamizawa et al., 1991, J. Virol. 65: 1105–1113). The viral genome consists of an approximately 9.5 kb single-stranded, positive-sense RNA molecule characterized by a unique open reading frame coding for a single polyprotein (reviewed in Clarke, 1997, J. Gen. Virol 78: 2397–2410 and Major and Feinstone, 1997, Hepatology 25: 1527–1538). Based upon phylogenetic analysis of the core, EI, and NS5 regions, HCV has been found to be genetically heterogeneous, with at least six genotypes and more than 30 subtypes dispersed throughout the world (Major and Feinstone, 1997, Hepatology 25: 1527–1538; Clarke, 1997, J. Genl. Virol 78: 2397–2410).

HCV has been estimated to infect 170 million people worldwide, which is more than four times the number of persons infected with human immunodeficiency virus ("HIV"), and the number of HCV-associated deaths may eventually overtake deaths caused by AIDS (Cohen, 1999, Science 285: 26–30). The Center for Disease Control has calculated that HCV may be harbored by 1.8 percent of the U.S. population. (Id.). The only available therapy is interferon, but most HCV isolates are resistant (Thomas et al., 1999, Hepatology 29: 1333), although more promising results were obtained when interferon was combined with ribavirin (Cohen et al., 1999, Science 285: 26–30 citing Poynard et al., 1998, Lancet 352:1426–1432 and Davis et al., 1998, N. Engl. J. Med. 339:1493–1499). Unfortunately, the interferon/ribavirin combination is less effective against the most common HCV genotype found in the U.S., with only 28 percent of persons infected with that genotype exhibiting a sustained response to treatment (Davis et al., 1998, N. Engl. J. Med. 339:1493–1499).

The development of more successful forms of therapy (and our understanding of HCV biology) has been hampered by the absence of a good model system for HCV infection. Only humans and certain higher primates are susceptible to infection (Feinstone et al., 1981, J. Infect. Dis. 144: 588). A variety of mammalian cell systems which support the growth of HCV have been reported which rely on the use of strand-specific RT-PCR as evidence of virus replication (Major and Feinstone, 1997, Hepatology 25:1527–1538 citing Mitzutani et al., 1995, Biochem. Biophys. Res. Commun. 212: 906–911; Shimizu and Yoshikura, 1994, 68: 8406–8408; Kato et al., 1995, Biochem. Biophys. Res. Commun. 206: 863–869; Cribier et al., 1995, J. Gen. Virol. 76: 2485–2491; and Yoo et al., 1995, J. Virol. 69: 32–38).

As reviewed in Clarke (supra), there have been reports of viral replication in systems based on hepatic tissue (Ito, et al., 1996, J. Gen. Virol. 77: 1043–1054), peripheral blood mononuclear cells (Willems et al., 1996, J. Med. Virol. 42: 272–278; Zignego et al., 1992, J. Hepatology 15: 382–386), human T and B cell lines (Bertolini et al., 1993, Res. Virol 144: 281–285; Shimizu et al., 1992, Proc. Natl. Acad. Sci. U.S.A. 89: 5477–5481), human fetal liver cells (Iacovacci et al., 1993, Res. Virol. 144: 275–279), chimpanzee hepatocytes (Lanford et al., 1994, Virol. 202: 606–614), Daudi B-cells (Nakajima et al., 1996, J. Virol. 70: 3325–3329), and the human T cell leukemia virus type I-infected T cell line MT-Z (Mitzutani et al., 1995, Biochem. Biophys. Res. Comm. 212: 906–911; Sugiyama et al., 1997, J. Gen. Virol. 78: 329–336). None of these systems has, however, proved satisfactory.

Hepatitis C-infected human liver tissue was transplanted into Trimera mice described in the preceding section, as reported by Galun et al., 1995, J. Infect. Dis. 172:25–30.

A newer system was recently reported by Lohmann et al. (1999, Science 285:110–113) in which subgenomic HCV RNA replicons were transfected into a human hepatoma cell line and found to replicate to high levels. Nonetheless, this system does not generate virus and therefore is not a model of productive infection (Cohen, supra).

2.3. Hepatocytes for Liver Reconstitution

Reconstitution of liver tissue in a patient by the introduction of hepatocytes (also referred to as "hepatocyte transplantation") is a potential therapeutic option for patients with acute liver failure, either as a temporary treatment in anticipation of liver transplant or as a definitive treatment for patients with isolated metabolic deficiencies (Bumgardner et al., 1998, Transplantation 65: 53–61). Animal models have been developed for studying the effectiveness of hepatocyte transplantation in the context of pharmacologically or surgically induced liver failure (Id, citing Mito et al., 1993, Transplant Rev. 7: 35; Takeshita et al. 1993, Cell Transplant 2: 319; Sutherland et al., 1977, Surgery 82: 124; Sommer et al., 1979, Transplant Proc. 9: 578; and Demetriou et al., 1988, Hepatology 8: 1006), or for the treatment of isolated errors of metabolism (Wiederkehr et al., 1990, Transplant 50: 466; Onodera et al., 1995, Cell Transpl. 4 (Supp. 1): 541; Cobourn et al., 1987, Transpl. Proc. 19: 1002; Rozga et al., 1995, Cell Transplant 4: 237; Kay et al., 1994, Hepatology 20: 253; Matas et al., 1976, Science 192: 892; Holzman et al., 1993, Transplantation 55: 1213; Moscioni et al., 1989, Gastroenterol. 96: 1546; Groth et al., 1977, Transplant Proc. 9: 313). Use of transfected hepatocytes in gene therapy of a patient suffering from familial hypercholesterolemia has been reported in Grossman et al., 1994, Nat. Genet. 6: 335.

A major obstacle to achieving therapeutic liver reconstitution is immune rejection of transplanted hepatocytes by the host, a phenomenon referred to (where the host and donor cells are genetically and phenotypically different) as "allograft rejection". Immunosuppressive agents have been only partially successful in preventing allograft rejection (Javregui et al., 1996, Cell Transplantation 5: 353–367, citing Darby et al., 1986, Br. J. Exp. Pathol. 67: 329–339; Maganto et al., 1988, Eur. Surg. Res. 20: 248–253; Makowka et al., 1986, Transplantation 42: 537–541). The three main alternative approaches which have been explored are 1) physically shielding transplanted cells from the host immune system, for example, in an alginate-polylysine or chitosan capsule; 2) depletion of antigen presenting cells; or 3) induction of alloantigen-specific tolerance in the host (Javregui et al., supra). Chowdhury has tested the hypothesis that intrathymic injection of donor rat splenocytes may result in suppression of allograft hepatocyte rejection in peripheral lymphocyte depleted adult rats (Jauregui et al., supra, citing Fabrega et al., 1995, Transplantation 59: 1362–1364). In that study, long-term tolerization occurred with administration of splenocytes but not hepatocytes.

For successful reconstitution, the age of the donor cells has been considered significant. Cusick et al. (1997, J. Ped. Surg. 32: 357–360) report that transplanted fetal hepatocytes had a significant survival advantage over adult hepatocytes, independent of recipient age. However, Rhim et al. (1994, Science 263: 1149–1152) demonstrated that adult mouse liver cells could proliferate when introduced into the livers of congenic transgenic mice carrying a hepatotoxic transgene (urokinase under the control of the albumin promoter, which is liver-specific and only active postnatally). The donor cells were observed to have divided at least 12 times (reconstitution of an entire liver from one hepatocyte would require 28 cell doublings). Other references relating to liver repopulation in immunologically deficient animals with transplanted hepatocytes include Gupta et al., 1996, Prog. Liv Dis. 14:199–222; Sandgren et al., 1991, Cell 66:245–256; and Rhim et al., 1995, Proc. Natl. Acad. Sci. U.S.A. 92: 4942–4946.

3. SUMMARY OF THE INVENTION

The present invention relates to the preparation of tolerized non-human animals having chimeric livers, wherein some or a majority of the hepatocytes present are human hepatocytes. It is based, at least in part, on the discovery that rats, tolerized in utero against human hepatocytes, were found to serve as long-term hosts for human hepatocytes introduced postnatally, and that the introduced hepatocytes maintained their differentiated phenotype, as evidenced by continued production of human albumin.

In a first embodiment, the present invention provides for a method of preparing a non-human animal having a liver comprising human hepatocytes, comprising (i) inducing tolerance in an immunocompetent host non-human animal, where the animal is preferably a fetus or a neonate (i.e., perinatally); and (ii) introducing human hepatocytes into the tolerized animal, preferably postnatally and preferably by intra-splenic injection. In specific non-limiting embodiments, the host animal is subjected to a selection pressure which favors survival and/or proliferation of human, rather than host animal, hepatocytes.

In a second embodiment of the invention, an animal having a chimeric liver, prepared as described above, may be used as a model system for human hepatocyte function in a toxicology study. Because the human hepatocytes maintain their differentiated state and are situated in their natural anatomic location, this model system recapitulates the metabolic fate of test agents as they pass from the site of administration through the liver.

In a third embodiment of the invention, an animal having a chimeric liver may be used as a model system for human liver disease. Such model systems are particularly useful for diseases which specifically affect human (or primate), but not non-human (or non-primate) livers, such as hepatitis B and hepatitis C infection and alcohol-induced liver degeneration/fibrosis. Immunocompetent chimeric animals of the invention exhibit the further advantage of having an immune system which is intact but for exhibiting tolerance toward the human cells comprised in the animal's liver.

In a fourth embodiment of the invention, an animal having a chimeric liver may be used as a source of human hepatocytes which may be used therapeutically. As non-limiting examples, such human hepatocytes may be used in gene therapy applications or to reconstitute liver tissue in a human host whose own liver has been substantially damaged. Large animals having a chimeric liver may be particularly desirable for such embodiments.

4. DESCRIPTION OF THE FIGURES

FIG. 1. $^3$[H]-thymidine incorporation in mixed lymphocyte assays where the responder cells were rat spleen cells and the stimulator cells were irradiated human hepatocytes. "Spleen (iu)" designates spleen cells from rats tolerized by transuterine injection of human hepatocyte lysates, and "spleen (iu/is)" designates spleen cells from rats tolerized as fetuses with human hepatocyte lysates followed by intrasplenic transplantation of human hepatocytes after birth.

Figure 2:
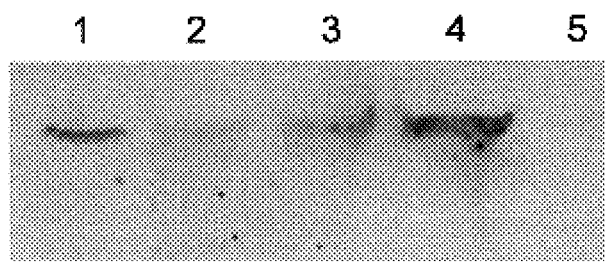

FIG. 2. Western blot, using anti-human albumin antibody as a probe, of human serum albumin (lane 1), serum from a tolerized rat six weeks after intrasplenic injection (lane 2), and sera from a tolerized rat, injected with human hepatocytes, 24 hours (lane 3), and eight days (lane 4) after a second injection of human hepatocytes. Lane 5 contains serum from a non-tolerized rat eight days after a second injection of human hepatocytes.

Figure 3:
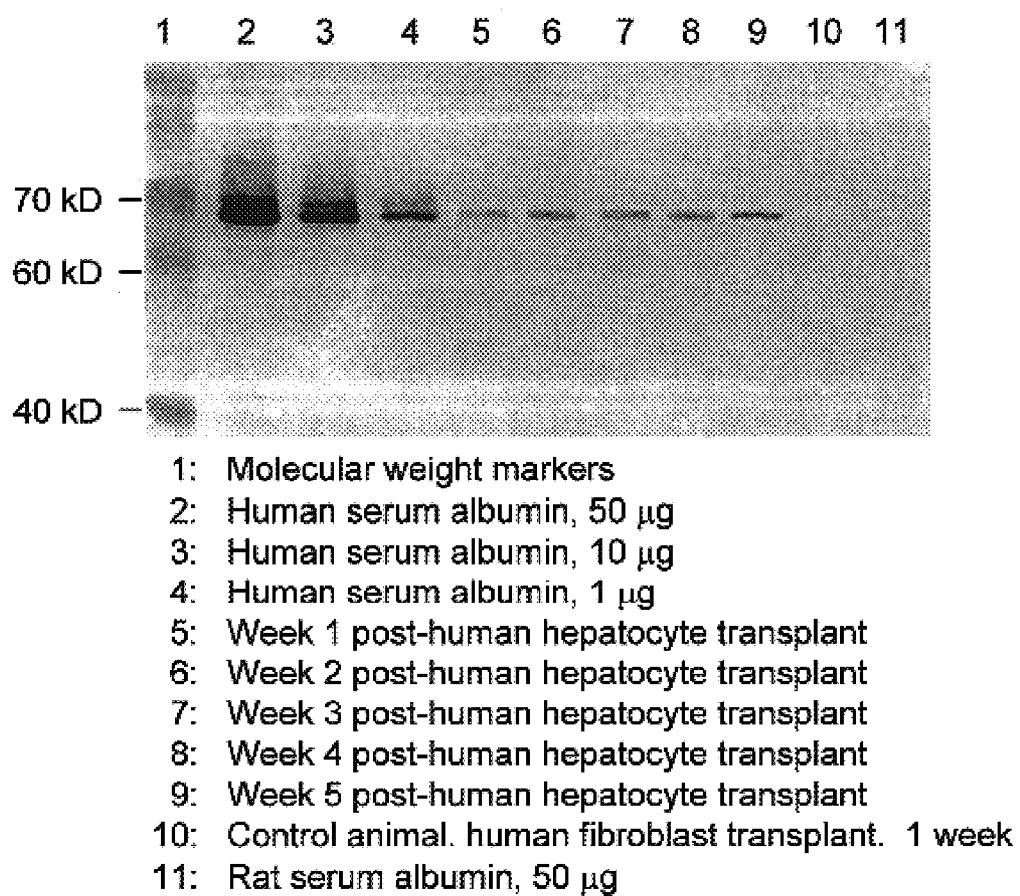

FIG. 3. Western blot, using anti-human albumin antibody as a probe, of human serum albumin (lanes 2–4), serum from a tolerized rat that had received an intrasplenic injection of human hepatocytes, one week (lane 5), two weeks (lane 6), three weeks (lane 7), four weeks (lane 8) and five weeks (lane 9) after injection with human hepatocytes. Serum from control animal tolerized and transplanted with human lung fibroblast (lane 10) and rat serum albumin (lane 11).

FIGS. 4A–D. Immunofluorescence studies using antihuman albumin as primary antibody and fluorescent Texas red-coupled secondary antibody. (A) Anti-human albumin antibody binding to control (non-chimeric) rat liver; (B) anti-human albumin antibody binding to chimeric rat liver three weeks after injection with human hepatocytes; (C) same as B, without secondary antibody visualization; and (D) anti-human albumin antibody binding to the liver of a rat that had been tolerized with a human hepatocyte lysate but did not receive subsequent injection of viable liver cells.

Figure 4A:
Figure 4B:
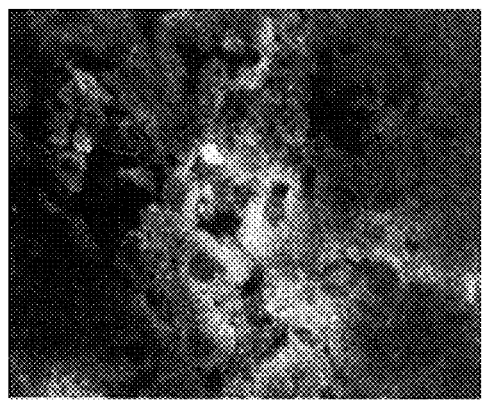
Figure 4C:
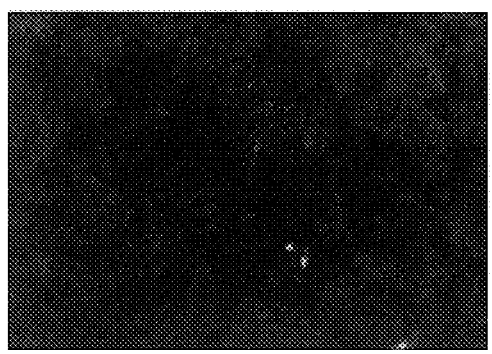
Figure 4D:
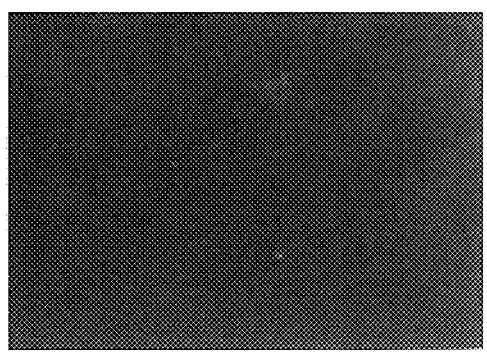
Figure 5:
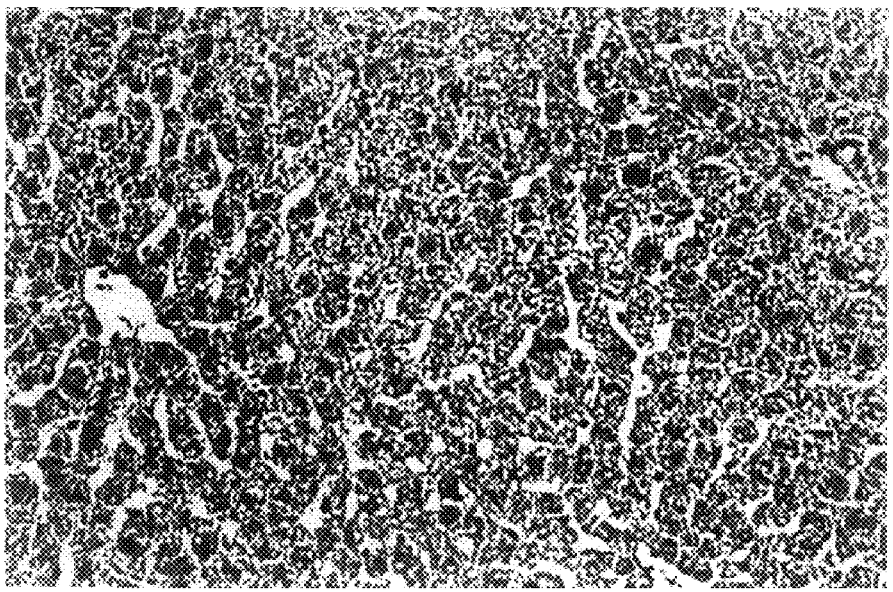
Figure 6A:
Figure 6B:
Figure 6C:
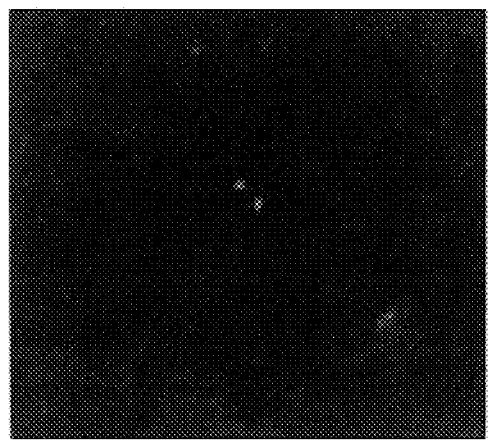
Figure 6D:
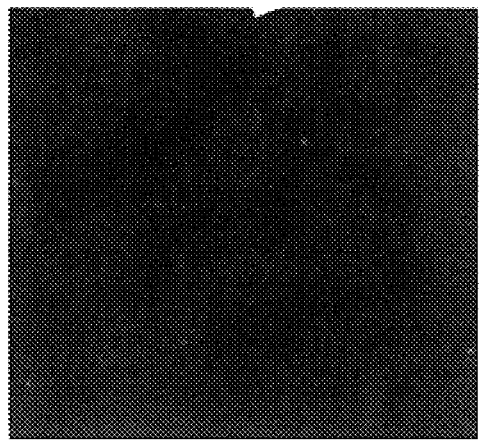

FIG. 5. The same section of chimeric rat liver shown in FIG. 4B to express human albumin, stained with hematoxylin and eosin to demonstrate normal histology.

FIGS. 6A–D. Immunofluorescence studies using primary and secondary antibodies as in FIGS. 4A–D, showing (A) a section of liver from a tolerized rat six weeks after intrasplenic injection with human hepatocytes, stained with both antibodies; (B) as in (A), but without secondary antibody staining; (C) as in (A), but with no antibody binding; and (D) a section of liver from a non-tolerized rat, six weeks after intrasplenic injection of human hepatocytes, stained with both antibodies.

Figure 7:

FIG. 7. Western blot, using anti-human albumin antibody as a probe, of human serum albumin (lane 1), rat serum (lane 2) and sera from a chimeric rat which had been tolerized by intrathymic injection of human hepatocytes, at various times after intrasplenic injection with human hepatocytes (lane 3=2 days, lane 4=2 weeks, lane 5=3 weeks, lane 6=5 weeks, lane 7=6 weeks).

FIGS. 8A–F. Immunofluorescence studies of liver sections from tolerized rats injected with human hepatocytes and inoculated with hepatitis B virus (HBV) at 1 week, 6 weeks, and 14 weeks following inoculation, stained with anti-albumin primary and Texas red conjugated secondary antibody (FIGS. 8A, 8C and 8E, for weeks 1, 6 and 14, respectively) or anti-hepatitis B surface antigen (HBsAg) antibody and FITC-conjugated secondary antibody (FIGS. 8B, 8D, and 8F for weeks 1, 6 and 14, respectively).

Figure 9A:
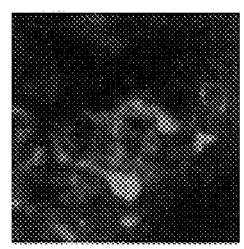
Figure 9B:
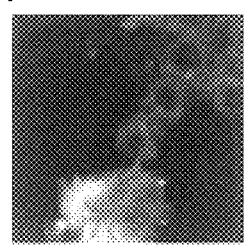
Figure 9C:
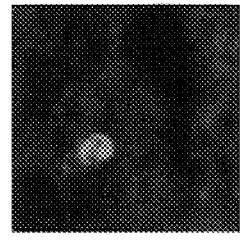
Figure 9D:
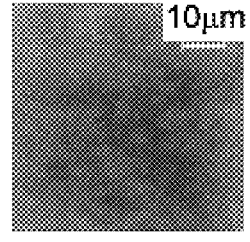
Figure 9E:
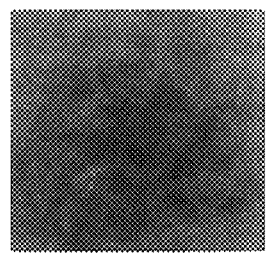
Figure 9F:
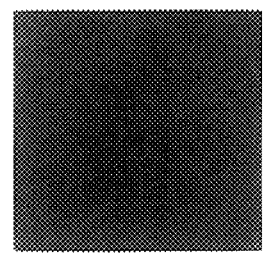
Figure 9G:
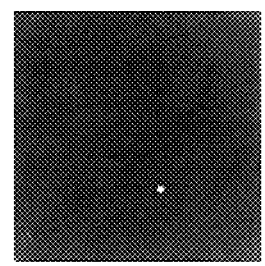
Figure 9H:
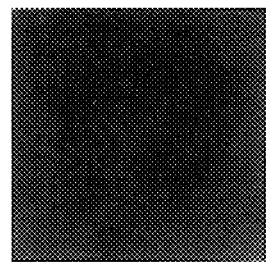

FIGS. 9A–H. Immunofluorescence studies of liver sections from rats that were either (i) tolerized, injected with human hepatocytes, and inoculated with HBV (CA2)(FIGS. 9A and 9B); (ii) tolerized and injected with human hepatocytes but not inoculated (CA3) (FIGS. 9C and 9D); (iii) tolerized and inoculated with HBV, without injection of human hepatocytes (CA5) (FIGS. 9E and 9F); or tolerized, injected with human hepatocytes and inoculated with HBV (CA2) but not reacted with primary anti-albumin or anti-HBsAg antibodies (FIGS. 9G and 9H). Sections were stained with anti-albumin primary and Texas red conjugated secondary antibody (FIGS. 9A, 9C, 9E, and 9G) or anti-HBsAg antibody and FITC-conjugated secondary antibody (FIGS. 9B, 9D, 9F, and 9H).

Figure 10:
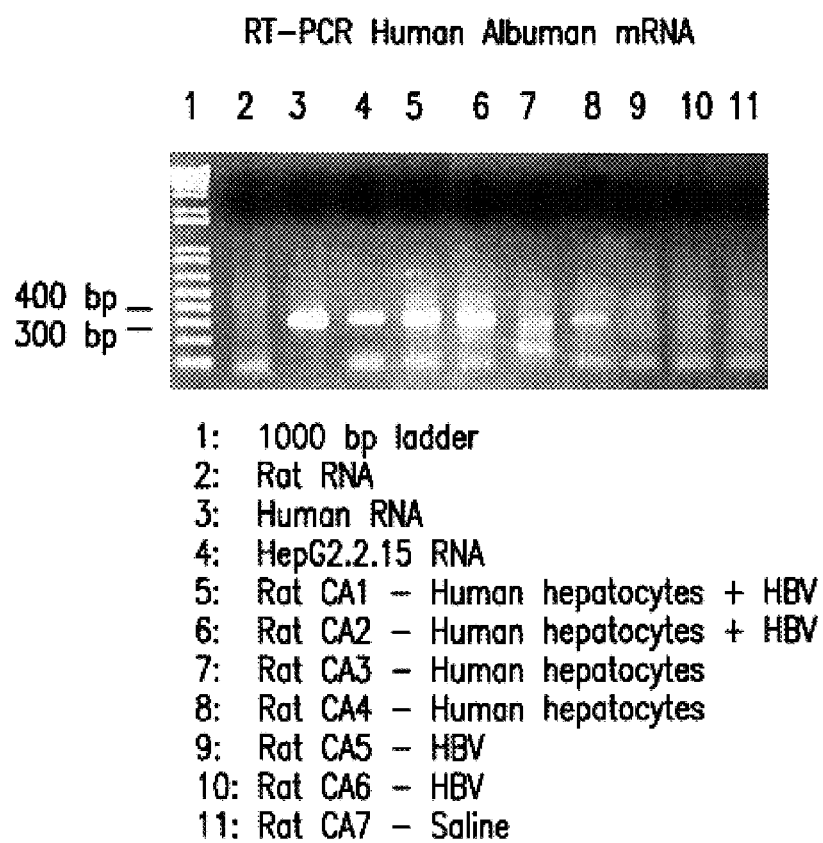

FIG. 10. Photograph of an ethidium bromide stained gel of products of reverse transcriptase-polymerase chain reaction ("RT-PCR") of human albumin mRNA, the lanes containing the RT-PCR products resulting from experiments using, as template, RNA from livers of: lane 2=rat; lane 3=human; lane 4=HepG2 2.2.15; lane 5=Rat CA1 (tolerized, injected with human hepatocytes, subsequently inoculated with HBV); lane 6=Rat CA2 (tolerized, injected with human hepatocytes, subsequently inoculated with HBV); lane 7=rat CA3 (tolerized and injected with human hepatocytes but not inoculated with HBV); lane 8=rat CA4 (tolerized and injected with human hepatocytes but not inoculated with HBV); lane 9=(tolerized and inoculated with HBV, without injection of human hepatocytes); lane 10=(tolerized and inoculated with HBV, without injection of human hepatocytes); lane 11=rat CA7 (treated with saline, negative control); and where lane 1=1,000 bp ladder.

Figure 11A:
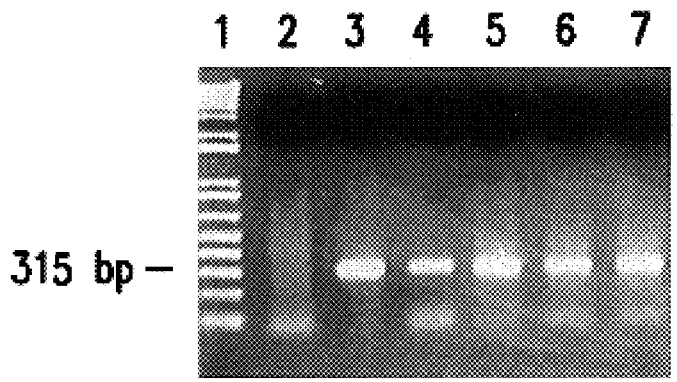
Figure 11B:
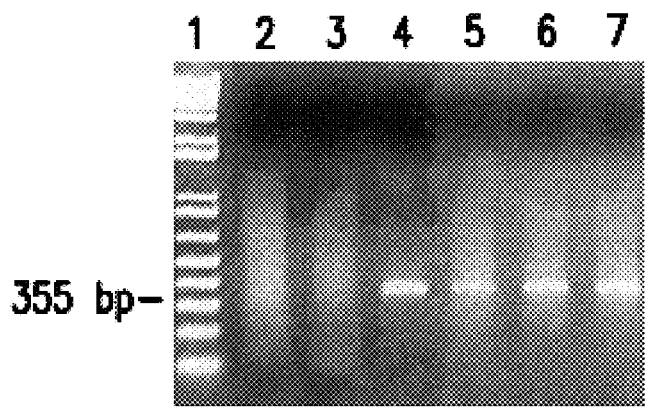

FIGS. 11A–B. Photograph of an ethidium bromide stained gel of products of RT-PCR of human albumin mRNA (FIG. 11A) and HBV RNA (FIG. 11B), the lanes containing the RT-PCR products resulting from experiments using, as template, RNA from: lane 2=rat liver; lane 3=human liver; lane 4=HepG2 2.2.15; lane 5=rat liver from CA2 (tolerized, injected with human hepatocytes, inoculated with HBV) 1 week post-inoculation; lane 6=rat liver from CA2 6 weeks post-inoculation; lane 7=rat liver from CA2 14 weeks post-inoculation, where lane 1=1,000 bp ladder.

Figure 12:
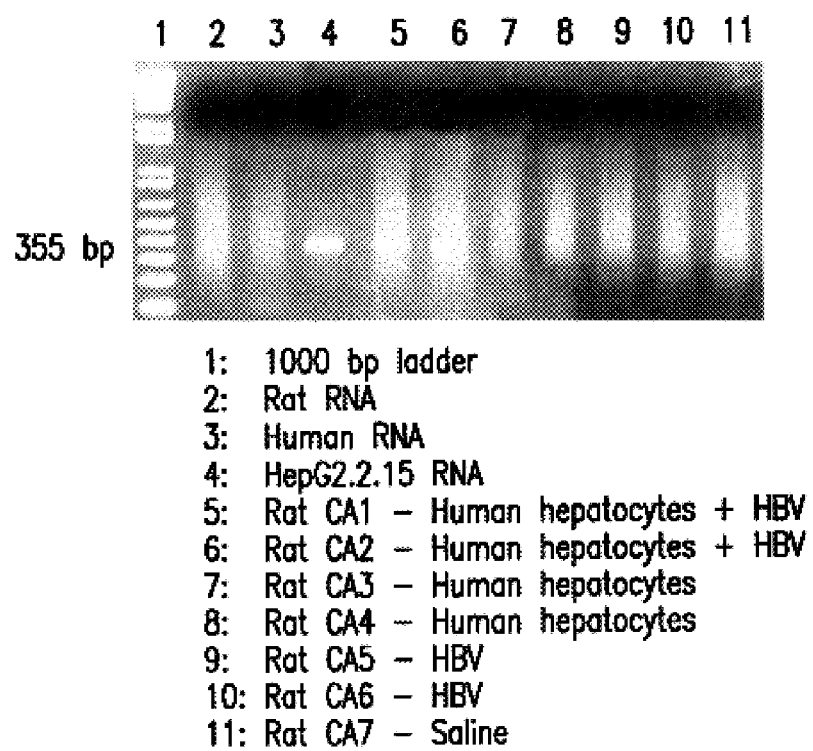

FIG. 12. Photograph of an ethidium bromide stained gel of products of RT-PCR of human hepatitis B viral RNA, the lanes containing RT-PCR products resulting from experiments using, as template, RNA from: lane 2=rat liver; lane 3=human liver; lane 4=HepG2 2.2.15; lane 5=rat liver from CA1 (tolerized, injected with human hepatocytes and inoculated with HBV); lane 6=rat liver from CA2 (tolerized, injected with human hepatocytes, inoculated with HBV); lane 7=rat liver from CA3 (tolerized with human hepatocytes but not inoculated with HBV); lane 8=rat liver from CA4 (tolerized with human hepatocytes but not inoculated with HBV); lane 9=rat liver from CA5 (tolerized with human hepatocytes, not injected with human hepatocytes, inoculated with HBV); lane 10=rat liver from CA6 (tolerized with human hepatocytes, not injected with human hepatocytes, inoculated with HBV); where lane 1=1,000 bp ladder.

Figure 13A:
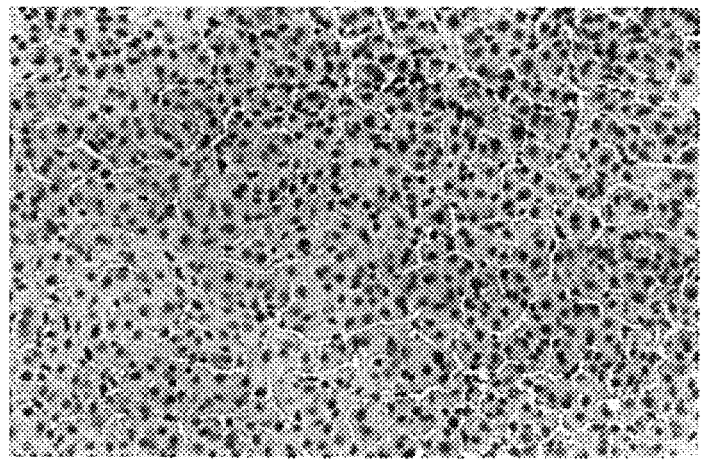
Figure 13B:
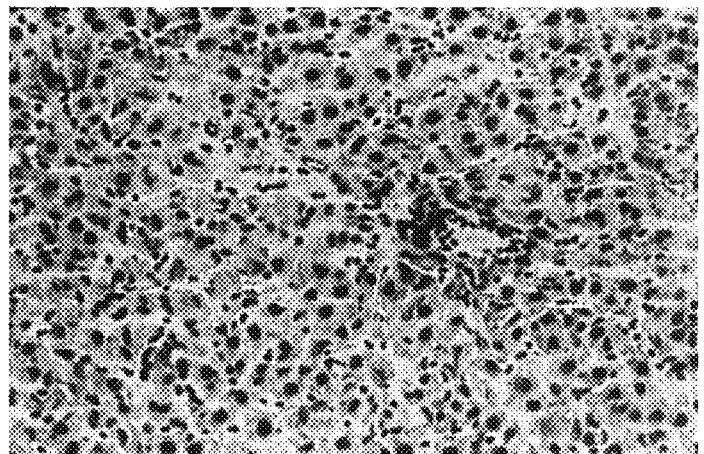
Figure 13C:
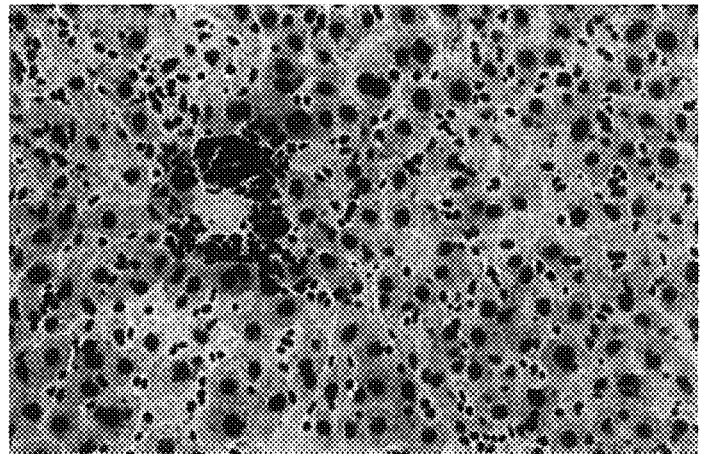

FIGS. 13A–C. Photomicrographs of hematoxylin-eosin stained liver sections, at low (20×) magnification, of liver sections from a rat tolerized, transplanted with human hepatocytes, and inoculated with HBV, (13A) 1 week, (13B) 6 weeks, or (13C) 14 weeks post-inoculation.

Figure 14A:
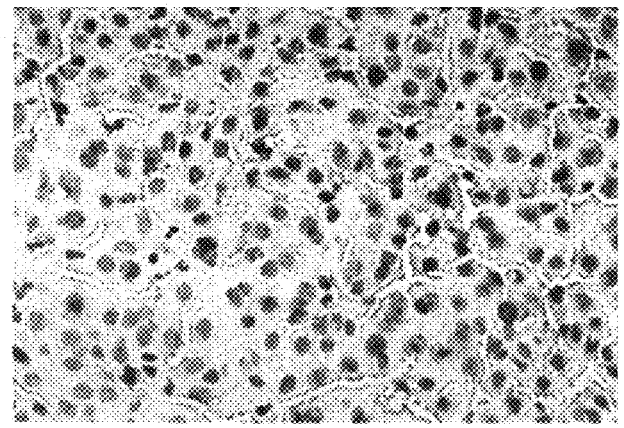
Figure 14B:
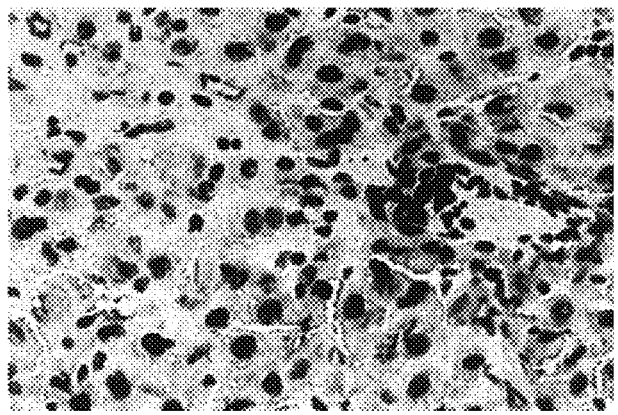
Figure 14C:
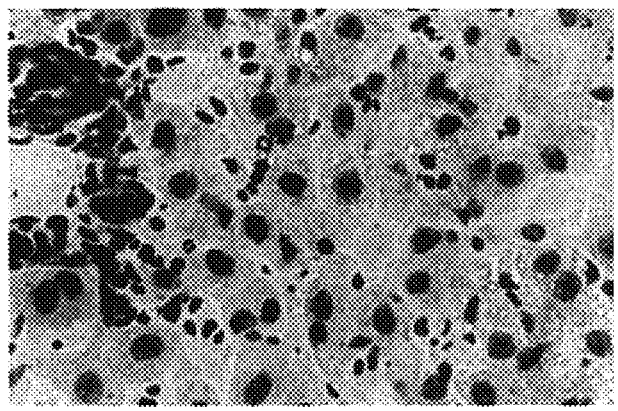

FIGS. 14A–C. Photomicrographs of hematoxylin-eosin stained liver sections, at high (40×) magnification, of liver sections from a rat tolerized, transplanted with human hepatocytes, and inoculated with HBV, (13A) 1 week, (13B) 6 weeks, or (13C) 14 weeks post-inoculation.

Figure 15:
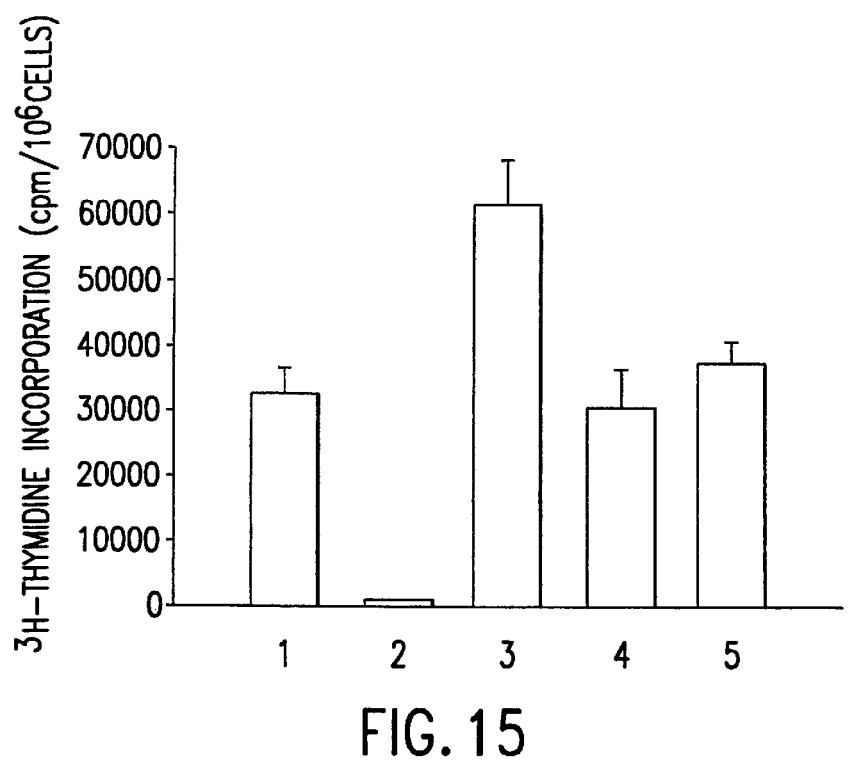
Figure 16A:
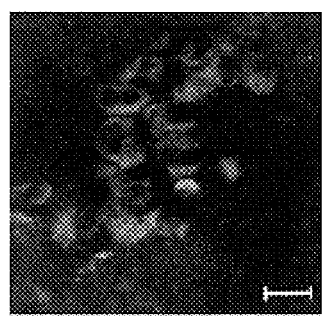
Figure 16B:
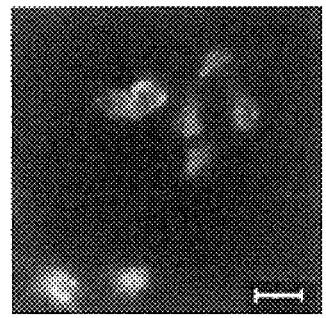
Figure 16C:
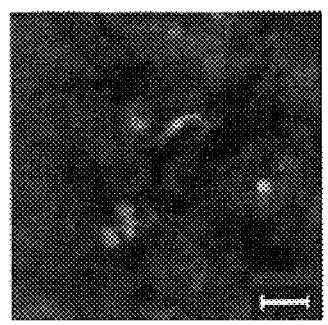
Figure 16D:
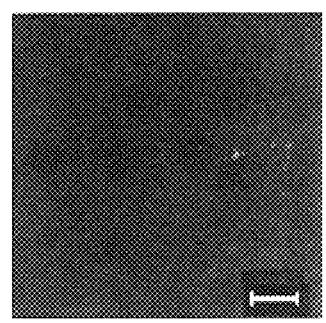
Figure 16E:
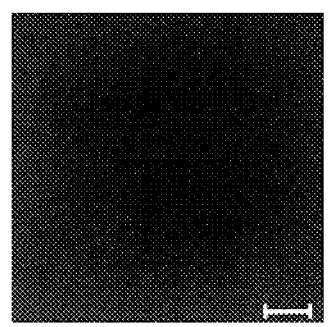
Figure 16F:
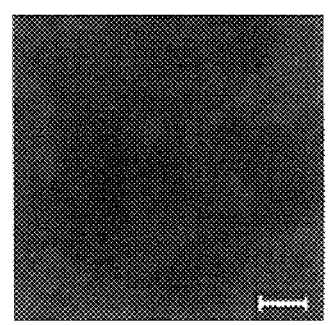

FIG. 15. Bar graph depicting tritiated thymidine uptake in mixed lymphocyte assays. Splenic lymphocytes obtained two weeks after birth were used as responder cells. Irradiated primary human hepatocytes served as stimulator cells. Lane 1, no stimulator cells were mixed with spleen cells from rats injected intrafetally with only saline (without human hepatocytes); lane 2, irradiated human hepatocytes (stimulator cells), alone; lane 3, irradiated human hepatocytes mixed with spleen cells from rats intrafetally injected with only saline; lane 4, irradiated human hepatocytes mixed with spleen cells from rats intrafetally injected with human hepatocytes and subsequently transplanted with human hepatocytes; lane 5, human hepatocytes mixed with spleen cells from rats intrafetally injected with human hepatocytes, but without subsequent transplantation with human hepatocytes, All assays were performed in triplicate. The results expressed as means±S.D. in units of cpm/$10^6$ cells.

FIGS. 16A–F. Immunohistochemical staining of cells for human albumin, left panels, and Hepatitis B Surface Antigen (HBsAg), right panels, of livers 15 weeks after inoculation with purified HBV. Panels A and B, a representative liver section from rats injected intrafetally with primary human hepatocytes, transplanted with primary human hepatocytes shortly after birth, and inoculated with purified HBV 1 week after birth. Panels C and D, rats injected intrafetally with human hepatocytes, transplanted with human hepatocytes, but not inoculated with HBV. Panels E and F, rats that received intrafetal tolerization, no human hepatocyte transplantation, but were inoculated with HBV, under identical conditions. The bars represent 10 $\mu$.

FIGS. 17A–D. In situ hybridization with a [$^{32}$P]-HBV probe. In situ hybridization of rat liver was performed as described in section 9.1, Materials and Methods. Panel A, tolerization followed by human hepatocyte transplantation, but no HBV inoculation. Panel B, tolerization, and no transplantation, but with HBV inoculation. Panel C, tolerization, transplantation, and HBV inoculation. Panel D, tolerization without transplantation or HBV exposure. Magnification 40×.

Figure 18A:
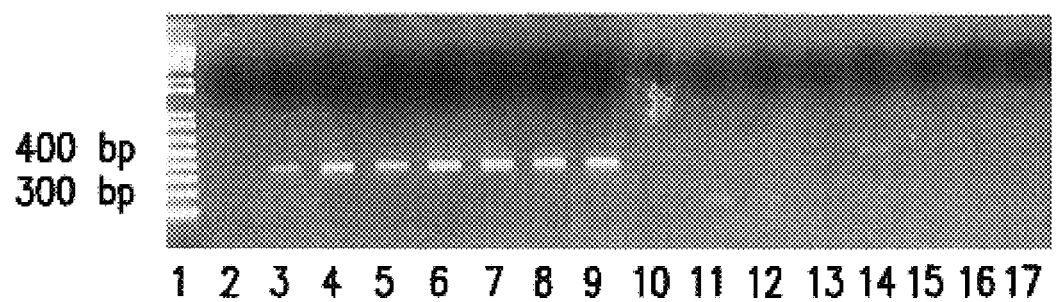
Figure 18B:
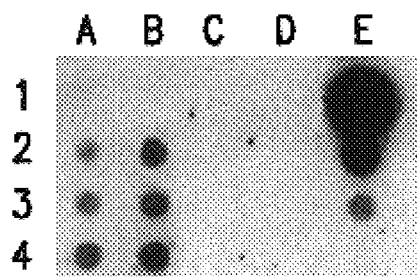

FIGS. 18A–B. Panel A. PCR for detection of serum HBV DNA. Lane 1, DNA molecular weight markers; lane 2, serum from normal rat; lane 3, positive control DNA from HepG2 2.2.15. Lanes 4–6 and 7–9, serum from two representative tolerized rats transplanted with human hepatocytes 1, 5, and 15 weeks after HBV exposure. Lanes 10 and 11, tolerized rats with human hepatocytes alone (no HBV) at 15 weeks. Lanes 12–14 and 15–17, tolerized rats without human hepatocytes, but with HBV exposure at 1, 5, and 15 weeks after HBV inoculation. Panel B. DNA dot blots of serum DNA. Two normal untreated rats, rows A and B, column 1. Two tolerized rats with human hepatocytes and exposed to HBV, rows A and B, columns 2, 3, and 4 representing post-inoculation weeks 1, 5 and 15, respectively. Tolerized rats transplanted with human hepatocytes, but with no HBV exposure, rows C and D, column 1 at 15 weeks. Tolerized rats without human hepatocytes, but exposed to HBV, rows C and D, columns 2, 3 and 4 representing post-inoculation weeks 1, 5 and 15 weeks, respectively. Row E, standard HBV DNA in serial dilutions of $10^6$, $10^5$, $10^4$ and $10^3$ copies in columns 1, 2, 3, and 4, respectively.

Figure 19A:
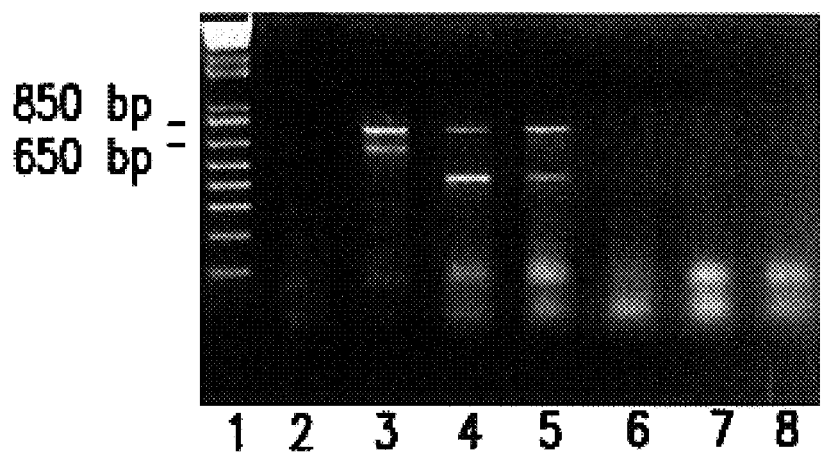
Figure 19B:
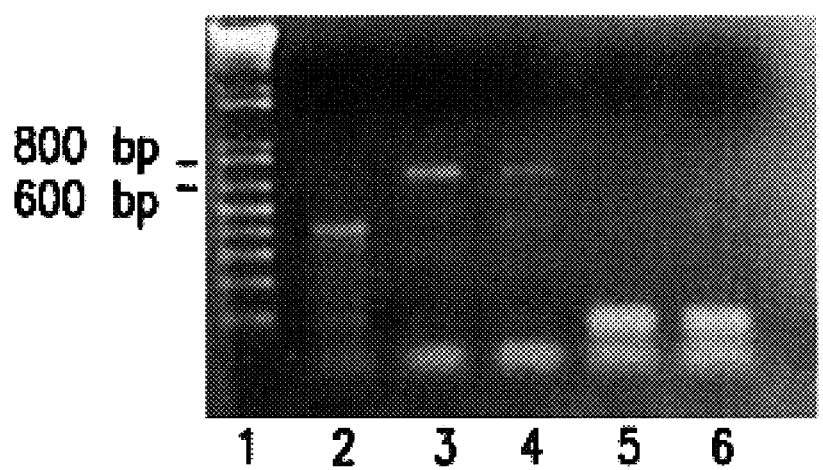

FIGS. 19A–B. PCR detection of cHBV DNA as evidence of replication. Panel A: Liver. Lane 1, DNA molecular weight markers; lane 2, control untreated rat; lane 3, DNA from HepG2 2.2.15 cells, positive control. Lanes 4 and 5: DNA from livers of two tolerized rats with human hepatocytes at 15 weeks after inoculation with HBV. Lane 6, DNA from liver of a tolerized rat with human hepatocytes alone, with no HBV exposure at 15 weeks. Lanes 7 and 8, tolerized rats with no transplantation, but with HBV inoculation, at 15 weeks after inoculation. Panel B: Serum. Lane 1, DNA molecular weight markers; lane 2, control untreated rat; lane 3, DNA from HepG2 2.2.15 cells, positive control; lanes 4, DNA from a tolerized rat with human hepatocytes at 15 weeks after inoculation with HBV; lane 5, DNA from tolerized rat with human hepatocytes alone, with no HBV exposure, 15 weeks post-inoculation; lane 6, tolerized rats, with no transplantation, but with HBV inoculation, at 15 weeks after inoculation.

Figure 20:
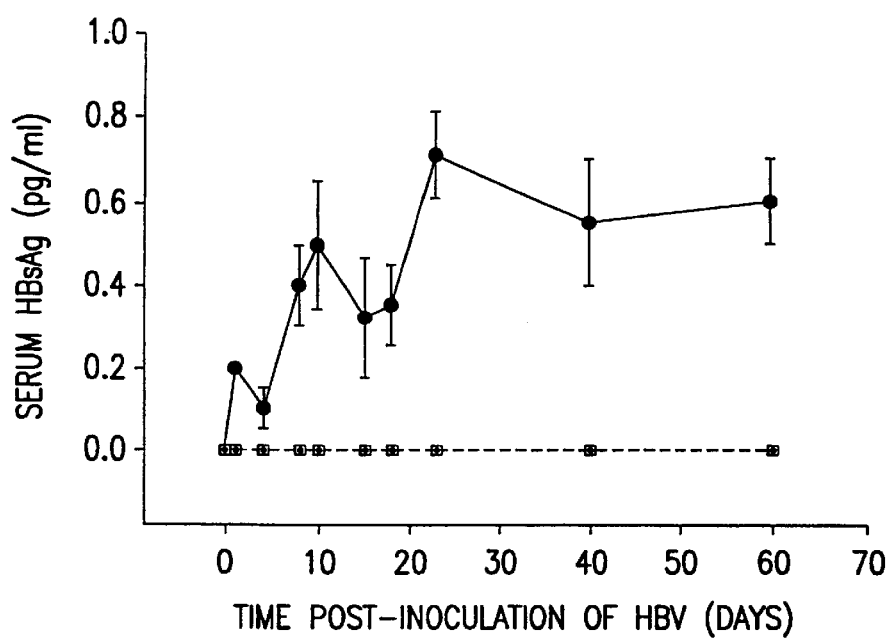

FIG. 20. Time course of serum HBsAg. Tolerized rats transplanted with human hepatocytes inoculated with HBV, solid circles; tolerized rats that did not receive human hepatocyte transplantation, but were inoculated with HBV, open squares; and tolerized rats transplanted, but did not receive HBV, crosses.

Figure 21:
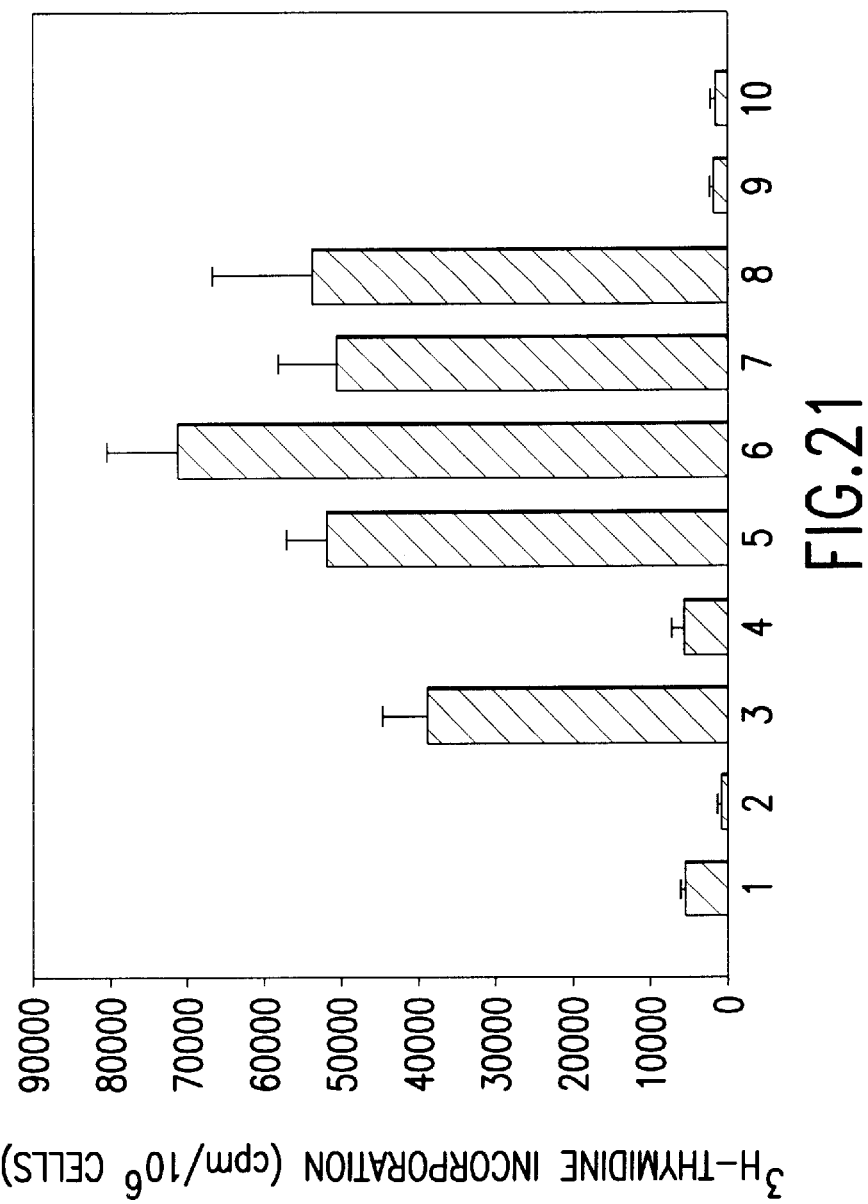

FIG. 21. Bar graph depicting results of mixed lymphocyte assays (bars are referred to as "lanes"). Rat spleen (responder) cells, from 3 rats per group, were incubated either alone, or with (stimulator) irradiated primary human hepatocytes, IMR-90 human fibroblasts, or 293 kidney cells in the presence of $^3$H-thymidine. The incorporation of radioactivity was used as a measure of proliferation of rat spleen cells induced by exposure to foreign cells. Rats exposed to human hepatocytes in utero were intrafetally injected with primary human hepatocytes on day 16 of gestation. Mixed lymphocyte assays were performed at week 1 after birth. Spleen cells from rats neither injected intrafetally with hepatocytes, nor transplanted (lane 1); irradiated primary human hepatocytes incubated alone (lane 2); spleen cells from rats neither intrafetally injected nor transplanted, but which were incubated with irradiated hepatocytes (lane 3); spleen cells from rats intrafetally injected and transplanted and subsequently exposed to irradiated hepatocytes (lane 4); responder spleen cells from intrafetally injected and transplanted, exposed to irradiated IMR-90 fibroblasts (lane 5); and 293 kidney cells (lane 6); spleen cells from animals neither intrafetally injected nor transplanted, but exposed to irradiated IMR-90 cells (lane 7); or 293 cells (lane 8); irradiated IMR-90 and 293 cells incubated alone (lanes 9 and 10, respectively). Results are expressed as means±S.E., *indicates statistical significance $P<0.05$.

Figure 22:
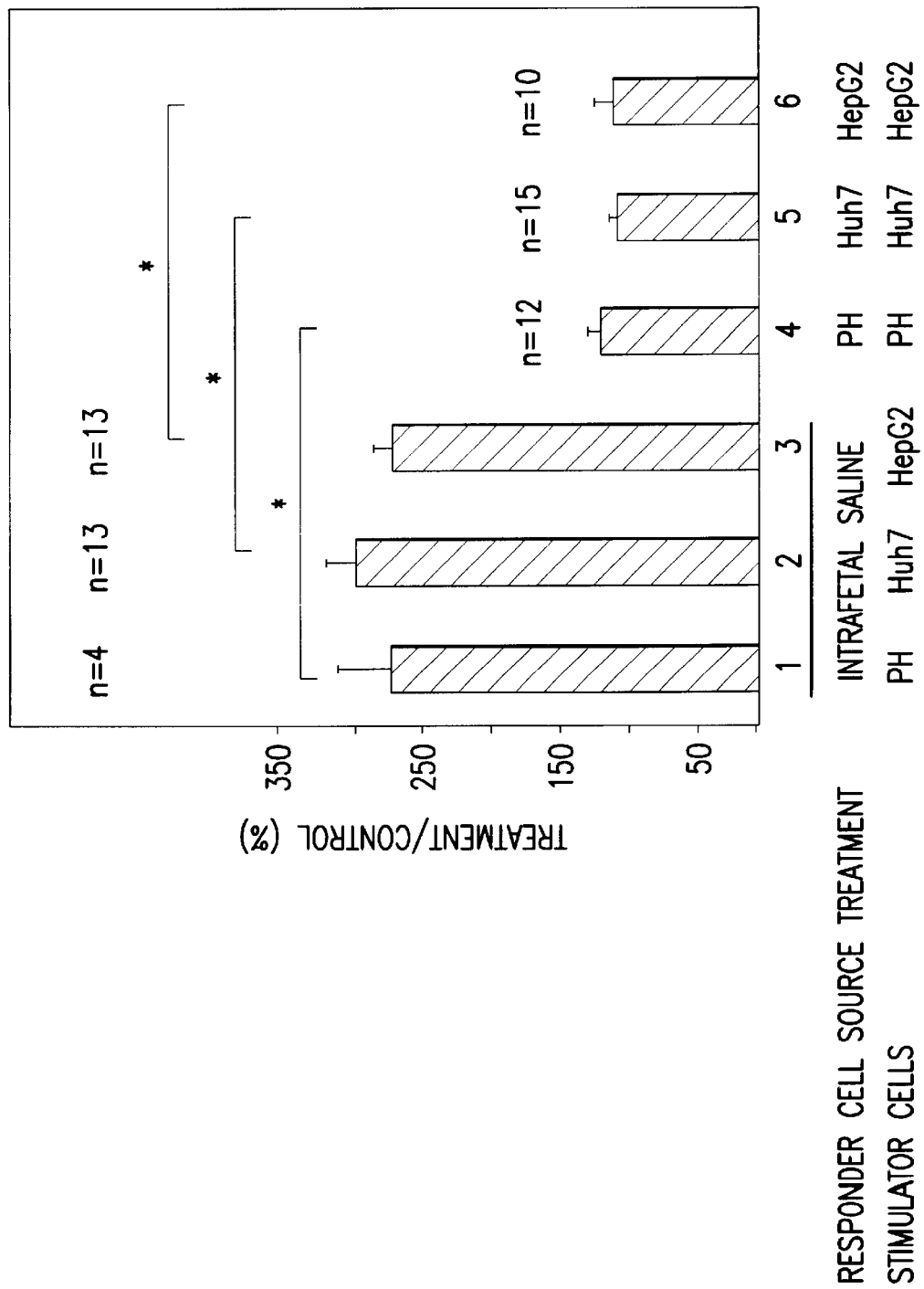

FIG. 22. Bar graph showing results of mixed lymphocyte assays for measuring tolerance induced by different types of human hepatocytes. Rats were intrafetally tolerized with either primary human hepatocytes (PH), or Huh7 cells, of HepG2 cells. All assays were performed at week 1 after birth and show radioactive incorporation by spleen cells from rats that were injected intrafetally with only saline, and subsequently incubated with primary hepatocytes, hepatoblastoma cell lines Huh7 or HepG2 (lanes 1, 2 and 3, respectively). Radioactive uptake of spleen cells from rats intrafetally injected with primary hepatocytes, Huh7 or HepG2 cells and incubated with their corresponding irradiated cells is shown in lanes 4, 5 and 6, respectively. The number of rats in each group is indicated on the top of each column. Results are expressed as percentage of controls (spleen cells from untreated rats incubated alone) as means±S.E. Duncan's test was used to analyze the significance between different treatment groups. *indicates significant differences between groups 1 and 4, between 2 and 5, and 3 and 6, $P<0.05$.

FIGS. 23A–F. Photomicrographs depicting results of immunohistochemistry assays for detecting human albumin in rat livers. Antibody against human albumin was visualized using a DAB method as described. Fifteen SD fetal rats were tolerized with Huh7 cells. Ten newborn rats were subsequently transplanted with Huh7 cells on day 1 after birth, and the rest were not transplanted. (A) shows a liver section of a representative rat that was tolerized and transplanted with Huh7 cells, sacrificed on day 1 post-transplantation, magnification ×125; (B) is the same section as (A) at a magnification of ×250. (C) shows a liver section of a representative rat that was tolerized with Huh7 cells, but which did not receive a transplant, ×125; (D) is the same section, ×250. (E) shows a liver section of a representative rat that was tolerized and transplanted with Huh7 cells and sacrificed on day 7 after birth, ×125; (F) is the same section, ×250.

FIGS. 24A–D. Confocal immunofluorescence microscopy for detection of human albumin in rat livers at week 16 post-transplantation. (A) shows a liver section of a representative rat intrafetally injected with primary hepatocytes and subsequently transplanted with primary hepatocytes, stained with monoclonal goat anti-rat albumin. (B) shows a section from the same sample as (A) stained with monoclonal mouse anti-human albumin antibody. (C) shows a liver section of a representative rat intrafetally injected with primary human hepatocytes, but not transplanted with hepatocytes, stained with anti-human albumin antibody. (D) shows the same section as (A) stained with only second antibody. Magnification, ×250.

FIGS. 25A–B. Detection of human albumin DNA in rat liver genomic DNA 16 weeks post-transplantation. From livers of animals treated as described in FIGS. 24A–D, DNA was extracted and assayed for the presence of human albumin sequences using polymerase chain reaction (PCR). The sources of DNA were: lane 1=molecular markers; lane 2=liver from untreated rats; lane $3=10^4$ Huh 7 cells; lane $3=10^3$ Huh 7cells; lane $3=10^2$ Huh 7cells; lane 6=liver from a representative rat intrafetally injected with primary human hepatocytes and transplanted with primary human hepatocytes; lane 7=liver from a rat intrafetally injected with primary human hepatocytes that did not thereafter receive a transplant. The expected position of the amplified human sequence is indicated by the arrow corresponding to 307 bp based on the DNA molecular markers in lane 1.

Figure 26A:
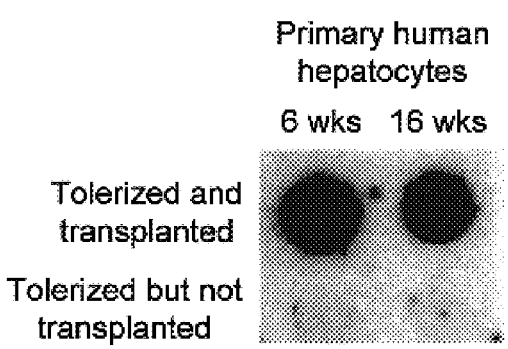
Figure 26B:
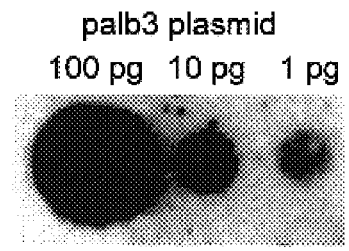
Figure 26C:
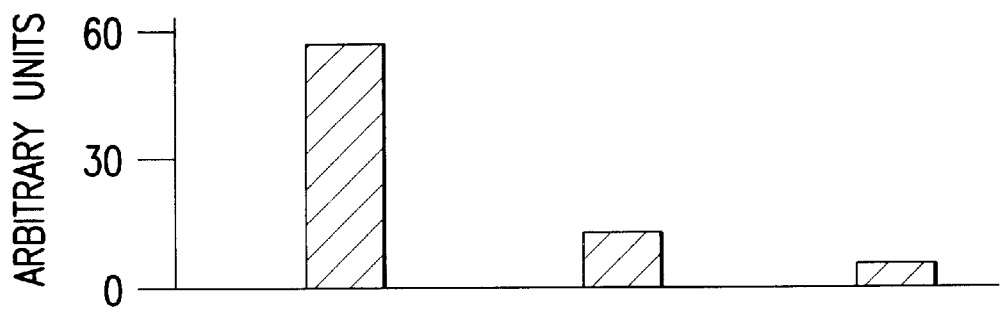

FIGS. 26A–C. Quantitation of human albumin DNA in rat livers by dot blotting. (A) upper row shows DNA extracted from liver samples from an intrafetally injected and transplanted rat at weeks 6 and 16 post-transplantation, respectively. (A) lower row shows results from a rat tolerized but without transplantation, at the same time points. All dots were hybridized with a $^{32}$P-labeled probe for human albumin DNA. (B) shows hybridization to dots of plasmid $palb_3$ DNA, which contains the complete human albumin gene, applied in decreasing amounts of 100 pg, 10 pg and 1 pg, as standards. (C) quantitates the signals in (B) using arbitrary units.

Figure 27C:
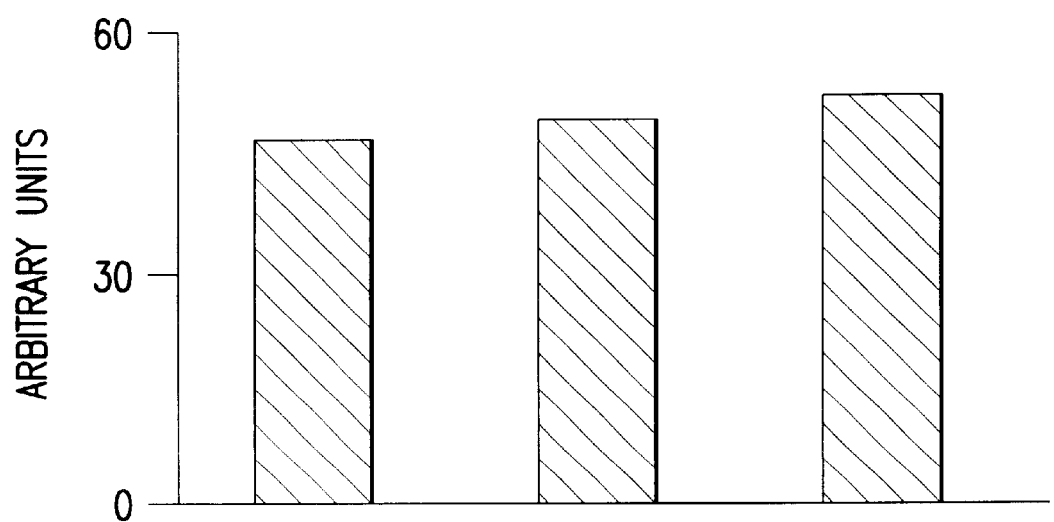
Figure 27A:
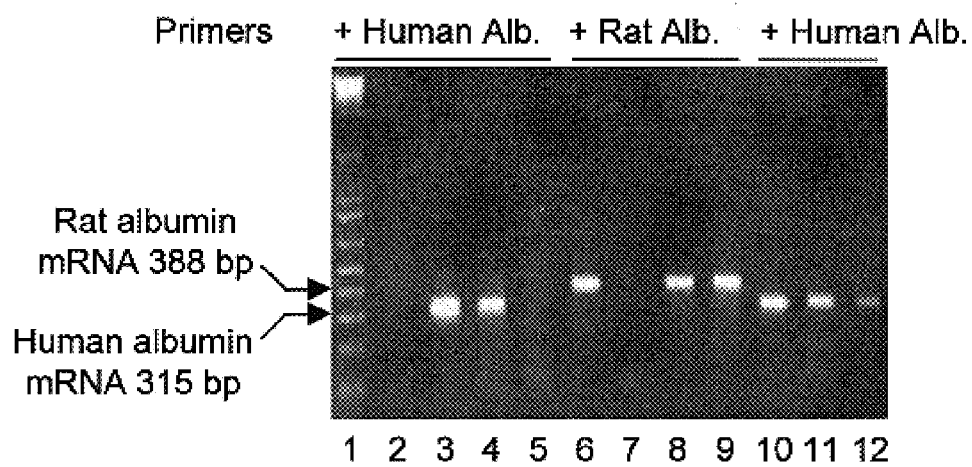
Figure 27B:
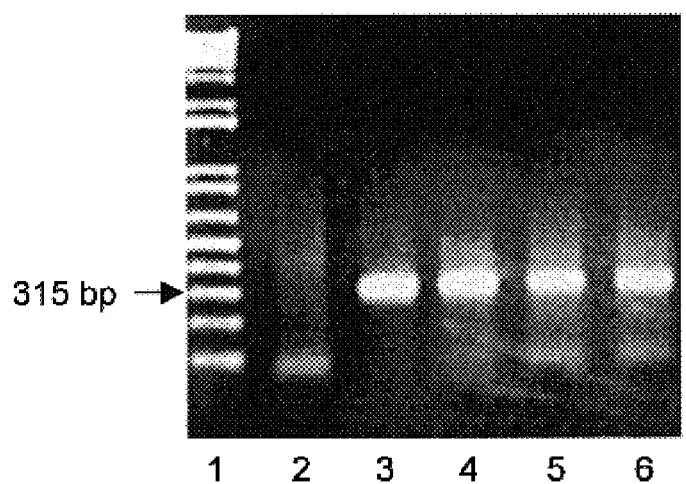

FIGS. 27A–C. Detection of human albumin mRNA in rat livers by RT-PCR. (A) shows an ethidium bromide stained gel of electrophoretically separated products of RT-PCR of RNA extracts from liver samples collected at week 16 post-transplantation. Lane 1=1 kb plus molecular markers; lanes 2 and 6=RT-PCR products generated from RNA from livers of non-tolerized rats that did not receive a human liver cell transplant; lanes 3 and 7=RT-PCR products generated from RNA of Huh7 cells (as positive controls); lanes 4 and 8=RT-PCR products generated from RNA from livers of rats intra-fetally injected and subsequently transplanted with human hepatocytes; and lanes 5 and 9=RT-PCR products generated from RNA from livers of rats intrafetally injected with human hepatocytes without subsequent transplant. For lanes 2 through 5, RNA samples were amplified with primers for human albumin DNA, and for lanes 6 through 9, samples were amplified with primers for rat albumin DNA. In lanes 10 through 12, DNA from $10^4$, $10^3$ and $10^2$ cultured Huh7 cells were amplified with primers for human albumin. The expected positions of human and rat albumin mRNA products at 315 and 388 bp, respectively, are indicated by arrows. (B) depicts an ethidium bromide stained gel of RT-PCR products of rat liver RNA using human albumin DNA specific primers, showing the time course of human albumin mRNA expression in rat livers. Lane 1=1 kb plus molecular markers; lane 2=RT-PCR products of RNA from the liver of a non-tolerized, non-transplanted rat; lane 3=RT-PCR product generated from RNA of Huh7 cells (as positive control); and lanes 4 through 6=RT-PCR products generated from liver RNA from rats tolerized and subsequently transplanted with human hepatocytes collected at weeks 2, 6 and 16 post-transplant, respectively. (C) shows quantitation of levels of human albumin mRNA in lanes 4 through 6, using arbitrary units.

Figure 28:
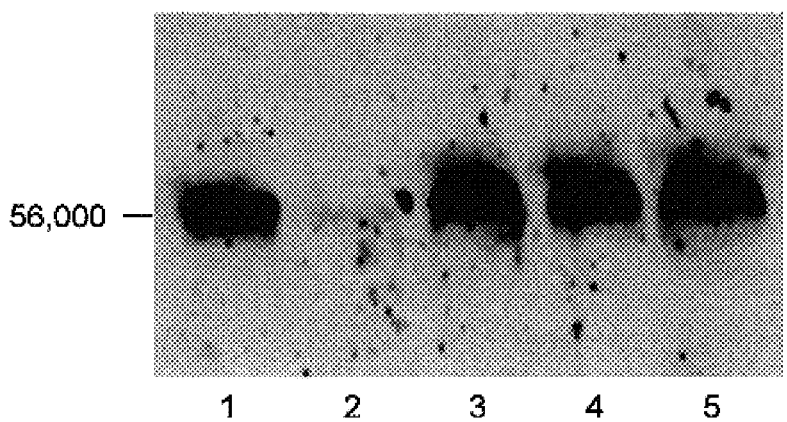

FIG. 28 depicts an autoradiograph of a Western blot in which human albumin protein is detected in rat serum. Serum samples were collected from a representative rat intrafetally injected and subsequently transplanted with primary human hepatocytes. Lane 1=human albumin standard; lane 2=rat albumin standard; lane 3=serum from rat 1 week post-transplant; lane 4=serum from rat 2 weeks post-transplant; and lane 5=serum from rat 3 weeks post-transplant.

FIGS. 29A–F. Photomicrographs indicating that cell division (as evidenced by bromodeoxyuridine incorporation) coincides with synthesis of human albumin, supporting the conclusion that transplanted human hepatocytes are proliferating in rat liver. Panels A, C, and E depict staining of liver sections for human albumin, and panels B, D and E depict staining of liver sections for bromodeoxyuridine ("BrdU") incorporation. (A) and (B) represent liver sections from a rat tolerized with human hepatocytes and treated with thyroid hormone, without transplanted hepatocytes. (C) and (D) represent liver sections from a rat tolerized with human hepatocytes, treated with thyroid hormone, and transplanted with human hepatocytes. (E) and (F) represent control liver sections from a rat which had neither been tolerized or transplanted with human hepatocytes, and which had not been treated with thyroid hormone.

Figure 30:
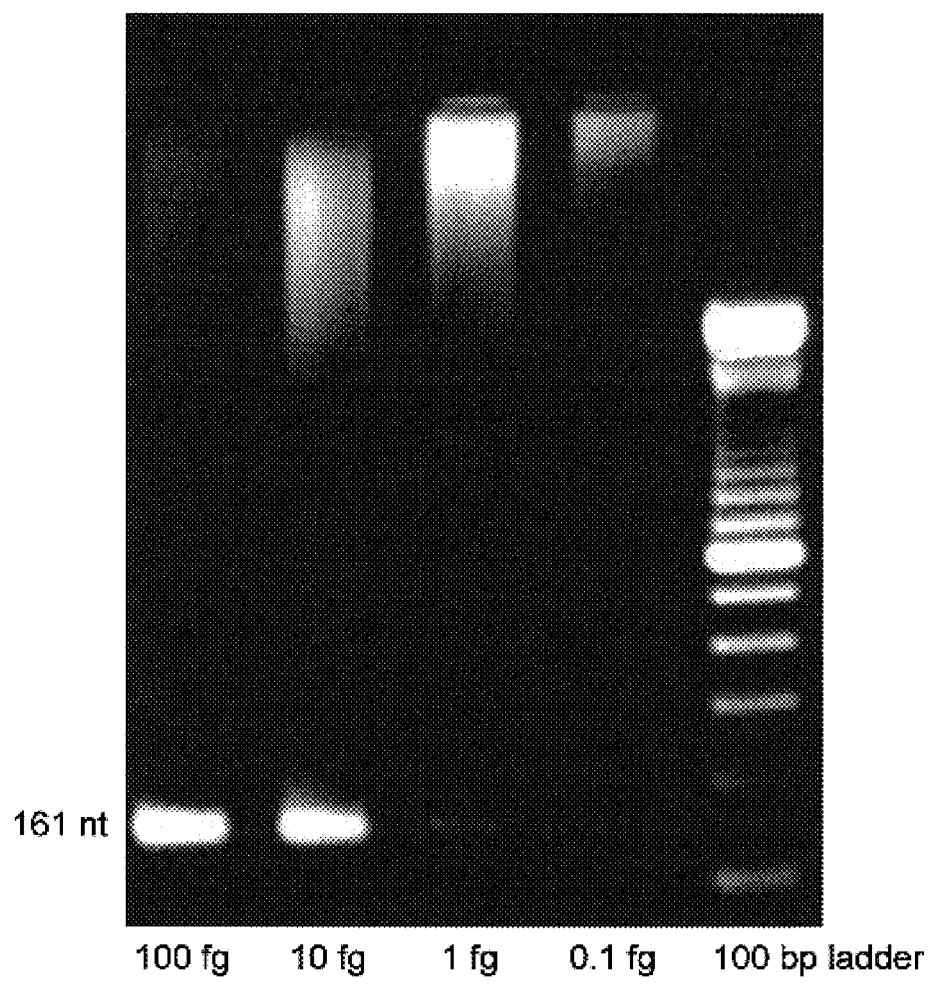

FIG. 30. Agarose gel electrophoretic analysis of PCR products from synthetic HCV(+) strand RNA substrate.

Figure 31:
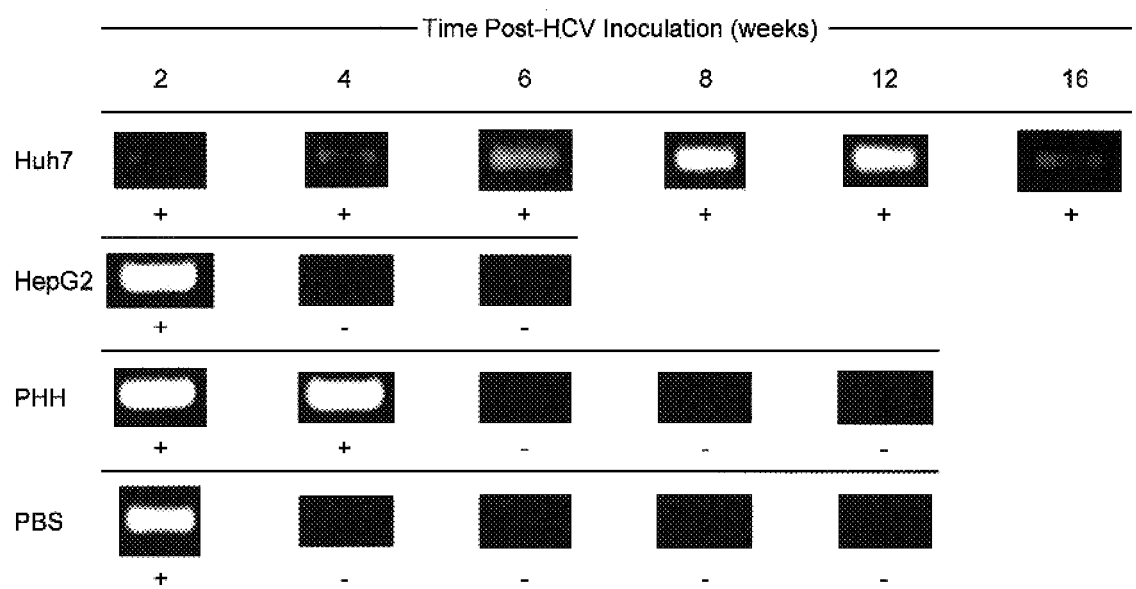

FIG. 31. HCV RNA in rat serum, as measured in FIG. 30.

Figure 32:
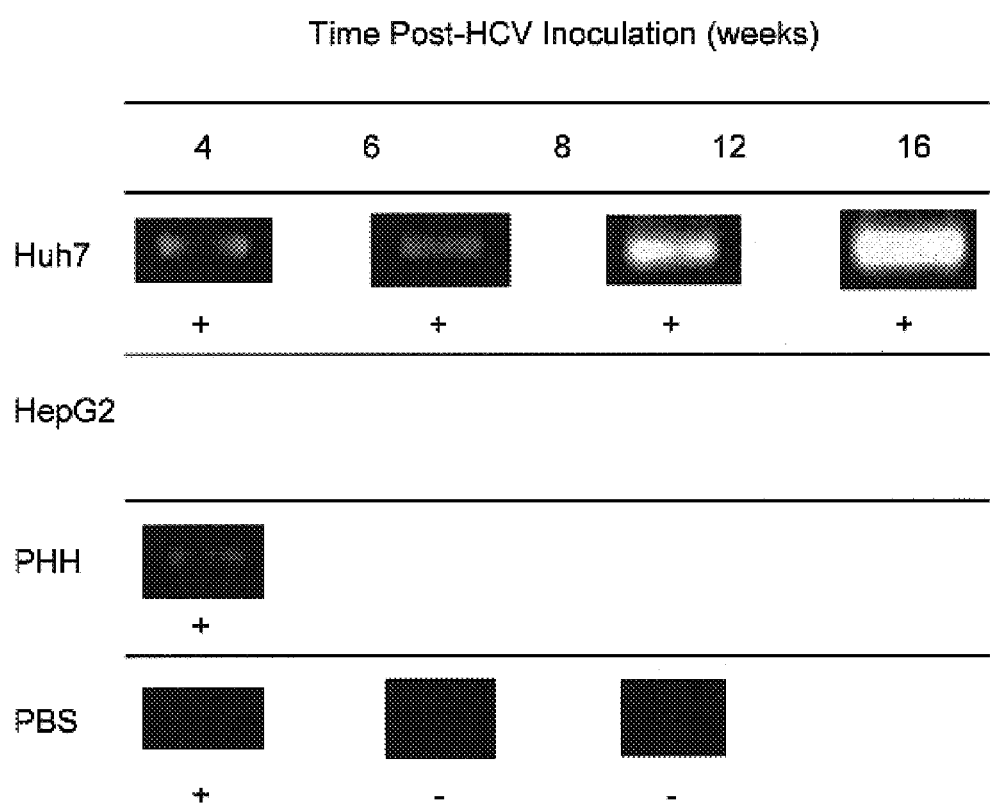

FIG. 32. HCV RNA in rat liver, as measured in FIG. 30.

5. DETAILED DESCRIPTION OF THE INVENTION

The present invention relates to tolerized non-human animals having chimeric livers comprising human hepatocytes, methods for preparing such animals, and the use of such animals either as model systems for assaying toxicology or studying human liver disease or as sources of human hepatocytes for re-introduction into a human host. For purposes of clarity, the description of the invention is presented as the following subsections:

i) producing animals having chimeric livers;

ii) toxicology model systems;

iii) model systems for liver diseases; and iv) chimeric animals as a source of hepatocytes for liver reconstitution. The subject animals of the invention are referred to herein alternatively as "non-human animals having chimeric livers" or simply "chimeric animals". Both these terms are defined as tolerized non-human animals having livers which comprise human hepatocytes.

A "human hepatocyte" as that term is used herein may be a primary hepatocyte harvested from a human liver or a cultured cell from a differentiated hepatocyte cell line. Examples of differentiated hepatocyte cell lines include cells which express one or more molecular marker associated with the differentiated hepatocyte phenotype, such as, for example but not by way of limitation, the asialoglyoprotein receptor and/or the low density lipoprotein receptor. The definition of differentiated cell lines, as that term is used herein, also includes cell lines which exhibit hepatocyte-specific function, such as, but not limited to, susceptibility to infection by a liver-specific (or selective) pathogen, such as a hepatitis B virus.

In preferred specific non-limiting examples of the invention, the differentiated hepatocyte cell lines Huh7 and HepG2 may be appropriate for certain embodiments. These cell lines are ultimately derived from hepatoblastoma cells, and therefore would not be appropriate for introduction into a human subject for gene therapy or for liver reconstitution purposes. These and other hepatoblastoma-derived differentiated hepatocyte cell lines may be used, however, to produce model systems for human liver diseases in non-human animal hosts. Furthermore, it is not required, according to the invention, that such cell lines be able to cross-tolerize an animal to primary human hepatocytes and vice-versa (in fact, it has been determined that for Huh7 and HepG2 cells, cross-tolerization is either sporadic, incomplete, or absent). The usefulness of differentiated hepatocyte cell lines as an efficient source of hepatocytes for development of model systems for liver diseases is demonstrated in the working examples, infra.

References relating to differentiated hepatocyte cell lines include Aden et al., 1979, Nature 282:615–616; Scwartz et al., 1981, J. Biol. Chem. 256:8878–8881; Wu et al., 1984, Hepatology 4(6):1190–1194; Sells et al., 1987, Proc. Natl. Acad. Sci. U.S.A. 84:1105–1009; Nakabayashi et al., 1984; Jpn J Cancer Res 75:151–151; Liang et al., 1993, J. Clin. Invest. 91:1241–1246; Chang et al., 1987, EMBO J 6:675–680; Sandig et al., 1996, Gene Therapy 3:1002–1009; Dash et al., 1997, Am. J. Pathol. 151(2): 363–373; and Yoo et al., 1995, J Virol 69:32–38.

In addition to the human hepatocytes, the livers of the chimeric animals of the invention may also include hepatocytes and non-hepatocyte elements (e.g., biliary and vascular endothelial cells, Kupffer cells, etc.) endogenous to the animal itself. Human cell types other than hepatocytes may also be present. Preferably, the percentage of human hepatocytes (relative to the total number of hepatocytes present) is at least 10 percent, more preferably at least 20 percent, or at least 50 percent, or at least 80 percent.

In particular, chimeric animals are created by introducing human hepatocytes (and possibly additional cell types) into an animal rendered immunologically tolerant to the introduced human cells. As such, the animals may be referred to as being "hosts" to the human cells, where a human being that is a source of such cells may be referred to as a "donor". The term "tolerant", as used herein, does not refer to a state of general immunosuppression (as might be achieved, for example, by treatment with cyclosporine, or as may exist in an animal with a generalized B cell and/or T cell deficiency) but rather indicates a state of antigen-induced non-responsiveness of lymphocytes achieved by clonal deletion, cell-mediated suppression, or anergy (see, for example, Davies, 1997, "Introductory Immunobiology", Chapman & Hall, London, p. 366) directed specifically toward the introduced human cells.

5.1 Producing Animals having Chimeric Livers

The present invention provides for a method of preparing a non-human animal having a liver comprising human hepatocytes, comprising (i) inducing tolerance in a host animal, where the animal is preferably a fetus or a neonate; and (ii) introducing human hepatocytes into the tolerized animal, preferably postnatally and preferably by intrasplenic injection. In specific embodiments, the host animal is subjected to a selection pressure which favors survival and/or proliferation of human, rather than host animal, hepatocytes. A detailed non-limiting description of these features of the invention is set forth in the following subsections.

5.1.1. Host Animals

Non-human animals which may serve as hosts according to the invention are preferably mammals, and include, but are not limited to, mice, hamsters, rats, rabbits, dogs, goats, sheep, pigs, cattle, etc. In particular non-limiting embodiments of the invention, the host animal is a transgenic animal carrying, as a transgene, a gene which, when expressed in hepatocytes, is directly or indirectly (i.e. via a metabolite) toxic to those cells. Examples of such genes are the urokinase gene which is directly toxic (Sandgren et al., 1991, Cell 66:245), and the Herpes simplex virus ("HSV") thymidine kinase gene ("HSV-TK"); which converts the drug gancyclovir into a toxic form and is therefore indirectly toxic (Smythe et al., 1995, Ann. Surg. 222:78–86). Preferably, the gene is operably linked to a promoter which is selectively active in hepatocytes, such as the albumin promoter, the PEPCK promoter, and the hepatitis B surface antigen promoter. To avoid destroying the animal's liver prior to colonization with human hepatocytes, it is desirable to utilize a promoter that is not particularly active prenatally. Otherwise, such transgenic animals may die in utero. Other promoters inducible by agents that could be locally administered into the liver may also be suitable, such as the metallothionein promoter (which is inducible by heavy metal ions; Palmiter et al., 1982, Cell 29:701). Such genes are not specifically toxic to human hepatocytes, although there may be some "bystander effect" whereby a limited number of the human hepatocytes are killed.

In one specific, non-limiting embodiment of the invention, transgenic mice carrying an albumin promoter/urokinase transgene may be used as hosts. Urokinase is a plasminogen activator that is useful clinically in dissolving blood clots. When introduced into hepatocytes by an adenoviral vector, it was shown to be toxic to those cells (Lieber et al., 1995, Proc. Natl. Acad. Sci. U.S.A. 92:6210–6214). In addition, Sandgren et al. prepared a transgenic mouse containing the mouse urokinase gene driven by a mouse albumin enhancer/promoter (Sandgren et al., 1991, Cell 66:245–256). Because albumin is not produced by the fetal liver (Krumlauf et al., 1985, Cold Spring Harbor Symp. Quant. Biol. 5-0:371–378), animals survived in utero because urokinase was not produced. However, after birth, with activation of the albumin promoter, the liver was destroyed due to the presence of urokinase. To produce such a transgenic mouse for use as a host, heterozygote transgenic mice, B6SJL background, may be obtained from Jackson Laboratories, Stock No. 002214, which contain the mouse urokinase gene driven by a 3.5 kb mouse albumin promoter sequence with a human growth hormone poly A addition site. Pregnant mice from heterozygotic matings may be used to generate homozygous offspring. The number of copies of the urokinase transgene present in each animal at birth may be determined from DNA extracts of tail snips, where the DNA may be digested with Kpn 1, which cuts once within the urokinase gene, and Southern blotting using a detectably labeled probe specific for the urokinase gene, such as 5'-TGTGCTTATG TAGCCATCCA GCGAGTCCCC-3' (SEQ ID NO: 1). Because somatic mutations leading to inactivation of the urokinase gene may occur, it may be desirable to use breeding pairs of male and female mice successfully rescued into adulthood by introduction of human hepatocytes to generate litters of homozygous offspring. Further, in previous studies on mice carrying a urokinase transgene, inactivating mutations in the urokinase gene were found to result in proliferation of those cells with that somatic mutation while the homozygous cells failed to grow. The proliferating cells, as expected, had higher ploidy than those less actively proliferating (Sandgren et al., 1991, Cell 66:245–256). Thus, the copy number of human DNA, if measured during proliferation of human hepatocytes may be biased, and not reflect the number of cells due to polyploidy. For this reason, the number of human cells may be better estimated by measuring markers specific for human hepatocytes, such as, but not limited to, the human albumin gene or its protein product.

In another specific non-limiting embodiment of the invention, transgenic mice carrying an albumin promoter/HSV-thymidine kinase gene may be used as hosts. Thymidine kinase of HSV differs from mammalian thymidine kinases in its ability to phosphorylate the drug gancyclovir (Fyfe et al., 1978, J. Biol. Chem. 253:8721–8727). In so doing, it converts the non-toxic agent into atoxic form (De Clerq, 1984, Biochem. Biopharmacol. 33:2159–2169). In a specific non-limiting embodiment, the HSV-TK gene (as present in plasmid pLTR-DTK, as developed by D. Klatzmann, Université Pierre et Marie Curie, Paris, France) may be linked to an albumin promoter prepared by excising a 3.2 kb fragment of the mouse albumin promoter (for example from palb$_{9-12}$LDLR, James Wilson, University of Pennsylvania, Philadelphia, Pa.) using Bgl II and Sal 1 restriction enzymes (Wilson et al., 1992, J. Biol. Chem. 267:963–967), and placing the promoter fragment in a polylinker site immediately upstream of the HSV-TK gene. Using this plasmid, founder outbred CD1 mice may be prepared and mated to normal CD1 mice to generate heterozygotes, detected by DNA analysis of tail snips using an HSV-TK specific detectably labeled probe. A breeding pair of heterozygotes may then be used to produce mice homozygous for the albumin promoter/HSV-TK transgene. It should be noted that the natural HSV-TK gene contains elements that activate the gene in the testes, which may result in sterile animals that cannot be used as breeders. Accordingly, a version of the gene which lacks these elements is preferred, such as the gene contained in plasmid pLTR-$\Delta$TK (all such variant genes, as well as the wild-type, are considered HSV-TK genes). Breeding of transgenic mice with this specific construct confirmed the success of the deletion (Salomon et al., 1995, Mol. Cell. Biol. 15:5322–5328). Further, a gancyclovir dose-related (Culver et al., 1992, Science 256:1550–1552) bystander effect of the HSV-TK gene product has been observed whereby nearby cells lacking the transgene are destroyed (Kolberg, 1994, J. NIH Res. 6:62–64). Accordingly, it may be desirable to evaluate different doses of gancyclovir and identify the minimum dose required to produce maximal human hepatocyte proliferation.

In yet another non-limiting embodiment of the invention, a drug which is metabolized to a toxic agent by liver cells may be used to reduce the number of host liver cells. For example, such a drug may be administered subsequent to tolerization but prior to human hepatocyte transplant. Preferably, there is a delay between exposure to the drug and death of host animal hepatocytes, so that the animal can maintain liver function while transplanted hepatocytes proliferate to a point where they are present in sufficient numbers to supply the level of liver function required for viability. According to one embodiment, the drug may be retrorsine, a pyrrolizidine alkaloid, which is metabolized by liver cells to a toxic DNA alkylating intermediate. The dose of such agent should be titrated to establish a dosage which will preserve the viability of the animal. For example, two doses of 30 mg/kg of retrorsine given two weeks apart were lethal to newborn rats, and one dose of 30 mg/kg was not sufficient to eliminate all rat liver cells, but it was found that two doses of 12 mg/kg retrorsine, with the first dose given at birth and the second given two weeks later, were not lethal. Accordingly, the present invention provides for the treatment of tolerized newborn rats with a dose of retrorsine of 10–30 mg at birth and then 10–30 mg two weeks theraftar, for a total amount of retrorsine less than 60 mg and preferably les than 40 mg, to prepare newborn rats to receive a human hepatocyte transplant.

5.1.2. Tolerization

Non-human animals which are to be used as hosts for human hepatocytes may be rendered tolerant to those hepatocytes by administration of the relevant antigen(s), preferably in the context of human cells or a lysate prepared from human cells, more preferably using human cells from the same individual who is to serve as the hepatocyte donor, or a genetically related and/or identical individual, or, where a differentiated hepatocyte cell line is used, preferably from the same sub-culture (e.g., a culture used as a source of cells for tolerization is preferably derived from the same laboratory stock, and preferably the same culture separated by ten passages or less) as cells to be used for transplant. Tolerizing antigen(s) may be administered as whole cells, a cell extract or one or more purified component thereof. The source of tolerizing antigen(s) may be hepatocytes, but may alternatively be cells of another type, or a mixture of different types of cells. For example, cells prepared from a specimen of human liver tissue may be used as a source of tolerizing antigen(s); such cells may include not only hepatocytes but also fibroblasts, cells of the biliary system, vascular endothelial cells, Kupffer cells, etc. As another example, human splenocytes or lysates thereof may be used to induce tolerance. Cells to be used in tolerization are preferably cleared of undesirable constituents. For example, if the animal is eventually to be used as a model system for a disease where an immune response to an infectious agent is desirably left intact, the animal should not be tolerized against the infectious agent. Alternatively, if the animal is to be used as a host to support the proliferation of human hepatocytes to be used to reconstitute the liver of a person having liver damage caused by an infectious agent, it is desirable not to tolerize the host animal toward the infectious agent or to introduce the infectious agent into the host animal at any time. The cells or lysate are introduced in a physiologically compatible solution; herein, volumes administered refer to cells or lysate comprised in such a solution.

While the host animal may potentially be of any age when tolerized, tolerization is likely to become more difficult as age of the animal increases. Preferably, the animal is still an infant when tolerized; more preferably, the animal is tolerized during the perinatal period when the animal is a neonate, or tolerized in utero. The terms "neonate" and "newborn" are used interchangeably herein. If the intended host animal is a rat, the preferable upper age limit for tolerization is 18 days post-conception (in utero), and the more preferable age for tolerization is 17 days post-conception (in utero), or within 24 hours after birth. If the intended host animal is a mouse, the preferable upper age limit for tolerization is 18 days post-conception (in utero), and the more preferable age for tolerization is 17 days post-conception (in utero), or within 24 hours after birth. If the intended host animal is a pig, the preferable upper age limit for tolerization is 90 days post-conception, and the more preferable age for tolerization is 80 days post-conception, when the animal is still in utero, or within 24 hours after birth.

Tolerization may be accomplished by any route, including but not limited to intravenous, intraperitoneal, subcutaneous, and intrathymic routes. Preferred methods of tolerization include inoculation of human cells into the thymus or intraperitoneally.

As a specific, non-limiting example, where the intended host animal is a rat, tolerance may be induced by inoculating lysate prepared from $1 \times 10^4 – 1 \times 10^6$ and preferably $10^5$ human hepatocytes into the peritoneum of a 15–18 day old, and preferably a 17 day old, rat fetus in utero under transillumination. The lysate may be prepared by sonicating a suspension of the appropriate number of human hepatocytes. The same numbers of whole cells may also be inoculated into the peritoneum during the aforesaid time periods. If the intended host animal is a mouse, the number of human hepatocytes represented in the lysate may be $1 \times 10^3 – 1 \times 10^5$ and preferably $10^4$ and intraperitoneal inoculation may be performed between days 15 and 18 post conception. If the intended host animal is a pig, the number of human hepatocytes represented in the lysate may be between about $10^5$ and $10^6$ or the same number of whole cells and intraperitoneal inoculation may be performed at between about 75 and 90 days post-conception. Alternatively, intraperitoneal inoculation can be performed while the animals are neonates.

As a second non-limiting example, tolerance may be induced by intrathymic injection according to a method as described in Fabrega et al., 1995, Transplantation 59:1362–1364. Either whole cells or a cell lysate may be administered. In particular, where the intended host animal is a rat, about $1 \times 10^2 – 1 \times 10^5$ human hepatocytes (or a lysate thereof) in between about 1 and 10 microliters, preferably about 5 microliters, may be injected into the thymus of a newborn (neonatal) rat, preferably within 1–2 hours of birth. Where the intended host animal is a mouse, about $1 \times 10^2 – 1 \times 10^4$ and preferably 100 human hepatocytes (or a lysate thereof) in between about 1 and 10 microliters and preferably about 5 microliters may be injected into the thymus of a mouse that is up to 3 months old and preferably a neonate, e.g. within 1–2 hours or within 24 hours of birth. Where the intended host animal is a pig, about $10^5 – 10^6$ human hepatocytes (or a lysate thereof) in between about 50 and 200 microliters may be injected into the thymus of an infant pig that is preferably up to one week old. As a specific example, a neonatal mouse may be anesthetized by chilling on ice, the thoracic area may be cleaned with alcohol and betadine swipes, the thymus may be visualized through the translucent skin of the newborn, and a 1–2 mm incision may be made with ophthalmic scissors to expose the thymus. The human cells or human cell lysate may then be slowly injected into the thymus, and then the incision may be closed with a sterile nylon suture. The incision area may then be recleaned and the mouse placed on a warming pad and returned to its mother as soon as possible.

The success of tolerization may be assessed by proceeding to introduce human hepatocytes into the animal, and determine whether or not they survive long-term (for example, by monitoring the production of human serum albumin; see infra). Alternatively, the ability of lymphocytes from the animal to react with donor human hepatocytes may be evaluated using standard immunologic techniques, such as methods that determine T cell proliferation in response to donor hepatocytes, the induction of a cytotoxic T cell response, or mixed lymphocyte reaction.

5.1.3. Introduction of Human Liver Cells

Human hepatocytes may then be introduced into host animals rendered tolerant as set forth in the preceding section. The hepatocytes may preferably be introduced via intrasplenic injection, although other routes may also be used, such as direct injection into the liver parenchyma, under the liver capsule, or via the portal vein.

As a specific non-limiting example, where the intended host animal is a rat tolerized as set forth above, between about $10^6 – 5 \times 10^7$ human hepatocytes, preferably about $2 \times 10^6$ hepatocytes, may be introduced into a tolerized rat within about 24 hours after birth by anesthetizing the animal, making a 3–4 mm incision in the left paracostal area to visualize the spleen (Marucci et al., 1997, Hepatol.

26:1195–1202), and injecting the donor cells in a volume of approximately about 50–300 microliters, and preferably about 200 microliters, of sterile medium. Where the intended host animal is a tolerized mouse, the number of human hepatocytes introduced by an analogous procedure may be between about $5 \times 10^3$ and $5 \times 10^6$, preferably about $10^5$ in a volume of about 25–200 microliters, and preferably about 100 microliters, of sterile medium, and the human hepatocytes are administered between about one day and two months, preferably 3–4 days, after tolerization. Where the intended host animal is a tolerized pig, the number of human hepatocytes may be between about $10^8$–$10^{10}$, preferably about $10^9$, in a volume of about 10–20 milliliters of sterile medium and the human hepatocytes are administered about one and seven days after birth or about 35 days after tolerization.

Human hepatocytes may be obtained from a commercial source, for example, Clonetics Corporation, 8830 Biggs Ford Road, Walkersville, Md. 21793, which sells normal human hepatocytes as catalog number CC-2591, or Invitro Technologies, Inc., Baltimore, Md.

Alternatively, human hepatocytes may be prepared from a donor as follows. The source of cells may be from a liver biopsy taken percutaneously or via abdominal surgery, or from liver tissue obtained postmortem. The source of cells should be maintained in a manner which protects cell viability. In one specific non-limiting embodiment, human hepatocytes may be prepared using the technique described in Guguen-Guillouzo et al., 1982, "High yield preparation of isolated human adult hepatocytes by enzymatic perfusion of the liver", Cell Biol. Int. Rep. 6:625–628. Briefly, the method of Guguen-Guillouzo et al. involves (i) isolating a liver or a portion thereof from which hepatocytes are to be harvested; (ii) introducing a cannula into the portal vein or a portal branch; (iii) perfusing the liver tissue, via the canula, with a calcium-free buffer followed by an enzymatic solution containing 0.025% collagenase (e.g., Type 4, from Sigma Chemical Company) in 0.075% calcium chloride solution in HEPES buffer at a flow rate of between 30 and 70 milliliters per minute at 37° C.; then (iv) mincing the perfused liver tissue into small (e.g. about 1 cubic millimeter) pieces; (v) continuing the enzymatic digestion in the same buffer as used in step (iii) for about 10–20 minutes with gentle stirring at 37° C. to produce a cell suspension; and (iv) collecting the released hepatocytes by filtering the cell suspension produced in step (v) through a 60–80 micrometer nylon mesh. The collected hepatocytes may then be washed three times in cold HEPES buffer at pH 7.0 using slow centrifugation (e.g., 50×g for five minutes) to remove collagenase and cell debris. Non-parenchymal cells may be removed by metrizamide gradient centrifugation. If the amount of liver tissue is too small to perform the above perfusion procedure, for example, less than 100 g of tissue, then the tissue may be minced and digested with collagenase solution with gentle stirring and processed according to steps (iv) and (v) of this paragraph.

It may be desirable to separate human hepatocytes prepared as set forth above into a subset for introduction into animals and another subset which is undesirable to propagate. For example, if a human subject is to serve as a donor for hepatocytes which are to be propagated in a chimeric animal according to the invention and then reintroduced into the subject, e.g., to reconstitute a liver damaged by infectious disease or malignancy, it would be desirable not to propagate hepatocytes which are infected or which have undergone malignant transformation. In such a situation, it would be desirable to eliminate infected or malignant hepatocytes from the population of hepatocytes which is to be introduced into the host animal. Elimination of unwanted cells can be performed by standard cell sorting techniques, for example fluorescence activated cell sorting using an antibody specific for the infectious agent or for malignant transformation. Alternatively, undesirable cells may be eliminated or attenuated by treatment with antiviral or antimicrobial compounds, radiation, antibody-ligated toxins, culture techniques, etc.

Where a differentiated hepatocyte cell line is to be used for transplantation, such as, but not limited to, Huh7 or HepG2 cells, the cell lines may be obtained from a standard laboratory source (see Liang et al., 1993, J. Clin. Invest. 91:1241–1246). For example, Huh7 may be obtained from individual investigators. HepG2 has the American Type Culture Collection ("ATCC") Accession Number HB-8065; the address of the ATCC is 10801 University Blvd., Manassas, Va. 20110-2209.

5.1.4. Favoring Proliferation of Human Hepatocytes

In particular non-limiting embodiments of the invention, selection pressure may be used to favor the proliferation of human hepatocytes. Such selection pressure is defined herein as including any condition, preexisting in the host animal at the time of introduction of donor cells or imposed thereafter, which results in a greater likelihood that human hepatocytes, rather than host hepatocytes, will proliferate.

For example, the selection pressure may result from the presence of a transgene that decreases the viability of host hepatocytes, either intrinsically (directly) or by administration of an activating agent (indirectly). Alternatively, human donor hepatocytes can be transfected with a protective gene that will enable those cells to survive subsequent exposure to a hepatotoxin. In one specific non-limiting example, the transgene may be the albumin promoter/urokinase construct, whereby as the host animal matures and the albumin promoter becomes active, host hepatocytes may be eliminated by the toxic effects of urokinase. In such cases, the selection pressure is maturation of the animal with consequent transgene activation. In a second specific non-limiting example, the transgene may be the albumin promoter/HSV-TK construct, whereby when gancyclovir is administered to the host animal (e.g., as an intraperitoneal injection of 250 mg/kg gancyclovir in sterile PBS), hepatocytes of the transgenic host may be selectively killed. In such embodiments, the death of host hepatocytes would be expected to favor compensatory proliferation of human hepatocytes. This can occur because of the known property of parenchymal liver cells to proliferate during conditions that stimulate regeneration.

It may be preferable to effect stepwise attenuation of host hepatocytes rather than eliminate a majority in a short period of time, as the sudden loss of liver function could result in death of the animal and/or conditions that would disfavor the establishment of a human hepatocyte population in the host liver. For example, administration of several doses of gancyclovir to a host animal transgenic for the albumin promoter/HSV-TK construct, beginning before and continuing after introduction of donor cells, may result in a gradual elimination of host cells, thereby permitting human hepatocytes to establish a "foothold" before the majority of host hepatocyte function is eliminated.

In another non-limiting embodiment, donor hepatocytes can be transfected with a protective gene. For example, a gene encoding an antisense RNA or ribozyme against the cytochromes 2E1, 1A2, and/or 3A4 (CYP2E1, CYP1A2, CYP3A4, respectively), would prevent activation of the drug acetaminophen. Metabolites of that agent within liver cells results in hepatocyte death. Thus, donor cells containing the transgene would have a survival advantage relative to host cells if massive doses of acetaminophen were administered after cell transplantation. A similar strategy would be to transfect a mutant RNA polymerase II that is resistant to the effects of the hepatotoxin phalloidin. Administration of phalloidin to hosts bearing transfected human hepatocytes producing the mutant polymerase would be protected and have a selective advantage over host cells.

5.1.5. Confirming the Presence of Human Hepatocytes

The presence of human hepatocytes in a host may be evaluated by assaying for specific human markers. The presence of such markers in a blood sample or a liver biopsy collected from the animal (e.g., percutaneously) may be evaluated without affecting the viability of the animal. Alternatively, the success of chimerization may be evaluated retrospectively at necropsy.

As a specific example, the presence or absence of immunologically distinct human albumin may be determined in a blood or tissue sample by Western blot analysis or immunohistochemistry using antibody specific for human, but not host, albumin (see, for example, Wu et al., 1991, J. Biol. Chem. 266:14338–14342; Osborn and Weber, 1982, Meth. Cell Biol. 24:97–132). An example of a publicly available antibody specific for human albumin is Sigma #A6684 monoclonal anti-human albumin HSA II.

5.2. Toxicology Model Systems

In particular non-limiting embodiments of the invention, a chimeric animal prepared as set forth above may be used as a model system for human hepatocyte function in a toxicology study to determine the toxic effect(s) of a test agent on (i) the human hepatocytes present in the animal and/or (ii) the host animal itself. The chimeric animals of the invention provide the opportunity to recapitulate, in a model system, metabolism of the test agent by human hepatocytes, which may result in one or more secondary compounds that may not be produced when the test agent is exposed to non-human hepatocytes.

Because a test agent may have different effects on host hepatocytes and human hepatocytes, it is desirable to determine the relative proportion of human and host hepatocytes in each test animal, for example by quantitation of the amounts of human and non-human albumin in a serum sample. The ability of this measurement to accurately reflect liver cell populations may be established by correlating serum albumin levels with hepatocyte populations as evaluated by immunohistochemistry in liver tissue samples obtained by biopsy or at necropsy. Once the relative proportions of hepatocyte populations for each animal are determined, experimental results relating to the effect of test agent may be compared with the effect of test agent on a control non-chimeric animal which represents a population of 100 percent host hepatocytes. Preferably, the host hepatocytes are less sensitive to test agent than human hepatocytes.

Accordingly, chimeric animals of the invention may be used to evaluate the toxic effect(s) of a test agent on the viability (survival, function) of human hepatocytes in the animal and/or the animal as a whole by subjecting at least one and preferably a plurality of chimeric animals and non-chimeric animals of the same species (as controls) to incremental doses of test agent. At one or a series of time point(s), the animal(s) may be evaluated by standard laboratory tests to determine whether toxic effects have occurred. Such an evaluation may include an assessment of bodily functions, as reflected by weight and/or activity and analysis of blood and/or urine, for example for test agent or its metabolites, markers of liver function and/or hepatocyte viability, kidney function, immune function, etc. As discussed above, such information is considered in view of the percentage of human hepatocytes in each test animal's liver and the relative effects of test agent on human versus host hepatocytes. Further, the percentage of human hepatocytes may change during the course of an experiment, for example, if the test agent is selectively toxic to human hepatocytes so that compensatory proliferation of host hepatocytes occurs. Accordingly, it is desirable to perform measurements of relative quantities of one or more marker specific for human hepatocytes at each time point; for example, the relative amounts of human and host albumin in serum may be measured by Western blot. At one or more time point of the study, an animal(s) may be biopsied and analyzed for human versus host albumin gene or gene product, or human-specific Alu repeat sequence, or sacrificed and a complete necropsy analysis be performed, including immunohistochemical evaluation of hepatocyte populations in the liver.

5.3. Model Systems for Liver Disease

In another non-limiting embodiment of the invention, an animal having a chimeric liver may be used as a model system for human liver disease. Such chimeric animals may be used to create models of liver disease resulting from exposure to a toxin, infectious disease or malignancy. The model systems of the invention may be used to gain a better understanding of these diseases and also to identify agents which may prevent, retard or reverse the disease processes.

Where the chimeric animal is to be used as a model for liver disease caused by a toxin, animals prepared as set forth above may be allowed to mature to a point where the size of the human hepatocyte population is substantial (e.g. has approached a maximum), and then be exposed to a toxic agent. The amount of toxic agent required to produce results most closely mimicking the corresponding human condition may be determined by using a number of chimeric animals exposed to incremental doses of toxic agent. Examples of toxic agents include but are not limited to alcohol, acetaminophen, phenytoin, methyldopa, isoniazid, carbon tetrachloride, yellow phosphorous, and phalloidin.

In embodiments where a chimeric animal is to be used as a model for malignant liver disease, the malignancy may be produced by exposure to a transforming agent or by the introduction of malignant cells. The transforming agent or malignant cells may be introduced with the initial colonizing introduction of human hepatocytes or, preferably, after the human hepatocytes have begun to proliferate in the host animal. In the case of a transforming agent, it may be preferable to administer the agent at a time when human hepatocytes are actively proliferating. Examples of transforming agents include aflatoxin, dimethylnitrosamine, and a choline-deficient diet containing 0.05–0.1% w/w DL-ethionine (Farber and Sarma, 1987, in *Concepts and Theories in Carcinogenesis*, Maskens et al., eds, Elsevier, Amsterdam, pp. 185–220). Such transforming agents may be administered either systemically to the animal or locally into the liver itself. Malignant cells may preferably be inoculated directly into the liver.

Where the chimeric animal is to be used as a model for infectious liver disease, the infectious agent, or an appropriate portion thereof (e.g. a nucleic acid fragment) may be introduced with the initial introduction of hepatocytes or after the human hepatocytes have begun to proliferate. The infectious agent may be administered as a free entity or incorporated into a human cell such as a human liver cell. Examples of infectious diseases suitable for modeling include but are not limited to hepatitis A, hepatitis B, hepatitis C, hepatitis D, hepatitis E, malaria, Epstein Barr infection, cytomegalovirus infection. and Yellow Fever. For such models, it may be advantageous that the host animal has an immune system that is intact (but for the induced tolerance to the host cells), in that the animal's immune response to the infectious agent and/or infected human hepatocytes may produce a more accurate model of human liver diseases in which the immune system plays a pathogenic role. As such, it may be desirable to ensure that the cells/cell lysate used for tolerization not include infectious agent or related antigens. A working example in which the invention is used to produce a hepatitis B virus model system is set forth below.

Further, where the infectious agent is a virus, the present invention provides for chimeric animals comprising human hepatocytes that contain a nucleic acid of the virus, such as the entire viral genome or a portion thereof, or a nucleic acid encoded by the viral genome or a portion thereof.

5.3.1. HCV Model Produced by Infectious Serum

In a particular non-limiting embodiment, the invention provides for a chimeric animal model for hepatitis C virus infection.

In one set of preferred embodiments, the host animal is tolerized and subsequently transplanted with cells of a differentiated human hepatocyte cell line. In one specific, non-limiting example of such embodiments, the cell line is Huh7. In a more specific non-limiting example, the chimeric animal is a rat tolerized and transplanted with Huh7 cells.

In another non-limiting set of embodiments, the chimeric animal is a mouse transgenic for a gene whose product is selectively toxic to hepatocytes, such as the albumin promoter/urokinase gene or the albumin promoter/HSV-TK gene. Hepatitis C infection of human hepatocytes in such mice may be produced either (i) concurrently with or preferably (ii) after the colonizing introduction of human hepatocytes and after the effects of the toxic transgene have attenuated or eliminated host hepatocytes. Preferably, the chimeric animal has, prior to infection, a liver which comprises substantially (at least about 20 percent, preferably at least 50 percent, more preferably at least 80 percent) human hepatocytes.

The source of infectious agent may be serum from one or more human subject infected with HCV but not demonstrably infected with one or more other agents that infect hepatocytes. Serum samples of genotype Ia may be assayed for viral load by branched DNA (bDNA) assay (Chiron, San Francisco, Calif.). Sera from non-infected subjects and individuals with non-viral hepatitis may be used to pseudo-infect control chimeric animals. Using standard biohazard precautions, serum containing HCV RNA from infectious human serum, at a titer ranging between about $10^3$–$10^7$ particles per milliliter may be injected intravenously into a chimeric animal about 2–4 months and preferably about 6 weeks after colonization with human hepatocytes. Preferably, increasing amounts of HCV RNA in infectious human serum, with the viral titer previously determined (e.g., by National Genetics Institute, Los Angeles, Calif.) may be injected into a panel of such chimeric animals.

Where the chimeric animal is a rodent, the site of injection may be the tail vein, and the volume of serum injected may be 0.1–0.5 ml. The serum may preferably be filter sterilized prior to administration. In a preferred embodiment, a chimeric rat is anesthetized, its spleen is exposed, and 100,000 copies of HCV/0.1 ml serum is injected into the spleen; pressure is applied at the injection site and then the incision is closed.

Serum may be collected from the chimeric animal(s) and tested to establish baseline and post-infection levels of liver function markers such as AST (aspartate amino transferase), ALT (alanine aminotransferase) and alkaline phosphatase. For example, baseline and weekly post-infection levels of AST, ALT and alkaline phosphatase in serum may be determined spectrophotometrically using kits from Sigma Chemical Co., St. Louis, Mo., where appropriate standards are used to generate reference curves. Where the animals are rodents, blood samples may be obtained retroorbitally using standard techniques.

The chimeric animal(s) may be tested for seroconversion against HCV by testing for circulating antibody (e.g., anti-C100-3 antibody), for example using the ELISA kit available from Ortho Diagnostics (catalog number 930740: Ortho HCV ver. 3.1 ELISA TEST SYSTEM; Ortho Diagnostics, Raritan, N.J.). Tests for seroconversion may be performed, for example, at weekly intervals for the first month after infection and then monthly.

Viral load may be determined (e.g., weekly) by assay of dilutions of serum for positive strand HCV RNA using thermostable rTth RT-PCR performed under stringent conditions (at 70° C.) to eliminate false priming of the incorrect strand. Branched DNA analysis may also be used, but it is not as sensitive. For positive strand RNA analysis, the cDNA reverse primer may be: 5'-TCGCGACCCA ACACTACTC 3' (SEQ ID NO: 2) and the forward primer may be 5'-GGGGGCGACA CTCCACCA-3' (SEQ ID NO: 3). PCR amplification in the absence of reverse transcriptase activity may be accomplished by chelating manganese and magnesium ions as described in (Lanford et al., 1995, J. Virol. 69:8079–8083). The amplified product, which spans nucleotides 15–274 of the 5'-NTR of HCV may be quantitated by Southern blotting using a detectably labeled probe against a region internal to the primers.

Liver tissue obtained by biopsy or from a sacrificed animal may be evaluated for HCV replication and for histopathological changes. Biopsy may be performed by anesthetizing the chimeric animal with intramuscular injections of ketamine (40 mg/kg) and xylazine (5 mg/kg), cleaning the abdominal area with alcohol and betadine wipes, making an incision in the abdominal wall to expose the liver, and collecting a sliver (weighing at least approximately 10 mg) of liver tissue. Afterward, 100 U of sterile thrombin (or another therapeutically effective amount, as needed) may be administered locally at the biopsy site followed by application of gel foam to inhibit bleeding, the abdominal wall may be closed with dissolvable sutures, and the skin may be closed with nylon sutures. Viral replication may be quantitated by measuring the amount of negative strand template HCV RNA in liver RNA (prepared, for example, as set forth in Chomczynski and Sacchi, 1987, Anal. Biochem. 162:156–159), using rTth RT-PCR (Lanford et al., 1995, J. Virol. 69:8079–8083). To assess liver histology, liver tissue may be fixed and sectioned and stained with hematoxylin-eosin or trichrome to evaluate, respectively, inflammation or fibrosis. A standardized scoring method, such as Knodell scoring (Knodell et al., 1981, Hepatology 1:531), may be used. The presence or absence of neoplastic lesions may be evaluated.

To determine the optimum conditions for producing an HCV infected chimeric animal, the time course of serum aminotransferases AST and ALT, alkaline phosphatase levels, and viral RNA loads may be plotted as a function of time and the minimum number of viral equivalents required to sustain an infection determined. Levels of detectable HCV RNA in the serum of an animal may be used as an indicator of the chronicity of infection.

Potential problems associated with the foregoing embodiment are as follows. First, the detection of negative strand HCV template as a measure of HCV replication may be problematic due to the requirement for amplification techniques and the possibility of inadvertent amplification of positive strand. The method of Lanford et al. (supra) using stringent conditions for priming of the RT-PCR and inactivation of the reverse transcriptase by chelation prior to PCR of the cDNA has been shown to reduce false amplification to $1/10^4$–$1/10^5$. Second, laboratory animals may harbor an endogenous virus which causes hepatitis (for example, as regards laboratory mice as hosts, the fact that mouse hepatitis virus may be found even in "pathogen free" environments makes it desirable to confirm that host mice are free of the virus, for example using a mouse virus screen as available from Microbiological Associates, Inc., Rockville, Md. (Carlson et al., 1989, J. Clin. Invest. 83:1183–1190)), where animals testing positive are not used as hosts. Third, infection may be improved by increasing the amount of human serum used in the inoculum.

A working example of a chimeric rat model of HCV infection is set forth in Example Section 13, infra.

5.3.2. HCV Model Produced by Infectious Plasmid

In a related embodiment, infection may be introduced by HCV plasmid (Kolykhalov et al., 1997, Science 277:570–574) complexed to a liver-specific protein carrier, such as AsOR-PL or AsORlysine-VSVG, where AsOR-PL is asialoorosomucoid polylysine and AsORlysine-VSVG is asialoorosomucoid covalently linked to L-lysine methyl ester and a synthetic 25 amino acid peptide of the VSVG protein. The DNA-protein complex may be formed by slowly adding protein conjugate in 25 microliter aliquots to DNA in 0.15M NaCl with continuous vortexing at room temperature. After 30 minutes of incubation at room temperature absorption at 260 nm, 340 nm and 400 nm may be measured to detect complex formation. Complexes may be filter sterilized by passage through a 0.22 micron filter. An amount of DNA/protein complex may then be administered. About 10–50 micrograms of the DNA/protein complex in 0.5 milliliters sterile saline may then be injected into the tail vein of a mouse, and 100–500 micrograms of DNA/protein complex in a volume of 1–5 mls may be injected into a rat.

5.3.3. HCV Model Produced by Transplanting Infected Hepatocytes

As an alternative to producing HCV infection by inoculation with infected serum, infection may be produced by transplanting HCV infected hepatocytes into a chimeric animal. Although the infected hepatocytes may be introduced during colonization with human cells, it is preferred that they be introduced into chimeric livers having a substantial population of human hepatocytes. In one non-limiting set of embodiments, the chimeric animal is a mouse transgenic for a gene whose product is selectively toxic to hepatocytes, such as the albumin promoter/urokinase gene or the albumin promoter/HSV-TK gene. In another set of non-limiting embodiments, the chimeric animal is a rat tolerized and transplanted with Huh7 cells.

Infected human hepatocytes may be obtained as described in Lieber et al., 1996, J. Virol. 70:8782–8791. Using appropriate pathogen-containment procedures, human liver specimens may be obtained from HCV-infected liver transplant recipients. An apical piece of liver covered on three sides by capsule may be perfused with buffer without calcium and then with collagenase in perfusion buffer with calcium. Hepatocytes may then be pelleted by low speed centrifugation. Non-parenchymal cells may be separated from parenchymal hepatocytes by metrizamide gradient centrifugation. The viability of isolated hepatocytes may be evaluated by trypan blue exclusion. Hepatocytes may be resuspended in Williams medium at about $10^7$ cells per milliliter.

The infected hepatocytes may then be introduced into the liver of a chimeric animal, for example a chimeric animal whose liver comprises at least about 20 percent, preferably at least 50 percent, more preferably at least 80 percent) human hepatocytes. The infected hepatocytes may be introduced by intrasplenic injection. Where the animal is a mouse, hepatocytes may be introduced by anesthetizing the animal with ketamine (90 mg/kg)/xylazine (10 mg/kg), and then, under aseptic conditions, making a 2–3 millimeter incision in the left paracostal area, exposing the spleen. The spleen may then be exteriorized and infected hepatocytes may be injected slowly into the spleen parenchyma. Gel foam may be used to achieve hemostasis, the spleen may be restored into the body cavity, and the wound may be sutured closed. Monitoring of the resulting infected animals for serconversion, viral load, serum levels of protein markers of liver function, and histopathology may be performed as described in section 5.3.1. Further, these methods may be adapted for use in larger animals.

5.3.4. Use of HCV Models

Chimeric animal models of HCV infection may be used not only to study the biology of HCV, but also to identify agents that may prevent or inhibit HCV infection and/or replication. For example, to determine whether a test agent inhibits infection by HCV, the effect of the agent on preventing infection when administered prior to or contemporaneously with injection of infected serum may be evaluated. Similarly, the effect of a test agent administered during the course of infection may be assessed. Parameters useful in determining the effectiveness of test agent would include whether and when the test animal seroconverts with respect to HCV, the viral load, the ability of serum from the animal to infect other animals, blood levels of proteins/enzymes associated with liver function and/or hepatocyte viability, and liver histology.

5.4. Chimeric Animals as a Source of Hepatocytes for Liver Reconstitution

The present invention further provides for the use of chimeric animals as a source of human hepatocytes for liver reconstitution in a second host subject. Such reconstitution may be used, for example, to (i) produce a "next generation" chimeric non-human animal; (ii) introduce genetically modified hepatocytes for "gene therapy" of the second host subject; or (iii) replace hepatocytes lost as a result of disease, physical or chemical injury, or malignancy in the second host. Human hepatocytes collected from a chimeric animal are said to be "passaged".

For any of these applications, liver tissue from a chimeric animal may be used to produce a cell suspension and then human hepatocytes may be separated from non-human hepatocytes and other cells. The liver tissue may be processed as set forth above to produce a suspension of hepatocytes. As a non-limiting specific example, where the chimeric animal is a mouse or rat, hepatocytes may be prepared by the following method, adapted from Seglen, 1976, "Preparation of rat liver cells", Methods Cell Biol. 13:29. Briefly, a chimeric mouse or rat may be anesthetized with ketamine/xylazine, its abdomen may be shaved and decontaminated, the peritoneal cavity may be opened by incision, the inferior vena cava may be cannulated, the portal vein may be divided and the suprahepatic vena cava may be ligated. Then, the liver may be perfused in situ with calcium free balanced salt solution at 5 ml/min for five minutes at 37° C., followed by perfusion with 0.05% collagenase (e.g., type IV, from Sigma Chemical Co.) in 1% albumin and balanced salt solution for 20 minutes. The liver may then be transferred to a Petri dish, and minced to produce a cell suspension, from which hepatocytes may be collected by passage through a 60–80 micron nylon mesh. The collected cells may then be washed three times in RPMI 1640 or Williams E medium with 10% fetal bovine serum, and then centrifuged at 35×g for five minutes at 4° C. Hepatocytes may be purified through a metrizamide gradient and resuspended in RPMI 1640 or Williams E medium.

Human hepatocytes may be separated from non-human cells using fluorescence activated cell sorting techniques and an antibody which selectively binds to human hepatocytes, for example but not by way of limitation, an antibody that specifically binds to a class I major histocompatibility antigen. Suitable antibodies would include but not be limited to anti-human HLA-A,B,C, PharMingen catalogue #32294X or #32295X, FITC mouse κb, PharMingen catologue #06104D (PharMingen, San Diego, Calif.) See, for example, the procedure described in Markus et al., 1997, Cell Transplantation 6:455–462.

Human hepatocytes may be passaged through cell transplantation of tolerized host animals, using the techniques set forth above. In this manner, cells obtained from an initial human donor may be utilized in a multitude of chimeric animals and over an extended period of time, potentially reducing the variability that may be encountered in chimeric animals produced using hepatocytes obtained from diverse hosts.

Passaged human hepatocytes may also be used for gene therapy applications. In the broadest sense, such hepatocytes are transplanted into a human host to correct a genetic defect. The passaged hepatocytes need not, but are preferably derived originally from the same individual who is to be the recipient of the transplant. However, according to the invention, hepatocytes from a different individual may alternatively be used.

As a specific, non-limiting example, a patient suffering from intermittent acute porphyria, caused by a genetic defect in the expression of uroporphyrinogen I synthase, may benefit from transplantation of human hepatocytes harvested from a chimeric animal of the invention, where the transplanted cells are genetically normal in their expression of that enzyme. The recipient would be "matched" for transplantation antigens with the original donor, or be treated with immunosuppressive therapy. For such applications, chimeric animals prepared from a wide diversity of individual donors could provide the advantage of constituting a "living library" of differentiated hepatocytes having various transplantation antigen profiles, thereby obviating the need for waiting until liver tissue from a genetically suitable donor becomes available.

Preferably, however, the original donor and eventual recipient of passaged hepatocytes are the same person, thereby eliminating the need for immunosuppression. For gene therapy applications, (i) hepatocytes may be harvested from the subject, (ii) the desired genetic construct may be introduced into those hepatocytes, (iii) the resulting genetically engineered human hepatocytes may be used to tolerize a host animal to their presence, (iv) construct-carrying hepatocytes may be introduced into the tolerized animal such that its liver is colonized, and then, once expanded in number, (v) the transgenic hepatocytes may be harvested from the chimeric animal and (vi) reintroduced into the subject. A genetic construct may be introduced into the human hepatocytes by any standard method, including, but not limited to, transfection with naked DNA, microparticles or liposomes, or infection with a viral vector, such as an adenoviral vector, an adeno-associated vector, or a retroviral vector. Hepatocytes used for colonization may be enriched for cells containing the desired construct, for example, by selection by culture conditions, antibody/FACS methods, etc. which eliminate cells lacking the construct.

Alternatively, the hepatocytes may be used to colonize the liver of a tolerized animal prior to or contemporaneous with the introduction of the desired transgene via a gene therapy vector. This approach may be more problematic because the host animal could develop an immune response directed toward either the vector or vector-transformed hepatocytes.

In further embodiments, human hepatocytes passaged through a chimeric animal of the invention may be used to reconstitute liver tissue in a subject as a prelude or an alternative to liver transplant. As a specific non-limiting example, a subject suffering from progressive degeneration of the liver, for example, as a result of alcoholism, may serve as a donor of hepatocytes which are then maintained, through one or several generations, in one or more chimeric animal. As a result of maintenance in such animal(s), the number of hepatocytes is expanded relative to the number originally harvested from the subject (it may be preferable to use larger animals to produce greater numbers of cells). At some later date, when the subject's liver has deteriorated to a medically hazardous condition, hepatocytes passaged in the chimeric animal(s) may be used to reconstitute the subject's liver function. As a second non-limiting example, passaging hepatocytes may be used not only to expand the number of hepatocytes but also to selectively remove hepatocytes that are afflicted with infectious or malignant disease. Specifically, a subject may be suffering from hepatitis, where some but not all of the hepatocytes are infected and infected hepatocytes can be identified by the presence of viral antigens on the cell surface. In such an instance, hepatocytes may be collected from the subject, and non-infected cells may be selected for passaging in one or more chimeric animal, for example by FACS. Meanwhile, aggressive steps could be taken to eliminate infection in the patient. Afterward, the subjects liver tissue may be reconstituted by hepatocytes passaged in a chimeric animal. An analogous method could be used to selectively passage non-malignant cells from a patient suffering from a primary or secondary (e.g. metastatic) liver malignancy. Thus, the chimeric animals of the invention may be used as a means of purging unwanted hepatocytes from a human subject.

6. EXAMPLE

Preparation of Rars having Chimeric Livers

6. 1. Survival of Human Hepatocytes in Rats Tolerized by Intraperitoneal Injection To tolerize hosts for hepatocyte transplantation, human hepatocytes obtained from Clonetics Corp. were suspended at a concentration of $10^6$ cells/ml saline and sonicated. Laparotomies were performed to expose the gravid uteri of pregnant rats and sterile filtered sonicates equivalent to $10^4$ hepatocytes in 10 μl were injected into groups of three fetuses each. A control received only the same volume of normal saline. Within 24 hrs of birth, transplantation of hepatocytes were performed by the method of Marucci et al., 1997, Hepatol. 26: 1195–1202. An incision was made at the left paracostal area, the spleen was visualized and $2\times10^7$ hepatocytes in 100 1 sterile medium were injected slowly into the spleen. To evaluate the status of immune tolerance, two experiments were performed: a) mixed lymphocyte assays and b) repeat transplantation challenges.

6.2. Mixed Lymphocyte Assays

For mixed lymphocyte assays, spleens from intrafetally injected animals were removed six weeks after birth, and spleen cells were isolated as described by Henry and Watson (1980, "Preparation of Spleen Cells" section 2.9, in *Selected Methods in Cellular Immunology*, Mishell and Shiigi, eds., WH Freeman and Co., p. 65). Assays were performed according to the method of Bradley (1980, "Mixed Lymphocyte Responses" section 6.3, in *Selected Methods in Cellular Immunology*, Mishell and Shiigi, eds., WH Freeman and Co., p. 162) in which spleen cells were used as responder cells and human hepatocytes (identical to those transplanted but treated with 2000 R of X-irradiation to prevent proliferation) were used as stimulator cells. Human hepatocytes should not stimulate lymphocyte proliferation in spleen cells from immunotolerant animals, but should in cells from non-tolerant animals.

Spleen cells, $7\times10^5$ cells per assay, from fetuses previously injected intraperitoneally as described above with hepatocyte lysates alone, lysates followed by hepatocytes after birth, or controls were mixed with $3\times10^5$ X-irradiated stimulator hepatocytes. Controls consisted of spleen cells from saline treated fetuses alone, and those same cells plus irradiated spleen cells from non-treated animals. Cells were pulsed with 1 μ$C^3$[H]-thymidine (specific activity 5 Ci/mmole) at 37° C. for 72 hours, and then harvested by TCA precipitation onto Whatman glass fiber filters, washed and scintillation counted. All assays were performed in quadruplicate, and the entire experiment done in duplicate. The results are expressed as means±S.D. in units of cpm/$10^6$ responder cells in FIG. 1.

FIG. 1 shows that spleen cells from animals that did not receive hepatocyte lysate when they were fetuses incorporated approximately 5,200 cpm/$10^6$ cells when stimulated with irradiated human hepatocytes. In contrast, stimulation of spleen cells derived from animals that did receive human hepatocyte lysate when they were fetuses was significantly less (less than 1000 cpm/$10^6$ cells [p<0.002]) than that observed using cells from animals that did not receive lysate. In fact, cells derived from animals injected with lysates resulted in stimulation that was no more than background levels of spleen cells alone. Irradiated hepatocytes alone (without spleen responder cells) had no significant radioactive incorporation confirming that the irradiation substantially blocked any contribution to the observed radioactive uptake.

These data indicate that spleen cells removed 6 weeks after birth from rats previously injected as fetuses with human hepatocyte lysates are not significantly stimulated to proliferate by the presence of human hepatocytes. At this time point, human albumin is still strongly detectable in serum in the tolerized animals. Together, the data indicate that immune tolerance to human hepatocytes was achieved.

6.3. Rechallenge with Additional Hepatocyte Transplantations

As further evidence for immune tolerization, groups of rats previously tolerized and transplanted as described above were subjected to a repeat transplantation. If the rats were not rendered immunologically tolerant to human hepatocytes, a second transplantation of human cells would be expected to evoke an anamnestic response and rapid rejection of those cells. To evaluate that possibility, rats tolerized intrafetally and transplanted with human hepatocytes at birth as described above were given a repeat transplantation of $2\times10^6$ cells 6 weeks after the first. Serum was assayed for human serum albumin using a specific anti-human albumin antibody and analyzed by Western blots as shown in FIG. 2.

In FIG. 2, lane 1 contains 40 ng of human serum albumin standard, and lane 2 shows that there was human albumin still present in substantial concentration in serum at 6 weeks after an initial cell transplantation. After a second injection of human cells the amount of serum albumin increased 24 hrs later (lane 3), and continued to rise at least 8 days after the repeat dose of cells (lane 4). Animals that had not been tolerized (received only a fetal injection of saline) had no detectable human serum albumin even after a repeat transplant of human hepatocytes under identical conditions and assayed at the same time point (8 days; lane 5). These data suggest that human hepatocytes did not survive in non-tolerized animals. In contrast, in those animals that were tolerized, human hepatocytes not only survived each of two successive inoculations, but also maintained function as evidenced by serum albumin production.

6.4. Survival of Human Hepatocytes

Seventeen day old normal Sprague-Dawley rat fetuses were given lysates of $0.5\times10^5$ human hepatocytes by transuterine inoculation into the peritoneum under transillumination. Following birth, $2\times10^6$ normal human hepatocytes were injected into the spleen. This is known to result in near total migration of transplanted hepatocytes to the liver (Attavar, et al., 1997, Hepatol. 26: 1287–1295). At weekly intervals, animals were bled via their tail veins and human serum albumin was detected as a function of time by Western blot analysis using a specific affinity purified rabbit anti-human albumin antibody (FIG. 3). At the conclusion of the study, animals were sacrificed and liver slices stained with anti-human albumin antibody and developed with a Texas red secondary antibody. Cells were visualized using a Zeiss confocal scanning microscope, model CLSM4 10 and images were captured as shown in FIG. 4.

FIG. 3 shows a representative Western blot of the collected rat sera. Lane 1 contains standard molecular weight markers, lanes 2–4 contain human serum albumin at 50 μg, 10 μg and 1 μg, respectively. Lanes 5–9 contain sera from a tolerized rat transplanted with human hepatocytes at one week (lane 5), two weeks (lane 6), three weeks (lane 7), four weeks (lane 8) and five weeks (lane 9) after transplantation. All sera contain a band corresponding to the band seen for standard human albumin. The level of human albumin remained stable through 5 weeks. Transplantation of human IMR-90 fibroblasts under identical conditions failed to produce any detectable serum albumin (lane 10). The affinity purified anti-human albumin antibody was specific for human albumin as 50 μg of standard rat serum albumin (lane 11) did not produce a band corresponding to human serum albumin (lanes 2–4).

FIGS. 4A–D shows a representative immunofluorescence study of a liver section taken from 1 of 4 rats 3 weeks after injection with human hepatocyte lysate in utero, followed by intrasplenic injection of human hepatocytes. Immunocytochemistry was performed with primary antibody for human albumin, or rat albumin as a control, and Texas red-coupled secondary antibody. Panel A shows anti-human albumin antibody staining of rat liver without human hepatocyte transplantation. Panel B shows rat livers 3 weeks following injection with human hepatocyte lysate in utero and intrasplenic injection of human hepatocytes (1 day after birth) stained with anti-human albumin antibody and Texas Red second antibody. Panel C shows the same section as depicted in B, but without second antibody. Panel D shows a section of control rat liver after only transuterine injection of human hepatocyte lysate developed with anti-human albumin antibody and Texas Red second antibody. Anti-human albumin staining of liver transplanted with human hepatocytes, but without prior injection with hepatocyte lysate was essentially the same as that shown in Panel A. There was no anti-human albumin staining of normal (non-transplanted rat liver) in Panel A. Cells with fluorescent cytoplasm are seen in Panel B, after both in utero lysate injection and human hepatocyte transplantation. This staining was not due to intrinsic fluorescence as there was no signal without second antibody as shown in Panel C. Finally, Panel D shows that the fluorescence could not be due to human albumin from the hepatocyte lysate alone. All 3 other animals injected with human hepatocyte lysate in utero and intrasplenic injection of human hepatocytes showed similar results.

FIG. 5 is a photomicrograph of the same section of rat liver as depicted in FIG. 4B, 3 weeks after intrasplenic injection of human hepatocytes, here stained with hematoxylin and eosin. The human hepatocytes cannot be distinguished from the rat cells, and there appears to be no inflammation or other evidence of rejection.

FIGS. 6A–D shows the results of an immunofluorescence study performed six weeks after cell transplantation in tolerized animals. Aggregates of cells staining positive for human albumin were present in a tolerized rat that had received a human hepatocyte transplant, panel A. The same section without second antibody, panel B; or no antibody at all failed to produce a fluorescent signal, panel C. Furthermore, a liver section from a non-tolerized animal that had received a human hepatocyte transplant also produced no stained cells after 6 weeks, panel D. Scanning many fields also showed that most of the positive cells at 6 weeks were in groups, while sections taken at 2 weeks showed scattered single cells, predominantly. Because the injected cell suspensions were predominantly single cells, and because the fluorescence data at 2 weeks showed predominantly isolated single cells, the finding of groups of cells at 6 weeks suggests that the human cells transplanted into tolerized rats not only survived, but proliferated to some extent in the host liver environment.

7. EXAMPLE

Induction of Tolerance to Human Hepatocytes by Intrathymic Injection in Neonatal Rats Injection of human hepatocytes was performed according to the method of Fabrega et al., 1995, Transplantation 59:1362–1364. $10^2$ human hepatocytes in 5 µl sterile medium were injected into the thymuses of 1–2 hour old newborn rats. Five days following intrathymic injection, $10^5$ human hepatocytes in 200 µl sterile medium was injected into the spleen (Marucci et al., 1997, Hepatol. 26:1195–1202). Blood was collected by tail vein puncture at the time of intrathymic injection and at weekly intervals following intrasplenic injection of hepatocytes and assayed for human albumin by Western blot analysis.

A representative Western blot of serum from one of 6 animals after intrathymic tolerization, followed by transplantation of human hepatocytes, is shown in FIG. 7. Lane 1 contains 10 ng standard human albumin; lane 2 contains 10 ng standard rat albumin and lanes 3–7 contain sera taken at the indicated times after transplantation of human hepatocytes. The data show that human albumin production increased until about 5 weeks and then remained stable. The other five animals had shown similar results.

8. EXAMPLE

A Model for Hepatitis B Virus Infection

8.1 Purification of HBV Particles from HEPG2 2.2.15 Cells

To test the possibility of infection of human hepatocytes in vivo, infectious HBV particles were prepared from the HepG2 2.2.15 cell line (obtained from Dr. George Acs, Mt. Sinai School of Medicine, NY) which contains an integrated tandem repeat genome of HBV ayw strain. The cell line actively secretes infectious virus into the medium (Sells et al., 1988, J. Virol 62:2836–2844). Culture medium from HepG2 2.2.15 was clarified by centrifugation at 5,000 rpm, 4° C. for 30 min. The supernatant was layered on a 5 ml 25% sucrose cushion in TEN buffer (150 mM NaCl, 20 mM Tris-HCl, pH 7.4) and centrifuged at 25,000 rpm for 16 hrs at 4° C. The resulting pellet was resuspended in TEN buffer, applied onto a 20–50% continuous CsC 1 gradient, and centrifuged at 35,000 rpm for 16 hrs at 4° C. Fractions with buoyant densities between 1.24 g/ml and 1.28 g/ml containing HBV virus were collected, dialyzed against TEN and sterile filtered through 0.22 µ filters.

8.2 Infection of Human Hepatocytes Transplanted into Tolerized Rat Hosts

To determine whether human hepatocytes in rat liver could be infected with human hepatitis virus, one week after human hepatocyte transplantations, tolerized rats were given intrasplenic injections of $10^5$ hepatitis B viral particles (purified from HepG2 2.2.15 cells as described above) in 50 µl. Control animals tolerized but without human hepatocyte transplants, and tolerized transplanted animals without HBV were used as controls. Liver sections were removed by liver biopsy at 1 week, and partial hepatectomy at 6 weeks and 14 weeks post HBV treatment and analyzed as described below.

8.3 Identification of the Presence of Human Liver Cells and HBV Infection

Figure 8A:
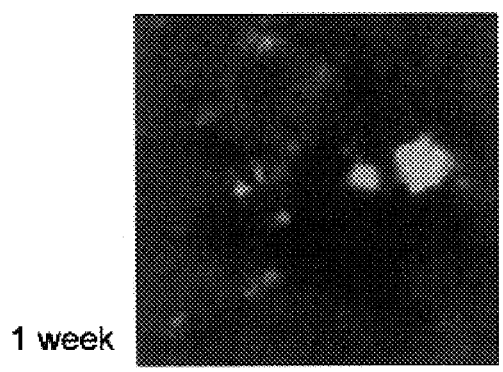
Figure 8B:
Figure 8C:
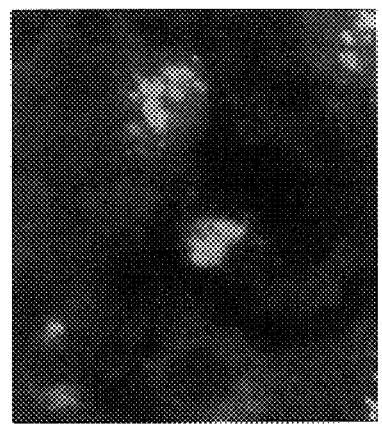
Figure 8D:
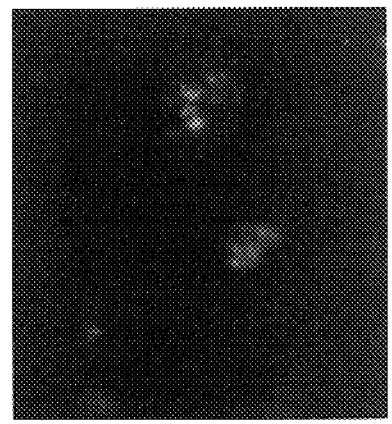
Figure 8E:
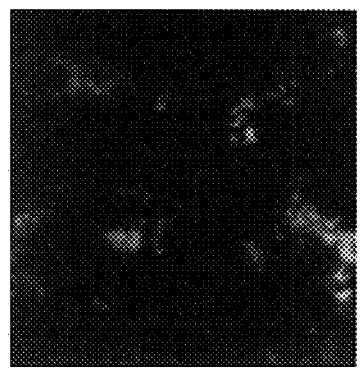
Figure 8F:
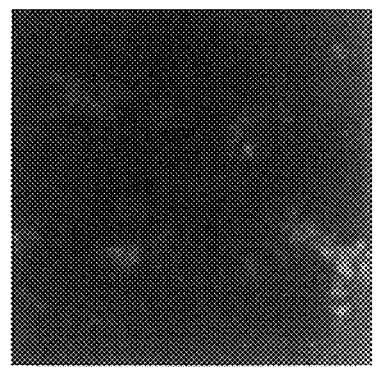

To identify and quantify human hepatocytes in host liver, immunohistochemical staining for human albumin was used. Visualization of cells infected with HBV was similarly achieved by immunohistochemical staining for Hepatitis B Surface Antigen (HBsAg). Liver tissues were flash frozen in liquid nitrogen immediately following removal. Samples were prepared according to the method of Osborne and Weber (1982, Meth. Cell Biol. 24:97–132) with minor modifications. Liver cryosections 6 µm thick were fixed in 4% paraformaldehyde for 15 min at 25° C., and washed 3 times with phosphate buffered saline (PBS) pH 7.2. Liver sections were quenched with 10% non-fat milk in PBS for 30 min at 25° C. followed by successive incubations with 1/1000 dilution of rabbit anti-human albumin (Sigma). Identical sections were stained with 1/1000 dilution of goat anti-HBV surface antigen (DAKKO). Each section was incubated for 2 hrs at room temperature. Between each primary antibody incubation, liver sections were exposed to 10% non-fat milk in PBS containing 0.05% NP-40 and 3 times with 10% non-fat milk in PBS alone. Texas red-conjugated anti-rabbit antibody (1/100 dilution) was used to develop anti-human albumin and FITC conjugated anti-goat (1/100 dilution) antibody was used to develop anti-HBsAg. Sections were incubated with the second antibodies for 30 min at 25° C. Following 3 washes with 10% non-fat milk in PBS, and a final PBS wash, sections were treated with anti-fade 2.5% 1/4-diazobicyclo-[2.2.2]-octane (DABCO) (Sigma), covered with cover slips and stored at 20° C. in light-proof boxes. Immunofluorescence of liver sections were visualized with Zeiss Scanning laser confocal microscope (Model LSM-410, Carl Zeiss, New York) using 63× objective. Frozen sections of chimeric liver were incubated with antibodies against human albumin and HBV surface antigen to detect the presence of human albumin and HBV proteins. Human albumin was detected with Texas red conjugated secondary antibody and HBV surface antigen detected with the use of FITC-conjugated second antibody. FIGS. 8A–F clearly demonstrates that both human albumin, left panels 8A, 8C and 8E, and HBV surface antigen, right FIGS. 8B, 8D, and 8F, were clearly detectable within cells in livers of tolerized rats transplanted with human hepatocytes followed by HBV treatment at 1 week (FIGS. 8A and 8B); 6 weeks (FIGS. 8C and 8D); and 14 weeks (FIGS. 8E and 8F). Furthermore, the staining for HBsAg appeared to present only in cells that also stained for albumin. However, many cells that contained albumin were also positive for HBV. In a liver sample obtained 14 weeks after injection with HBV, FIGS. 9A–H shows that albumin stained cells were only found in animals that had been tolerized and had received transplanted human hepatocytes (FIGS. 9A and 9C). Animals without human cell transplants that received HBV had no albumin signal (FIG. 9E). Only tolerized animals that received human hepatocyte cell transplants prior to infection had HBsAg staining (FIG. 9B). As expected, the same animals without HBV infection failed to show any HBsAg staining indicating that the signal seen in FIG. 9B was not a non-specific artifact. Furthermore, animals that had no human cells, but did receive HBV injection also had no HBsAg signal (FIGS. 9E and 9F). The data indicate that injected virus had already been completely cleared by the time the liver sample was obtained and that the signal observed in row 1 was due to the infection of cells, and was not an artifact of circulating injected HBV. FIGS. 9G and 9H show that, in the same samples as depicted in FIGS. 9A and 9B, but without primary antibody, there was no signal corresponding to either albumin (FIG. 9G) or HBsAg (FIG. 9H), indicating the staining was not due to non-specific binding of second antibody to the tissue specimens.

8.4 Historical Evaluation of Livers Exposed to HBV

To determine whether exposure of human hepatocyte transplants to HBV could result in a histological hepatitis in vivo, serial slide sections were stained with hematoxylin and eosin and examined in a blinded fashion by a pathologist. The results, discussed below, are shown in FIGS. 13A–C and 14A–C.

8.5 Assessment of Function of Transplanted Human Hepatocytes

Because albumin synthesis is a selective function of hepatocytes, levels of albumin mRNA were used to determine the activity of transplanted human cells in host liver. To accomplish this, specific primers for human and rat (control) albumin were used. HBV mRNA was detected similarly. Total RNA was extracted from 100 mg liver tissue with acid guanidinium thiocyanate according to the method of Chomczynski and Sacci (1987, Anal. Biochem. 162: 156–159). Poly A+RNA was isolated from total RNA by the method of Aviv and Leder (1972, Proc. Natl. Acad. Sci. USA 69: 1408–1412). RNA was reverse transcribed and amplified by polymerase chain reaction according to the method of Berchtold (1989, Nucl. Acids Res. 17: 453) with some modifications. Briefly, 10 µg total RNA or 1 µg polyA$^+$ RNA was mixed with 2 pmol of random primer (Gibco/BRL, Gaithersburg, Md.) at 70° C. for 15 min, and then cooled on ice. Two hundred units of Moloney Murine Leukemia Virus reverse transcriptase (Gibco/BRL, Gaithersburg, Md.) was used to reverse transcribe the RNA for 50 min at 42° C. Reaction was stopped by heating to 70° C. for 15 min, after which the cocktail was chilled on ice and treated with 10 µg RNase A at 37° C. for 20 min.

From the total cDNA, polymerase chain amplification of human albumin was performed using, as antisense primer, 5'-CCTTGGTGTTGATTGCCTTTGCTC-3' (SEQ ID NO: 4) and as sense primer, 5'-CATCACATCAACCTCTGTCTGACC-3' (SEQ ID NO: 5). If present, the albumin cDNA would generate a characteristic 315 bp fragment of the human albumin gene spanning nucleotides 176–491. For rat albumin, an antisense primer 5'-ATAGTGTCCCAGAAAGCTGGTAGGG-3' (SEQ ID No: 6) and a sense primer: 5'-CGGTTTAAGGACTTAGGAGAACAGC-3' (SEQ ID No: 7) were used to generate an expected 400 bp fragment of the rat albumin gene spanning nucleotides 104–504. To search for the presence of HBV in liver, an antisense primer 5'-ATCTTCTGCGACGCGGCGATGGAGATC-3' (SEQ ID No: 8) and a sense primer 5'-CTCTGCTGGGGGGAATTGATGACTCTAGC-3' (SEQ ID NO: 9) were used to generate a characteristic 355 bp fragment of the ayw HBV genome spanning nucleotides 2079–2434. One third of the total cDNA was mixed with 100 pmol of amplification primers and 2.5 U Taq polymerase and amplified at 1 cycle at 94° C. for 3 min, then for 38 cycles of 94° C. for 1 min, 55° C. for 1 min, and 72° C. for 1 min; and then 5 min. The PCR products were analyzed on 1.0% agarose gels in Tris-Borate-Acetate buffer.

FIG. 10, lanes 1 and 2 show that the RT-PCR products of albumin from rat and human livers can be completely distinguished from each other based on electrophoretic mobility. Lane 4 shows RNA from HepG2 2.2.15 cells demonstrating a strong level of albumin synthesis in these cells. In tolerized animals that had human hepatocyte transplants, the rat albumin signal had the same intensity in cells infected with HBV (lanes 5 and 6) compared to those which were not (lanes 7 and 8). However, the human albumin mRNA signal in cells infected with HBV (lanes 5 and 6) appeared to be increased compared to non-infected cells (lanes 7 and 8). As expected, control animals that had no human hepatocyte transplants, but were administered HBV, had no detectable human albumin signal (lanes 9 and 10).

A time course of the levels of human albumin and HBV message is shown in FIG. 11. Compared to albumin RNA from human liver cells in the upper panel, lane 3, and from HepG2 2.2.15 cells lane 4, human albumin messenger RNA signal at 315 bp was easily detectable at one week after HBV infection, lane 5; with at least equal signal from week 6 and 14, lanes 6 and 7, respectively.

FIG. 11, bottom panel shows that HBV RNA could be detected in livers by the presence of a 355 bp band at 1 week after injection, lane 5. The intensity appeared to increase slightly at 6 weeks, lane 6; and remained strong at 14 weeks, lane 7, after HBV inoculation. The same primers were used to amplify HBV RNA from a human liver cell line HepG2 2.2.15 that continually produces HBV and was used as the source of HBV viral particles for the infections. FIG. 12 shows that HBV RNA could not be detected in livers of tolerized rats that did not receive hepatocyte transplantation, but received HBV (lanes 9, 10), indicating that the signal was not due to residual injected HBV.

FIGS. 13A–C depicts slides of livers from tolerized rats, transplanted with human hepatocytes and infected with HBV, at low power (20×). FIG. 13A shows that liver, one week after infection, has normal architecture for that stage in life and no evidence of inflammatory cell infiltration. However, after 6 weeks (FIG. 13B), foci of necrosis and mononuclear cell infiltrates can be seen. FIG. 13C shows substantial mononuclear inflammation after 14 weeks with an increase in Kupffer cells as well. FIGS. 14A–C shows that at high power (40×), the infiltrates are more easily seen to be to be mononuclear cells surrounding areas of necrosis at 6 weeks (FIG. 14B). At 14 weeks, the inflammation extends into the surrounding parenchyma (FIG. 14C).

8.6. Detection and Quantitation of HBSAG in Rat Serum

To follow the course of infection, levels of HBsAg in rat serum were measured using an EIA kit for HBV surface antigen (Abbott Labs, Abbott Park, Ill.) according to the manufacturer's protocol. Briefly, 10 μl serum in 190 μl saline was mixed with anti-HBs (mouse) monoclonal antibody coated beads and 50 μl of horseradish peroxidase conjugated anti-mouse secondary antibody and incubated at room temperature for 16 hours. Then the incubation solution was removed and the beads were washed six times with 10 ml distilled water, and the beads were transferred to clean assay tubes and incubated with 300 μl of freshly prepared o-phenylenediamine substrate and quantitated using a spectrophotometer at 492 nm. Assays were done in triplicate and the results (see Tables 1, 2 and 3, third column) were expressed as means±S.D. in units of pg/ml serum.

8.7. Detection of Serum Alanine Aminotransferase (ALT)

To determine whether HBV infection was associated with any liver damage, was collected from rats as a function of time after injection, and serum ALT values mined in triplicate from 10 μl serum using a commercial ALT detection kit (Sigma). All assays were done in triplicate and results are expressed as means±S.D. International Units IU/ml.

Group 1 animals were treated by (i) intrafetal injections with human hepatocyte lysates into the peritoneums at 17 days post-conception; (ii) intrasplenic saline injection at birth; and iii) one week later, purified HBV harvested from a human hepatoma cell line was administered by intrasplenic injection.

TABLE 1

| Time Post-HBV Injection (days) | ALT (IU/L) | HBsAg (pg/ml) |
| --- | --- | --- |
| 0 | 28 ± 15 | Not detectable |
| 1 | 44 ± 20 | Not detectable |

TABLE 1-continued

| Time Post-HBV Injection (days) | ALT (IU/L) | HBsAg (pg/ml) |
| --- | --- | --- |
| 8 | 22 ± 12 | Not detectable |
| 10 | 25 ± 10 | Not detectable |

As shown in Table 1, animals that received no tolerization or human hepatocytes, but were injected with HBV had no significant changes in ALT as a measure of liver cell damage, or detectable HBsAg in the serum even as soon 1 day after injection of HBV through at least 10 days. The data confirm that HBV does not cause hepatic damage in rats and that the is rapidly cleared from the circulation.

Animals in Group 2 were treated by (i) intrafetal injection with human hepatocyte lysate into the peritoneums at 17 days post-conception; (ii) intrasplenic injection of 2 million human primary hepatocytes at birth; and (iii) 1 week post hepatocyte transplantation, saline was injected intrasplenically.

TABLE 2

| Time Post-HBV Injection (days) | ALT (IU/L) | HBsAg (pg/ml) |
| --- | --- | --- |
| 0 | 25 ± 15 | Not detectable |
| 1 | 22 ± 20 | Not detectable |
| 8 | 30 ± 5 | Not detectable |
| 10 | 25 ± 16 | Not detectable |

As shown in Table 2, animals tolerized with human hepatocytes that received human hepatocyte transplants, but no HBV, also had normal ALT and undetectable HBsAg throughout the 10 days. Thus, without inoculation with HBV, there was no serological evidence of hepatotoxicity or circulating HBV.

Animals in Group 3 were treated by (i) transuterine injection into the peritoneum at 17 days post-conception with primary human hepatocyte lysate; (ii) intrasplenic injection of 2 million human primary hepatocytes at birth; and (iii) HBV was injected intrasplenically at 1 week post-hepatocyte transplantation.

TABLE 3

| Time Post-HBV Injection (days) | ALT (IU/L) | HBsAg (pg/ml) |
| --- | --- | --- |
| 0 | 22 ± 15 | Not detectable |
| 1 | 47 ± 10 | 0.2 ± .01 |
| 4 | 86 ± 15 | 0.1 ± .05 |
| 8 | 132 ± 15 | 0.4 ± 0.1 |
| 10 | 179 ± 20 | 0.5 ± .15 |

As shown in Table 3, in this group which was tolerized and received human hepatocytes and HBV, ALT levels were normal until day 4 when the level doubled to 86 IU/L. By day 10, the ALT had doubled again to 179 IU/L. The HBsAg was detectable at 0.1–0.2 pg/ml through day 4. However, the levels doubled to 0.4 and reached 0.5 pg/ml day 10. These data suggest that viral antigen and likely viral levels increase early in the process, and are followed by liver cell damage. This is supportive of an inflammatory process triggered by the injection of HCV, but only in animals that have human hepatocytes.

EXAMPLE

Further Studies Demonstratinf that Human Hepatocytes Transplanted into Genetically Immunocompetent Rats are Susceptible to Infection by Hepatitis B Virus In Situ

9.1 Materials and Methods

9.1.1 Animals

Sprague-Dawley female rats, 15 days pregnant, were obtained from Charles River Co. Inc. (Wilmington, Mass.), maintained on 12 hr light-dark cycles, and fed ad lib with standard rat chow. All animal procedures were approved by Institutional Animal Care and Use Committee and conformed to USDA and NIH animal usage guidelines.

9.1.2 Cells

Primary human hepatocytes were obtained from Clonetics Corp. (Walkersville, Md.) and kept frozen at $-70°$ C. For use in experiments, frozen cells were thawed at $37°$ C., washed with Hepatocyte Culture Medium (Clonetics Corp) containing 5 mg/ml insulin and 0.39 µg/ml dexamethasone (SingleQuote, Clonetics Corp) and spun at 50×g, 10 min, $4°$ C. Microscopic examination of the recovered cells revealed a viability of 65% as determined by trypan blue exclusion, and parenchymal hepatocyte composition of greater than 90%. For injections, cells were suspended in 500 µl phosphate buffered saline (PBS), and used immediately. HepG2 2.2.15 human hepatoblastoma cells that constitutively produce infectious HBV particles (Sells et al., 1987, Proc. Natl. Acad. Sci. U.S.A. 84: 1005–1009) were maintained in DMEM containing 10% FBS as described previously (Sells et al., 1987, Proc. Natl. Acad. Sci. U.S.A. 84: 1005–1009).

9.1.3. Induction of Immune Tolerance to Human Hepatocytes

The abdominal cavities of pregnant rats were exposed by laparotomy under sterile conditions, and the gravid uteri trans-illuminated. Primary human hepatocytes, $10^5$ cells in 10 µl PBS, were injected with a Hamilton syringe, using sterile technique through the uterine wall into the peritoneal cavities of fetal rats 17 days post-conception, under a dissecting microscope. Control animals were treated identically except that they were injected with saline instead of cells.

9.1.4 Mixed Lymphocyte Essays

To assess immune tolerance, mixed lymphocyte assays were performed according to the method of Schwartz et al. (1975, J. Immunol. 115: 1330–1338). In these assays, responder spleen cells were stimulated to proliferate by exposure to stimulator cells if they are not tolerant to those cells. Two weeks after birth, spleens from rats that had intrafetal injections of human hepatocytes were removed, and aliquots of cells prepared as responder cells. Stimulator cells consisting of $3\times10^5/0.5$ ml human hepatocytes gamma irradiated with 2000 R to inhibit proliferation, were mixed with $1.0\times10^6$ responder spleen cells/0.5 ml from tolerized and saline-treated control animals. An aliquot of spleen cells from normal untreated rats, as well as irradiated hepatocytes alone, mixed with an equal volume of buffer were used to measure background proliferation under identical conditions. Cell suspensions were pulsed with 1 µCi of [$^3$H]-thymidine [80.0 Ci/mmol, Amersham Life Science] and then incubated for 72 hrs at $37°$ C., under 10% $CO_2$, in RPMI medium containing 5% fetal bovine serum. Cells were then harvested onto Whatman glass fiber filters, washed once with cold PBS pH 7.0, then cold 10% trichloroacetic acid, and finally cold 95% ethanol. The radioactivity retained by the filters was measured in a scintillation counter. All experiments were performed in triplicate, and thymidine incorporation results expressed as means±S.D. in units of cpm/$10^6$ cells.

9.1.5. Transplantation of Human Hepatocytes

Within 24 hrs after birth, groups of tolerized neonatal rats were transplanted with human hepatocytes by injection into the spleens according to the method of Marucci et al. (1997), Hepatology 26: 1195–1202). Incisions were made at the left paracostal areas, the spleens visualized and $2\times10^6$ human primary hepatocytes in 100 µl sterile medium were injected slowly into the organ.

9.1.6 Purification of HBV from HepG2 2.2.15 Cells

Infectious HBV particles were harvested from the medium of HepG2 2.2.15 cells similar to the method described in Liang et al., 1993, J. Clin. Invest. 91: 1241–1246. In brief, culture medium from HepG2 2.2.15 cells was centrifuged at 5000 rpm (4000×g) at $4°$ C. for 30 min. The clarified medium was layered on a 25% sucrose cushion in Tris-EDTA-NaCl (TEN) buffer, and centrifuged at 25,000 rpm (100,000×g) for 16 hrs at $4°$ C. The pellet was resuspended in TEN buffer and applied onto 20–50% continuous cesium chloride gradient at 35,000 rpm for 16 hrs at $4°$ C. Fractions with buoyant densities between 1.24 g/ml and 1.28 g/ml contained HBV virus, and were collected, dialyzed against TEN, sterile filtered through 0.22 µ filters before injection. The amount of virus present was determined by dot blots using a DNA fragment corresponding to nt 0-1802 of the HBV genome, as a probe, and quantitated by using serial dilutions of full length HBV DNA excised from padwR9 (Liang et al., 1993, J. Clin. Invest. 91: 1241–1246) to generate standard curves.

9.1.7 HBV Inoculation of Rats

One week following human hepatocyte transplantation, groups of tolerized rats were inoculated with $10^5$ HBV particles in 100 µl TEN buffer by intrasplenic injection. Controls consisted of tolerized neonatal rats from the same litter that did not receive human hepatocyte transplantation, but were also given identical HBV inoculations, as well as tolerized rats from the same litter that received saline instead of human hepatocytes, but no HBV.

9.1.8 Visualization of Human Liver Cells and HBV Infection

Immunohistochemical analysis for the presence of human albumin and hepatitis B virus surface antigen (HBsAg) were performed according to the method of Osborne and Weber (1982, Meth. Cell Biol. 24: 97–132) with minor modifications. Liver tissues were flash frozen in liquid nitrogen immediately following removal from animals, and 5 µ thick liver cryosections were fixed in 4% paraformaldehyde for 15 min at $25°$ C., washed several times with PBS pH 7.2. Liver sections were quenched with Blotto (10% non-fat milk in PBS) for 30 min at $25°$ C. followed by successive or single incubations with 1/1000 dilution of anti-human albumin (Sigma) and 1/1000 anti-HBV surface antigen (Dakko) for 2 hrs at room temperature. Between each primary antibody incubation, liver sections were washed with blotto containing 0.5% Tween-20. Texas Red-conjugated anti-rabbit antibody at 1/1000 dilution (Amersham Life Science) was used to develop anti-human albumin, and FITC-anti-mouse antibody at 1/1000 dilution (Boehringer Mannheim) for anti-HBsAg. Sections were incubated with the second antibodies for 30 min at 25° C. and treated with antifade 2.5% 1/4-diazobicyclo-[2.2.2]-octane (DABCO) (Sigma), covered with cover slips and stored at −20° C. in light proof boxes. Immunofluorescence of liver sections was analyzed using a Zeiss Scanning laser confocal microscope (Model LSM-410) using 63× objective.

9.1.9 In Situ Hybridization

To identify cells containing human albumin, and HBV DNA in transplanted human hepatocytes, in situ hybridization was performed according to the method of Pardue (1985, in *Nucleic Acid Hybridization: A Practical Approach*, eds. B. D. Hames, B. D. and Higgins, S. E. (IRL Press, Oxford), pp. 179–202). Briefly, 5 μ frozen liver sections were fixed with 4% paraformaldehyde, washed with PBS and digested with pronase. Sections were incubated with a [$^{32}$P]-labeled 355 bp fragment of HBV cDNA labeled with specific activity of $4 \times 10^8$ cpm/μg. Sections were hybridized for 4 hrs at 37° C. Following hybridization and washing, sections were exposed to Kodak film emulsion for one week, developed, and counterstained with toluidine blue. Radioactivity of the sections were visualized by dark field illumination using a Leitz Labor Lux S microscope using 40× objective. Tolerized rats without transplantation and inoculated with HBV, and untreated rats served as controls.

9.1.10 Detection of HBV DNA in Rat Serum

After inoculation with HBV, serum samples were collected weekly. To detect HBV DNA, DNA was extracted from 30 μl of rat serum, incubated with 100 μg/ml proteinase K in 0.05 M Tris—HCl, pH 8.0, 0.1M EDTA and 0.5% SDS, overnight at 55° C. DNA was purified by phenol-chloroform (Gross-Bellard et al., 1973, Eur. J. Biochem. 36: 32–38).

An antisense primer 5'-ATCTTCTGCGACGCGGCGATGGAGATC-3' (SEQ ID NO:8) and a sense primer 5'-CTCTGCTGGGGGGAATTGATGACTCTAGC-3' (SEQ ID NO:9) were used to generate an expected 355 bp fragment of adw HBV genome spanning nt 2079–2434. One third of total cDNA was mixed with 100 pmol of amplification primers and 2.5 U Taq polymerase, and amplified at 1 cycle 94° C. for 3 min; 38 cycles of 94° C. for 1 min, 55° C. for 1 min, 72° C. for 1 minute; and the final elongation reaction at 72° C. for 5 minutes. The PCR products were analyzed on 1.0% agarose gels in Tris-Borate-Acetate buffer and visualized by ethidium bromide staining.

9.1.11 Quantitation of HBV in Rat Liver and Serum

To measure the HBV viral load in rat serum, DNA was extracted from 30 μl of rat serum using the method mentioned above and fixed onto nylon membranes (Amersham). The amount of HBV viral DNA was quantitated by DNA dot-blot hybridization (Scotto et al., 1983, Hepatology 3: 279–284). Serial dilutions of standard adw HBV DNA from 1 million copies to one thousand copies were used to determine the number of HBV viral particles/ml serum. Blots were hybridized overnight at 60° C. to [$^{32}$P]-dATP-labeled full length HBV DNA probe excised from padwR9 plasmid (Liang et al., 1993, J. Clin. Invest. 91: 1241–1246). Following hybridization and washing, filters were visualized by exposure to XAR film (Kodak).

9.1.12 Detection and Quantitation of HBsAG in Serum

Levels of HBsAg in rat serum were measured as a function of time after inoculation using an enzyme-linked immunoassay kit for HBV surface antigen (Abbott Labs) according to the manufacturer's protocol. Ten μl serum in 190 μl saline was mixed with anti-HBsAg (mouse) monoclonal antibody-coated beads and 50 μl of horse radish peroxidase-conjugated anti-mouse secondary antibody and incubated at 25° C. for 16 hrs. The incubation solution was removed and the beads washed with 10 ml distilled water, and then incubated with 300 μl of o-phenylenediamine substrate. Antigen was quantitated using a spectrophotometer at 492 nm. Assays were done in triplicate, and the results expressed as means±S.D. in units of pg/ml serum.

9.1.13 Assays for Replicative HBV DNA

To determine whether inoculated HBV produced progeny virus, covalently closed circular DNA was assayed by PCR using primers that amplify a region that spans the sequences of the plus strand that are incomplete in viral particles, but are converted to complete covalently closed circles upon infection. DNA was extracted from 20 mg of liver according to the method of Arrigo et al. (1989, J. Virol. 63: 4875–4881). The primers used were: sense GCCGGTCTG-GAGCAAAGCTCATCGG (SEQ ID NO:10) spanning nt 1306–1380 and antisense GGCGGTGTCTAG-GAGATCTCTGAC (SEQ ID NO:11) spanning nt 1981–2004 of adwHBV genome. After amplification, an anticipated 698 bp band was sought by agarose gel electrophoresis in the presence of ethidium bromide.

9.2 Results

FIG. 15, lane 3 shows that spleen cells from rats that had not been injected intrafetally with hepatocytes, were stimulated to proliferate, incorporating $6.0 \times 10^4 \pm 6 \times 10^3$ cpm [$^3$H]-thymidine/$10^6$ cells when exposed to (irradiated) human hepatocytes. In contrast, exposure of spleen cells from animals that were tolerized intrafetally with human hepatocytes, lane 4, resulted in a significantly [p<0.002] lower uptakes, $2.9 \times 10^4 \pm 10^3$ cpm/$10^6$ cells. This uptake was not significantly different from a background of spleen cells alone from rats injected intrafetally with only saline, in the absence of any stimulator cells, lane 1. Lane 5 shows that intrafetal hepatocyte injections alone, without subsequent hepatocyte transplantations were sufficient to induce tolerance as evidenced by a lack of a significant increase in proliferation in the presence of human hepatocytes. Finally, lane 2 shows that irradiated hepatocytes alone without spleen responder cells had no significant radioactive incorporation indicating that the vast majority of the observed uptake of radioactivity in mixtures of the two cell types was due to spleen cells. The data confirm that the dose of irradiation was sufficient to block significant hepatocyte proliferation.

To visualize human hepatocytes, cells producing human albumin were detected immunohistochemically with a Texas Red-conjugated second antibody. Similarly, cells containing HBsAg were detected with a FITC-second antibody in frozen sections of liver. FIGS. 16A–F shows that in representative liver sections taken 15 weeks after HBV inoculation, human albumin, FIG. 16A, and HBV surface antigen, FIG. 16B (serial sections) can be detected in cells with brightly stained cytoplasm. Cells positive for albumin were not uniformly distributed throughout the liver lobule, but appeared to be concentrated in groups of several cells each, interspersed between other areas that had few positive cells. Some of the cells, approximately 30%, stained positive for both albumin and for HBsAg. However, no cells that were positive for HBsAg, were completely negative for human albumin. As expected, livers from tolerized rats transplanted with human hepatocytes, but not inoculated with HBV were positive for human albumin only, FIG. 16C, and negative for HBV surface antigen, FIG. 16D. Control animals that received intrafetal tolerization, and not human hepatocyte transplantation, but were inoculated with HBV, were negative for both human albumin, FIG. 16E, and HBV surface antigen, FIG. 16F, indicating that the observed positive staining in FIGS. 16A and 16B was not due to non-specific or cross-reactions against rat albumin, other endogenous antigens, or injected HBV antigens.

Figure 17A:
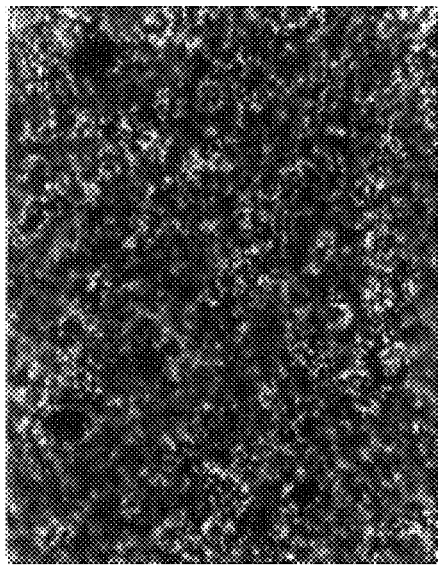
Figure 17B:
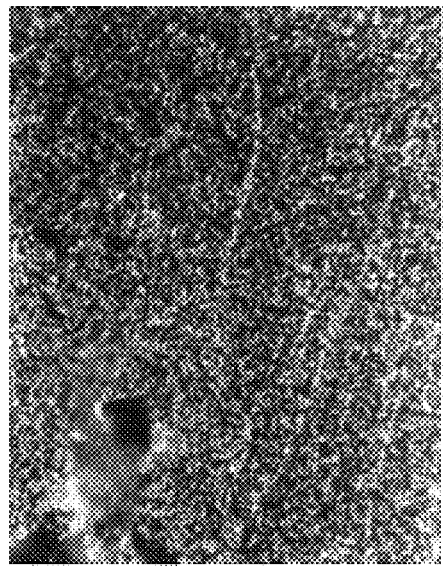
Figure 17C:
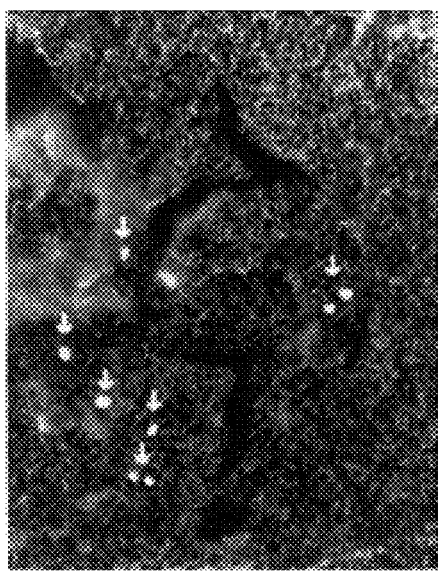
Figure 17D:
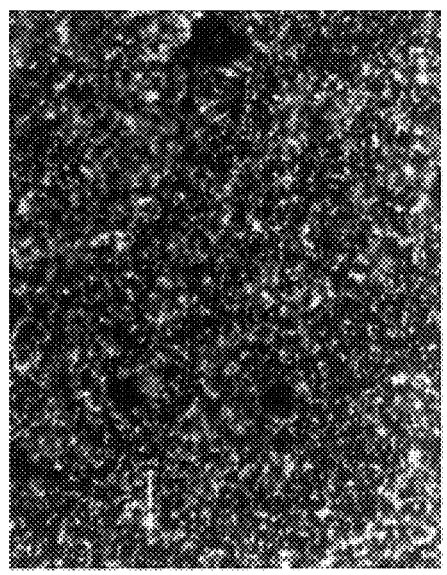

It is possible that the positive staining of cells detected in FIGS. 16A–F was due to uptake of antigen, but not HBV DNA. To determine whether that was the case, cells containing HBV DNA were sought by in situ hybridization. FIG. 17C shows that liver sections from rats that were tolerized, transplanted with human hepatocytes, and inoculated with HBV had multiple positive cells as evidenced by white spots on the negative (arrows). In contrast, control livers from rats tolerized, transplanted with human hepatocytes, but not inoculated with HBV, FIG. 17A, had no signal, indicating that the observed positive cells in FIG. 17C were not simply due to an artifact present in human cells. Similarly, rats that were tolerized, and not transplanted, but did receive HBV, FIG. 17B, also had no signal. Hence, the signal was not a residue of input HBV. Finally, FIG. 17D shows that, as expected, livers from rats that were neither transplanted nor exposed to HBV, failed to demonstrate any hybridization signal.

FIG. 18A shows that the presence of HBV DNA in serum was confirmed by the finding of an expected 355 bp fragment of the adw HBV genome spanning nt 2079–2434 generated by PCR. For PCR, the same primers were used to amplify HBV DNA from a human liver cell line HepG2 2.2.15 as a positive control, lane 3. The 355 bp fragment of HBV can clearly be detected in serum of two representative rats, lanes 4–6 and 7–9, respectively, both of which were tolerized, had human hepatocyte transplantation and HBV inoculation. Serum HBV DNA was detectable at 1 week after infection, lanes 4 and 7, and remained detectable through 15 weeks after inoculation, lanes 6 and 9. HBV DNA was not detected in serum from tolerized rats with human hepatocyte transplantation alone (with no exposure to HBV), lanes 10 and 11, in serum of two representative tolerized rats that did not receive human hepatocytes, but were exposed HBV, lanes 12–14 and 15–17, at 1, 5 and 15 weeks after HBV inoculation. FIG. 18B shows that serum HBV DNA quantitated by dot-blots from two representative rats transplanted with human hepatocytes had a mean value of 5000 copies/ml at 1 week, dots A2 and B2; 10,000 copies/ml at 5 weeks, dots A3 and B3; and increased to a mean of 50,000 copies/ml by 15 weeks after exposure, dots A4 and B4. In contrast, serum from tolerized animals with hepatocytes alone, dots C1 and D/1, and serum from tolerized animals infected with HBV alone, dots C2–4 and D2–4, showed no detectable HBV DNA at similar time points. HBV DNA was not found in serum of control untreated rats, dots A1 and B1.

To determine whether HBV replication could occur in human hepatocytes transplanted in rat livers, covalently closed circular HBV DNA was assayed using PCR primers specific to region of HBV genome that is incomplete in the plus strand of the viral particle, but is covalently closed upon HBV replication. FIGS. 19A–B shows that PCR detected a 698 bp band, corresponding to the expected size of nt 1306–2004 of a covalently closed circular adw HBV genome, in the livers, FIG. 19A lanes 4–5, and sera, FIG. 19B lanes 3–4, respectively, of two representative rats that were transplanted with human hepatocytes and infected with HBV, at 15 weeks after HBV inoculation. The same band was not detected in rats transplanted with human hepatocytes alone, and not exposed to HBV, in liver (FIG. 19A lane 6) or serum (FIG. 19B lane 5). No signal was found in tolerized rats not transplanted, but exposed to HBV, in liver (FIG. 19A lanes 7–8) or serum (FIG. 19B lane 6), indicating that the generated PCR fragment was not a non-specific product arising from the tolerization procedure, or the presence of residual input HBV, or non-specific amplification of a host sequence.

FIG. 20 shows that HBsAg was detectable in serum of transplanted and HBV inoculated rats, solid circles, by 24 hrs after inoculation, and increased to 0.75 pg/ml where levels remained relatively constant through the period of observation of 60 days. Control rats that were transplanted with human hepatocytes alone, and not exposed to HBV, open squares, or exposed to HBV in the absence of transplanted human hepatocytes, crosses, had no detectable antigen at any time point.

9.3 Discussion

Human hepatocytes previously infected with human viruses have been introduced into immunodeficient animals in the past. For example, hepatitis C virus-infected human liver has been transplanted into animals with ablated marrow reconstituted with SCID marrow (Galun et al., 1995, J. Infect. Dis. 172: 25–30). In another example, mice with ablated bone marrow, reconstituted with SCID bone marrow were transplanted with an HBV-infected human liver fragment under the kidney capsule (Ilan et al., 1999, Hepatology 29: 553–562). Because the liver specimen was transplanted en bloc, some human liver matrix and non-parenchymal cells accompanied the hepatocytes in the fragment. Therefore, some of the hepatocytes would have retained natural relationships to extracellular matrix and other human cells. In addition, the specimen was pre-infected with HBV. It is, therefore, not surprising that HBV viremia was found in the host following the transplantation. Brown et al. transplanted into RAG-2-deficient mice, immortalized human hepatocytes permanently transfected with an HBV genome and showed long term viremia in another example of an immunodeficient model (Brown et al., 2000, Hepatology 31: 173–181). In the experiments described herein, uninfected normal hepatocytes were separated from matrix, and as well as other human cells during the isolation procedure, and therefore, were transplanted into a completely unnatural environment. Nevertheless, the cells maintained a degree of function as evidenced by production of human albumin detected by immunohistochemistry. This is of interest because primary cultured hepatocytes are notorious for the rapidity with which they lose differentiated function and, indeed, are difficult to infect with HBV in vitro. The fact that the transplanted hepatocytes were susceptible to HBV infection suggests that the rodent liver environment, although foreign, is still sufficient for retention of this sensitive and particular property of human hepatocytes. The retention of function was also noted in a closely related study by Petersen et al. who transplanted woodchuck hepatocytes into a urokinase RAG-2 mouse and showed that the transplanted woodchuck cells could be infected by inoculation with WHV (Petersen et al., 1998, Proc. Natl. Acad. Sci. U.S.A. 95:310–315).

Because of the time frame involved in the above experiments, it is unclear whether the rat inoculations resulted in transient or chronic infections. The rat immune system does not become mature until approximately three weeks after birth. Thus, inoculation with HBV within 24 hrs of birth described here simulates perinatal infection in man. Human perinatal infections are common in regions of the world highly endemic with HBV, and in these cases, it has been observed that the likelihood of progression to chronicity is extremely high presumably due to immaturity of the immune system at the time of infection (Milich et al., 1995, Springer Seminars in Immunopathology 17:149–166). In addition, a mismatch exists between the human MHC and the rat immune system which could hamper clearance of virus and infected cells. These factors could increase the likelihood of development of chronic infection.

Injection of hepatocytes into the spleen was used as for convenient access to the liver. It has been shown previously the vast majority of hepatocytes so injected, migrate into the liver (Vroemen et al., 1986, Transplantation 42: 130–135), and exit the sinusoids to enter the host parenchyma (Parker-Ponder et al., 1991, Proc. Natl. Acad. Sci. U.S.A. 88:1217–1221). While the data provided herein indicate that numerous human hepatocytes were present in the host liver after transplantation, and that some of these cells also had HBV DNA and HBsAg after inoculation of the rats with HBV, the possibility of HBV infection of some of the human hepatocytes that remained in the spleen cannot be excluded. From previous reports, the number of cells would be expected to be less than 15% of that originally injected (Parker-Ponder et al., 1991, Proc. Natl. Acad. Sci. U.S.A. 88:1217–1221).

Tolerization was achieved by transuterine injection of human cells into fetal rat on the 17th day of gestation. This is similar to previous studies on mice, in which injection of foreign cells on the $14^{th}$ to $16^{th}$ day of gestation was found to result in tolerance to subsequent cardiac and skin grafts (Kline et al., 1994, Am. Thorac. Surg. 57:72–75). However, the pioneering work in mice and chicks in utero to attain acquired tolerance to foreign cells was done by Medawar and co-workers (Billingham et al., 1953, Nature 4379: 603–606). Although the exact mechanism of the tolerance is not exactly clear, clonal deletion of specific thymocytes (Pullen et al., 1988, Nature 335:796–801; McDuffie et al., 1988, J. Immunol. 141:1840–1847), and the involvement of major histocompatibility complex, H-2 (Laconi et al., 1998, Am. J. Pathol. 153:319–329) in suppressing the immune response to allogenic cells have been postulated to be involved.

10. EXAMPLE

Tolerization of Rats with Differentiated Hepatoblastoma Cells

10.1 Materials and Methods

10.1.1. Animals

Pregnant Sprague-Dawley rats, having a body weight of 250–300 gm, were maintained on 12 hour light-dark cycles and fed ad lib with standard rat chow.

10.1.2. Cells

Cryopreserved human primary hepatocytes were obtained from Clonetics Corp. (Walkersville, Md.) and kept in liquid nitrogen until use. Frozen cells were thawed, washed with human hepatocyte medium (Clonetics Corp.) plus 5 mg/ml insulin and 0.39 μg/ml dexamethasone, and then spun at 50×g for ten minutes at 4° C. Cell viability was measured by trypan blue exclusion staining (approximately 65 percent of the cells were viable, and 90 percent were parenchymal hepatocytes). Human hepatoblastom cell lines Huh7 and HepG2, human fibroblast IMR-90 and human kidney 293 cells were grown in Dulbecco Modified Eagle's medium ("DMEM") containing 10 percent fetal bovine serum ("FBS") and antibiotics.

10.1.3. Intrafetal Injection of Human Hepatocytes

At 15 to 17 days of gestation, groups of pregnant rats were anesthetized by intramuscular injections of ketamine (40 mg/kg body weight) and xylazine (5 mg/kg body weight). Laparotomies were performed under sterile conditions; gravid uteri were exposed and transilluminated by a high intensity lamp (Fiber-lite MI-150, Dolan-Jenner Industries, Lawrence, Mass.). Primary human hepatocytes or Huh7 or HepG2 cells, $1 \times 10^5$ cells in 10 microliters PBS, were injected through the uterine wall into the peritoneal cavities of rat fetuses using a sterile 200 μl Hamilton syringe with a 28 gauge beveled point needle (Hamilton Inc., Reno, Nev.).

10.1.4. Cell Transplantation

Within 24 hours of birth, newborn rats were placed on ice for 2–5 minutes. Then, under sterile conditions, left paracostal incisions were made, and primary human hepatocytes, Huh7 or HepG2 cells, $1 \times 10^7$ cells/ml in 200 μl PBS were injected over 30 seconds into the spleen by sterile Hamilton syringe.

10.1.5. Sample Collection

The tolerance of host animals toward human hepatocytes was assessed by mixed lymphocyte assays in which the proliferation of host spleen cells was measured after exposure to exogenous antigens (Schwartz et al., 1975, J. Immunol. 115:1330–1338). Briefly, spleens were removed from tolerized or control animals 1 week after cell transplantation or, for non-transplanted controls, one week after birth, and dispersed into RPMI-1640 medium (GIBCO-BRL) containing 5 percent FBS. Stimulator cells (primary human hepatocytes, Huh7, IMR-90 and 293 cells) were gamma-irradiated with 2,000 Rad to inhibit proliferation. Irradiated stimulator cells, 0.5 ml of a $3 \times 10^5$/ml cell suspension, were mixed with 0.5 ml of a $1 \times 10^6$/ml suspension of rat spleen cells pulse-labeled with 1 μCi of $^3$H-thymidine (80 Ci/mmol, Amersham Life Science) and then incubated at 37° C. under 5 percent $CO_2$ for 72 hours. After trichloroacetic acid ("TCA") precipitation, cells were harvested onto Whatman glass fiber filter papers (Whatman), washed successively with PBS, TCA and ethanol. Filter papers were counted in a scintillation counter (Tri-CARB 4530, Parkard). Spleen cells from untreated rats as well as stimulator cells incubated alone served as controls. All experiments were performed with triplicate animals, and the results are expressed as means±S.E. in units of cpm/$10^6$ cells.

10.1.6. Detection of Human Albumin in Rat Liver

To detect human hepatocytes that survived transplantation in rat livers, human albumin gene sequences were sought as specific markers using a 5' primer (5'-CTGGTCTCACCAATCGGG-3') and a 3' primer (5'-CTGGTCTCACCAATCGGGGG-3'). Genomic DNA extracted from Huh7 cells served as a positive control.

Genomic DNA from untreated rats and from non-transplanted rats were used as negative controls.

10.1.7. Quantitation of Human Albumin DNA

To quantify the number of human hepatocytes present in rat livers, dot blots using probes specific for the human albumin gene were performed by modifying the method of Kafatos (1979, Nucl. Acids Res. 7:1541–1552) with a $^{32}$P-labeled 1750 bp BamHi/BsteII human albumin DNA fragment excised from palb$_3$, a plasmid containing the complete human albumin gene (Wu et al., 1991, J. Biol. Chem. 266:14338–1442). All asays were performed in triplicate, and the results were expressed as means±S.E. Genomic DNA from known numbers of Huh7 cells was measured in an identical fashion.

10.1.8. Detection of Human Albumin mRNA in Rat Livers

To determine whether transplanted human hepatocytes retained liver-specific transcription, the presence of human albumin mRNA was evaluated by RT-PCR after extraction according to the method of Chomczynski (1987, Anal. Biochem. 162:1 56–159), using the following primers:
sense 5'-CCTTGGTGTTGATTGCCTTGCTC-3'(SEQ ID NQ:4);
antisense 5'-CATCACATCAACCTCTGGTCTCACC-3' (SEQ ID NO:5);
and the presence of rat albumin mRNA was evaluated using the primers:
sense 5'-CGGTTTAGGGACTTAGGAGAACAGC (SEQ ID NO:7); and antisense 5'-ATAGTGTCCCAGAAAGCTGGTAGGG-3'(SEQ ID NO:6'). The expected size of PCR products for human and rat albumin mRNA are 315 and 388 bp, respectively.

10.1.9. Detection of Human Albumin in Rat Liver

Sixteen weeks post-transplantation, groups of rats were sacrificed and their livers were sectioned into 5 micron thick slices in tissue freezing medium (Triangle Biomedical Sciences, Durham N.C.). Immunofluorescence staining was performed using the method of Osborn (1982, Methods Cell Biol. 24:97–132) using monoclonal mouse anti-human albumin antibody (Sigman, St. Louis, Mo.) and goat anti-mouse IgG second antibody conjugated with Texas Red (Amersham Pharmacia Biotech). Immunohistochemical staining for human albumin was done according to the method of Kieran (*Histological and Histochemical Methods: Theory and Practice*, Oxford: Butterworth Heinemann, 1990). Tissue samples were examined using confocal laser scanning microscopy (LSM-410, Zeiss, Germany).

10.1.10. Assays for Human Albumin in Rat Serum

To measure human albumin in rat serum, Western blotting was performed in a manner similar to the method of Gershoni (1982, Anal. Biochem. 124:396–405) using monoclonal mouse anti-human albumin antibody (Sigma, St. Louis, Mo.) and rabbit anti-mouse IgG second antibody conjugated with horseradish peroxidase ("HRP"; Sigma, St. Louis, Mo.). The signal was detected by an enhanced chemiluminescence method (ECL kit, Amersham) and exposed to film.

10.2. Results

Mixed lymphocyte assays were used to detect changes in immune response as a result of intra-fetal injections. In these assays, spleen (responder) cells taken at week 1 after birth were mixed with irradiated stimulator cells (primary human hepatocytes or controls consisting of Huh7 differentiated human hepatoblastoma cells, IMR-90 human fibroblasts, or 293 human kidney cells). FIG. 21, lane 1 shows that spleen cells from animals that were not injected with hepatocytes intrafetally, incubated alone (without any stimulator cells) had baseline uptake of 5,200±400 cpm/10$^6$ cells. Irradiated hepatocytes incubated alone only took up 800±360 cpm/10$^6$ cells, as shown in lane 2. In contrast, spleen cells having the same origin as those in lane 1 (from rats with no intrafetal injection) but subsequently exposed to irradiated human hepatocytes (lane 3) were stimulated to take up 39,000±5700 cpm/10$^6$ cells, a 7.5-fold increase. However, when spleen cells from rats that had intrafetal injection of primary human hepatocytes were subsequently exposed to irradiated primary human hepatocytes, lane 4, they were not stimulated, as uptake was only 5000±500 cpm/10$^6$ cells.

To determine whether the lack of stimulatory effect was hepatocyte-specific, spleen cells from animals injected intrafetally with primary hepatocytes were exposed to human IMR-90 fibroblasts. In contrast to hepatocyte stimulator cells, the spleen cells were stimulated by the fibroblasts, taking up 51,700±5,300 cpm/10$^6$ cells, lane 7. In another control, uptake in spleen cells from rats either intrafetally injected with hepatocytes (lane 6) or not (lane 8) was also stimulated by 293 human kidney cells. Irradiated IMR-90 (lane 9) and 293 cells (lane 10) incubated alone had negligible uptake, indicating that the contribution of these cells could not account for the observed increases in uptake results found in lanes 5 and 7.

To determine whether transformed human hepatocytes could also be used to induce immunological tolerance, Huh7 and HepG2 human hepatoblastoma cell lines were compared to primary human hepatocytes in terms of induction of tolerance. FIG. 22 shows that spleen cells from rats not injected intrafetally with hepatocytes and subsequently exposed to primary hepatocytes (lane 1), Huh7 cells (lane 2) or HepG2 cells (lane 3) all had uptake ratios significantly and substantially greater than cells from rats intrafetally injected and subsequently exposed to the corresponding cells (lanes 4,5 and 6, respectively).

Figure 23A:
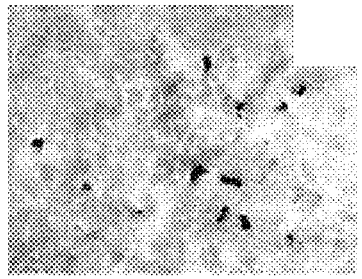
Figure 23B:
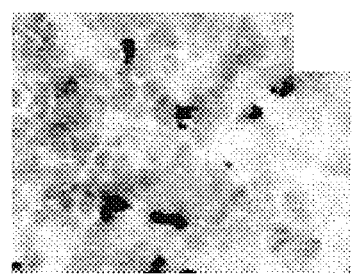
Figure 23C:
Figure 23D:
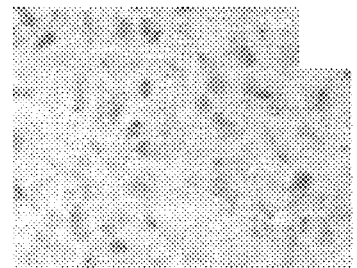
Figure 23E:
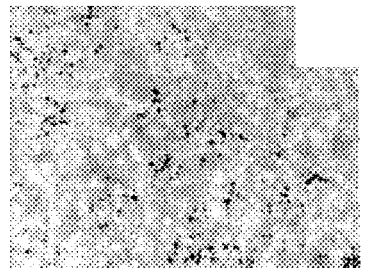
Figure 23F:
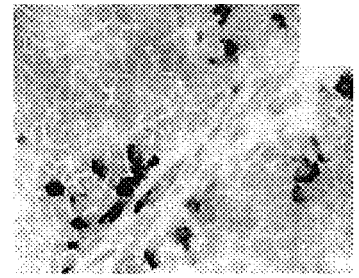

Because cell lines are a more accessible source of hepatocytes than liver, the differentiated hepatoblastoma cell line Huh7 was used as a source of hepatocytes for rat tolerization and transplantation, and the persistence of transplanted cells in rat liver was confirmed immunohistochemically using an antibody directed toward human albumin. As shown in FIGS. 23A and B, staining was detectable in rat livers on day 1 after transplantation, mostly in single cells with occasional pairs, and fairly evenly distributed throughout the parenchyma. In the livers of rat pups seven days after birth, clusters of two and three cells were visible and single cells expressing human albumin were less common, as shown in FIGS. 23E and F. No human albumin was detectable in livers of rats that were tolerized with Huh7 without subsequent Huh7 transplant (FIGS. 23C and D), confirming that the antibody was indeed specific for human albumin and lacked cross-reactivity with endogenous rat albumin.

Figure 24A:
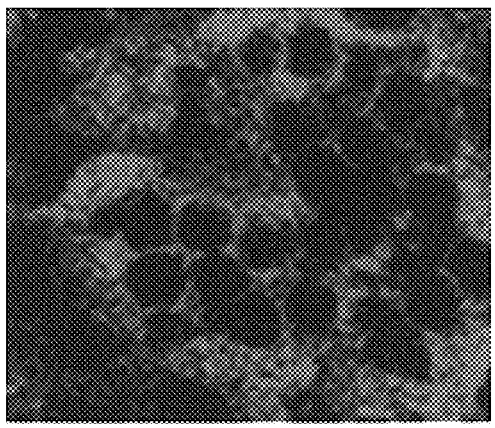
Figure 24B:
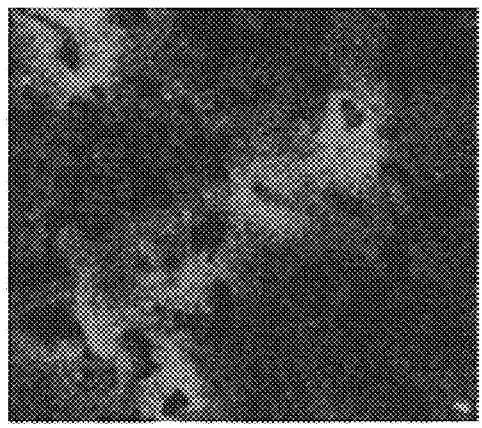
Figure 24C:
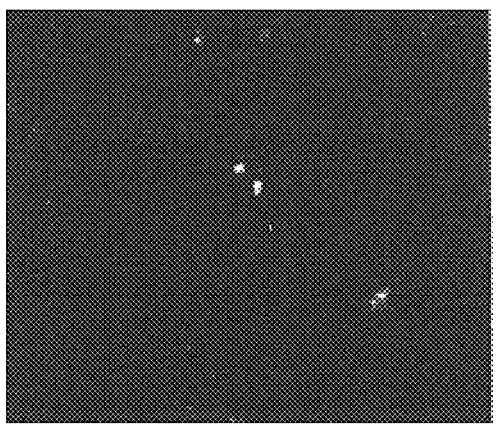
Figure 24D:
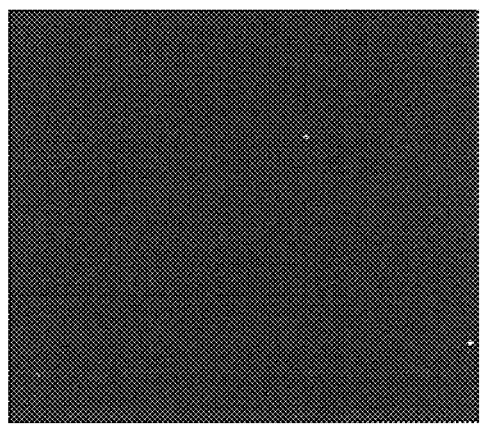

Laser scanning confocal microscopy was used to visualize transplanted hepatocytes by staining with monoclonal antibody against human albumin. FIG. 24B shows that in livers of tolerized rats transplanted with human hepatocytes, human albumin was detected at week 16 post-transplantation. In livers of tolerized rats without transplant, no staining was detected (FIG. 24C). Lack of staining in rat liver sections exposed to secondary antibody alone (FIG.

24D) demonstrated that staining was not an artifact caused by non-specific interaction with second antibody. As expected, liver sections stained with monoclonal goat anti-rat albumin antibody exhibited positive signals for rat albumin in virtually every parenchymal cell in the rat liver.

Figure 25:
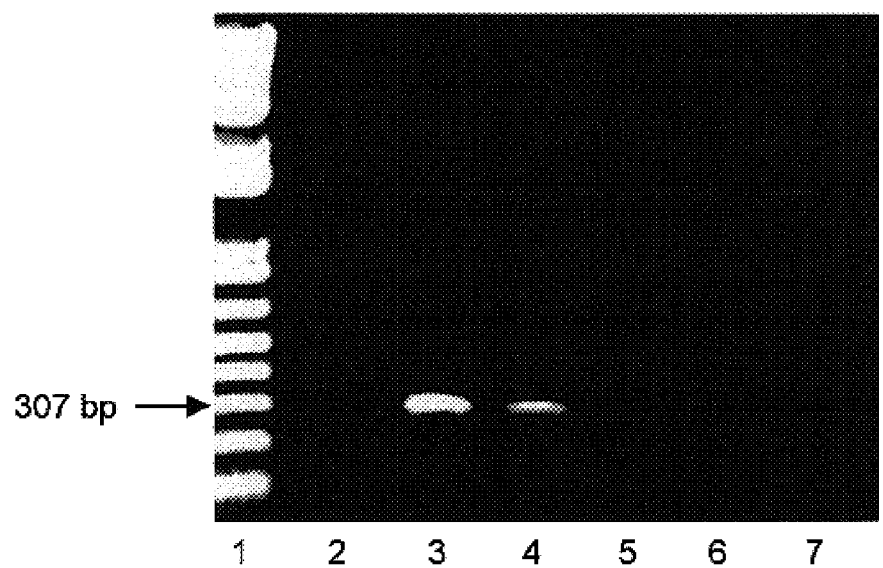

To estimate the number of human hepatocytes present in rat liver transplanted with primary human hepatocytes, human albumin DNA sequences were detected by amplification of rat liver genomic DNA by PCR. Lanes 3–5 of FIG. 25 show human albumin DNA extracted from $10^4$, $10^3$ and $10^2$ Huh7 cells, respectively. PCR produced the expected 307 bp products with decreasing intensities of signals. DNA from a rat intrafetally injected with primary human hepatocytes and transplanted with those cells (lane 6) produced a band at the expected position. In contrast, a littermate intrafetally injected with primary human hepatocytes, but not transplanted, produced no detectable human albumin DNA signal (FIG. 25, lane 7). Bands at the bottom of the gels are due to excess primers. Neonatal rats sustained intrasplenic transplantation of human hepatocytes well, with a mortality rate of about 5 percent.

To quantitate the amount of human albumin gene present, dot blotting for human albumin DNA was performed. FIG. 26A, upper row, shows that liver samples from a representative liver of a rat intrafetally tolerized and subsequently transplanted with primary human hepatocytes generated positive signals for human albumin DNA at 6 weeks and 16 weeks post-transplantation, with little obvious change in signal between the time points. In contrast, a littermate tolerized with human hepatocytes, but not transplanted (FIG. 26A, lower row) generated no signals at the same time points indicating that the human albumin signal detected in the upper panel was not due to residual DNA from the tolerization procedure or cross-reactivity with rat sequences. FIG. 26B shows that plasma $palb_3$ was loaded in serial dilutions to provide human albumin DNA standards.

Based on the amount of human albumin DNA in 10 μg rat liver DNA, the number of surviving human hepatocytes was calculated to be $2.5 \times 10^5$ cells per whole adult rat liver at 16 weeks post-transplantation. The ratio of human to rat hepatocytes that were present, 16 weeks post-transplantation, was calculated to be approximately 1 human cell per $6 \times 10^3$ rat hepatocytes.

To assess albumin gene transcription in rat livers, RT-PCR of albumin mRNA was performed. FIG. 27A shows that human albumin mRNA extracted from Huh7 cells was detected by RT-PCR by the presence of a product with the expected size of 315 bp. As expected, the same sample failed to generate a signal when rat albumin primers were used, indicating that the human primers were specific for the detection of human albumin mRNA (FIG. 27A, lane 7). In tolerized rats 16 weeks after human hepatocyte transplantation, human albumin mRNA was also detected as a 315 bp band (lane 4). However, no human albumin mRNA was detected in either (i) a littermate intrafetally injected with primary hepatocytes which did not receive a transplant (lane 5) or (ii) a littermate receiving neither tolerization nor transplantation (lane 2). As controls, a band corresponding to the rat albumin product of 388 bp was demonstrated in mRNA of (i) a rat which had received neither tolerization nor transplantation (lane 6); (ii) a rat tolerized and transplanted with primary human hepatocytes, 16 weeks after transplantation (lane 8); and (iii) a rat tolerized with human hepatocytes which did not receive a transplant (lane 9). As standards, RNA extracts from Huh7 cells were amplified with primers for human albumin to produce 315 bp products (lanes 10–12).

The transcriptional activity of transplanted human hepatocytes as a function of time was measured over the experimental period of 16 weeks. FIG. 27B, lane 3 shows that human albumin mRNA extracted from Huh7 cells in culture and detected by RT-PCR yielded a product with the expected size of 315 bp. Human albumin mRNA levels from rats were not obviously different at weeks 2, 6 and 16 after transplantation (FIG. 27B, lanes 4, 5 and 6, respectively) suggesting that, within the limits of the assay, the function of transplanted human hepatocytes, at least with regard to albumin production, remained unchanged for at least 16 weeks.

FIG. 28 shows Western blots of serum from a representative rat tolerized and transplanted with primary human hepatocytes. A band with migration corresponding to 56 kd, the expected size of human serum albumin (as indicated by the standard in lane 1) was found one week post-transplant (lane 3) and remained detectable at 2 and 3 weeks post-transplant (lanes 4 and 5, respectively). These data indicate that human hepatocytes can be transplanted and survive in the livers of intrafetally tolerized rats, and remain sufficiently active to secrete detectable amounts of human serum albumin into the circulation.

11. EXAMPLE

Repopulation of Transplanted Human Hepatocytes in Tolerized Rat Liver Using Retrorsine Retrorsine, a pyrrolizidine alkaloid, is metabolized by liver cells to a DNA alkylating intermediate. It has been used by other investigators to selectively eliminate adult liver cells. The rationale for using retrorsine in our project was that when retrorsine is given to rats tolerized with human hepatocytes, the resulting death of host rat liver cells would stimulate a regenerative response among transplanted human hepatocytes. The human hepatocytes would be expected to proliferate under these conditions. Because transplantations are done in newborn animals, the objective of the first experiment was to assess host liver cell death by retrorsine at this age. New born rats were given 2 different doses of retrorsine at varying time intervals.

The results of the experiments were as follows. Two doses of 30 mg/kg retrorsine given 2 weeks apart (published protocol) were lethal for newborn rats. There were no surviving rats after the second dose. One dose of retrorsine at 30 mg/kg was not sufficient to kill all newborn rate liver cells. There were BrdU positive liver cells in this group of treated rats indicating that there were some surviving liver cells undergoing regeneration. Two doses of 12 mg/kg retrorsine given 2 weeks apart at week 1 and week 3 were not lethal. 100% of newborn rats survived this treatment. BrdU labeling showed dividing cells in the livers of treated animals.

12. EXAMPLE

Evidence of proliferation of Transplanted Human Hepatocytes in Livers of Tolerized Rats Mutant Nagase rats that have barely detectable levels of albumin were tolerized in utero with Huh7, a differentiated human liver cell line. At day one after birth, rats were transplanted with $10^7$ Huh7 cells and give daily IP injections of 100 mg/kg T3 (thyroid hormone) to stimulate liver cell growth. At day 4 after transplantation, rats were given a 2 hr pulse of BrdU, livers removed and immunohistochemical staining was done for both human albumin and BrdU on the same frozen section. The presence of human albumin would be indicative of the presence of human liver cells and the presence of BrdU indicative of cell proliferation.

Figure 29A:
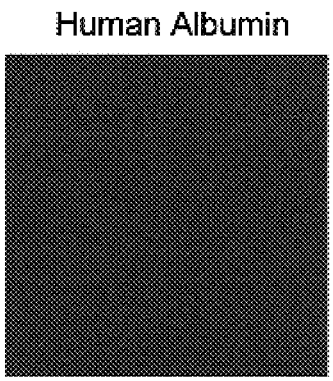
Figure 29B:
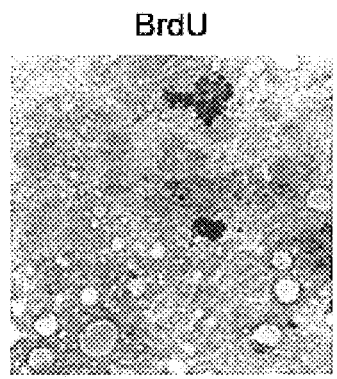
Figure 29C:
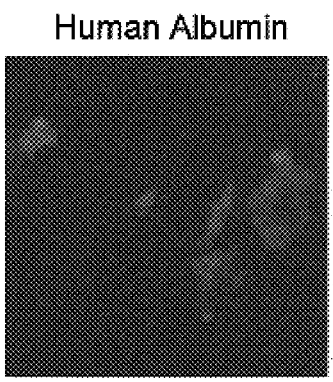
Figure 29D:
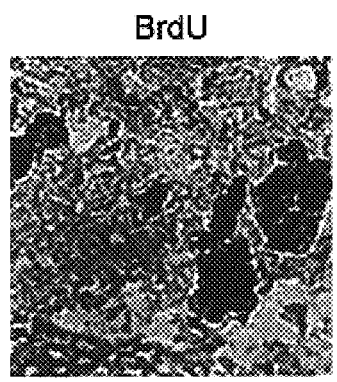
Figure 29E:
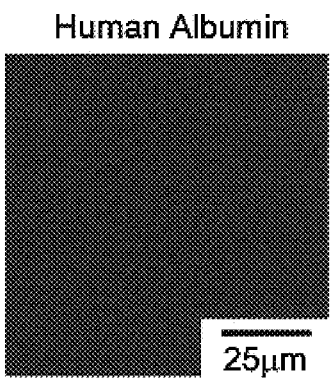
Figure 29F:
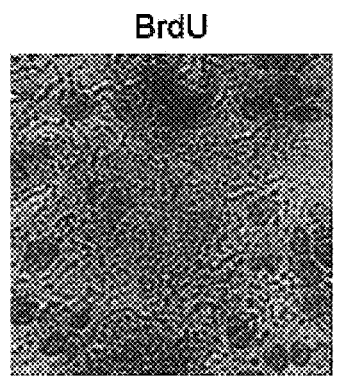

The results of these studies are shown in FIGS. 29A–F. Liver sections from control, non-tolerized, non-T3 treated rats were negative for both human albumin and BrdU staining (FIGS. 29E and F). Livers sections from tolerized, non-transplanted rats treated with T3 were negative for human albumin, but showed BrdU staining indicating that T3 treatment stimulated host rat liver cell proliferation (FIGS. 29A and B). Liver sections from tolerized, transplanted with human hepatocytes and treated with T3 had cells that were positive for both human albumin (FIG. 29C) and BrdU (FIG. 29D) indicating that transplanted human hepatocytes survived, were functional and proliferated when given a growth stimulus by T3.

13. EXAMPLE

Establishing HCV Infection in Chimeric Human-Rat Livers in Tolerized Rats

Rats were tolerized with either $10^5$ Huh7 cells, HepG2 cells or primary human hepatocytes at 16th gestation day. HepG2 can support HBV replication in culture. The cell lines were used as they are readily available and can be easily cultured. On day 1 after birth, tolerized rats were transplanted with $2 \times 10^6$ cells. One week after transplantation, rats were inoculated with $10^5$ copies of HCV RNA.

The transplantation groups were as follows. A "Huh7 rat" was tolerized and transplanted with Huh7 cells and inoculated with HCV serum. A "HepG2 rat" was tolerized and transplanted with HepG2 cells and inoculated with HCV serum. A "PHH rat" was tolerized and transplanted with primary human hepatocytes and inoculated with HCV serum. a control "PBS rat" was mock tolerized and transplanted with PBS and inoculated with HCV serum.

At weekly intervals, serum was collected. At monthly intervals, groups of rats were sacrificed and livers removed. The presence of HCV RNA was determined in both serum and livers using RT-PCR.

The results of these experiments are shown in FIGS. 30–32. FIG. 30 shows the limit of sensitivity of RT-PCR assay for plus strand HCV RNA was 0.1 fg of RNA substrate. HCV plus strand RNA was determined in serum and livers of HCV infected animals using the same assay.

As shown in FIG. 31, serum HCV RNA was positive up to 16 weeks in HCV infected animals tolerized and transplanted with Huh7 liver cell line. Conclusive results were not obtained with either HepG2, another differentiated liver cell line, or with primary human hepatocytes (PHH); the particular preparation of primary human hepatocytes used in these specific experiments did not exhibit typical tolerization/transplantation behavior.

FIG. 32 shows that liver HCV RNA was positive up to 16 weeks in HCV infected animals tolerized and transplanted with Huh7 liver cell line. As set forth above, conclusive data from HepG2 and PHH rats was not obtained.

Various publications are cited herein, the contents of which are hereby incorporated by reference in their entireties.

---

What is claimed is:

1. A model system for Hepatitis C virus infection In humans, comprising a non-human mammal, wherein the mammal is immunocompetent but has been rendered immunologically tolerant to human hepatocytes by fetal tolerization and subsequently transplanted with human hepatocytes and infected with Hepatitis C virus, whereby replication of Hepatitis C virus occurs in the model system.

2. The model system of claim 1, wherein the human hepatocytes are cells of the Huh7 cell line.

3. A method of preparing a non-human fetal mammal to receive a human hepatocyte trasplant, comprising the steps of:
 (i) administering to the fetal mammal an effective amount of human heatoeytes, in a form selected from the group consisting of whole cells and a cell lysate, wherein the hepatocytes render the mammnal immunologically tolerant to human hepatocytes; and
 (ii) administering to the mammal an effective amount of an agent, wherein the agent is metabolized by hepatocytes to produce a cytotoxin.

4. The method of claim 3, wherein the agent is retrorsine.

5. The method of claim 3, further comprising, after step ii, and after the mammal has been born, the step of introducing human hepatocytes into the mammal, wherein the number of introduced hepatocytes is effective in colonizing the liver of the mammal.

6. The method of claim 5, wherein the human hepatocytes are cells of the Huh7 cell line.

\* \* \* \* \*